US011141466B2

(12) United States Patent
Verhagen et al.

(10) Patent No.: US 11,141,466 B2
(45) Date of Patent: Oct. 12, 2021

(54) MODULATION OF FVIII IMMUNOGENICITY BY TRUNCATED VWF

(71) Applicant: CSL Behring Lengnau AG, Lengnau (CH)

(72) Inventors: Anne Verhagen, Northcote (AU); Sabine Pestel, Marburg (DE); Thomas Weimer, Gladenbach (DE); Marco Hofmann, Lahntal-Sterzhausen (DE); Huy Huynh, Brunswick (AU); Eugene Maraskovsky, Kew (AU)

(73) Assignee: CSL Behring Lengnau AG, Lengnau (CH)

( * ) Notice: Subject to any disclaimer, the term of this patent is extended or adjusted under 35 U.S.C. 154(b) by 0 days.

(21) Appl. No.: 16/624,365

(22) PCT Filed: Jun. 22, 2018

(86) PCT No.: PCT/EP2018/066696
§ 371 (c)(1),
(2) Date: Dec. 19, 2019

(87) PCT Pub. No.: WO2018/234518
PCT Pub. Date: Dec. 27, 2018

(65) Prior Publication Data
US 2020/0197495 A1 Jun. 25, 2020

(30) Foreign Application Priority Data

Jun. 22, 2017 (EP) .................................. 17177477
Jan. 26, 2018 (EP) .................................. 18153579

(51) Int. Cl.
*A61K 38/00* (2006.01)
*A61K 38/37* (2006.01)

(52) U.S. Cl.
CPC .................................. *A61K 38/37* (2013.01)

(58) Field of Classification Search
CPC ....... A61K 38/37; A61K 38/36; C07K 14/755
See application file for complete search history.

(56) References Cited

U.S. PATENT DOCUMENTS

| 4,399,216 A | 8/1983 | Axel et al. |
|---|---|---|
| 6,403,077 B1 | 6/2002 | Strom et al. |
| 7,256,253 B2 | 8/2007 | Bridon et al. |
| 2004/0087778 A1 | 5/2004 | Feige et al. |
| 2010/0286047 A1 | 11/2010 | Kronthaler |
| 2014/0357564 A1 * | 12/2014 | Schulte .................... A61P 7/02 514/14.1 |

FOREIGN PATENT DOCUMENTS

| EP | 0117060 | 8/1984 |
|---|---|---|
| EP | 2796145 | 10/2014 |
| WO | WO 03/076567 | 9/2003 |
| WO | WO 2004/067566 | 8/2004 |
| WO | WO 2004/101740 | 11/2004 |
| WO | WO 2005/000892 | 1/2005 |
| WO | WO 2005/001025 | 1/2005 |
| WO | WO 2005/063808 | 7/2005 |
| WO | WO 2006/000448 | 1/2006 |
| WO | WO 2007/090584 | 8/2007 |
| WO | WO 2009/156137 | 12/2009 |
| WO | WO 2011/051489 | 5/2011 |
| WO | WO 2011/060242 | 5/2011 |
| WO | WO 2011/124718 | 10/2011 |
| WO | WO 2012/059486 | 5/2012 |
| WO | WO 2012/150319 | 11/2012 |
| WO | WO 2013/083858 | 6/2013 |
| WO | WO 2013/093760 | 6/2013 |
| WO | WO 2013/106787 | 7/2013 |
| WO | WO 2013/120939 | 8/2013 |
| WO | WO 2013/135896 | 9/2013 |
| WO | WO 2013/160005 | 10/2013 |
| WO | WO-2013160005 A1 * | 10/2013 ............. A61K 38/36 |
| WO | WO 2014/072481 | 5/2014 |
| WO | WO 2014/198699 | 12/2014 |
| WO | WO 2015/185758 | 12/2015 |
| WO | WO 2016/000039 | 1/2016 |
| WO | WO-2016000039 A1 * | 1/2016 ........... C07K 14/765 |
| WO | WO 2016/188905 | 12/2016 |
| WO | WO 2016/188907 | 12/2016 |
| WO | WO-2016188905 A1 * | 12/2016 ........... C07K 14/473 |

(Continued)

OTHER PUBLICATIONS

Ghosh et al. Immune Response to FVIII in Hemophilia A: An Overview of Risk Factors. Clinic Rev Allerg Immunol (2009) 37:58-66 (Year: 2009).*
Graham et al., "A New Technique for the Assay of Infectivity of Huma Adenovirus 5 DNA," Virology, 1973, 52, pp. 456-467.
Graham et al. "Characteristics of a Human Cell Line Transformed by DNA from Human Adenovirus Type 5," J. Gen. Virol., 1977, vol. 36, pp. 59-72.
Mantei et al., "Rabbit ß-globin mRNA Production in Mouse L cells transformed with cloned rabbit ß-globin chromosomal DNA," Nature, 1979, vol. 281, pp. 40-46.
Mather, "Establishment and Characterization of Two Distinct Mouse Testicular Epithelial Cell Lines," Biology of Reproduction, 1980, vol. 23, pp. 243-252.
Urlaub et al., "Isolation of Chinese Hamster Cell Mutants Deficient in Dihydrofolate Reductase Activity," Proc. Natl. Academy Science USA, 1980, vol. 77, No. 7, pp. 4216-4220.

(Continued)

*Primary Examiner* — James H Alstrum-Acevedo
*Assistant Examiner* — Mercy H Sabila
(74) *Attorney, Agent, or Firm* — Finnegan, Henderson, Farabow, Garrett & Dunner, LLP

(57) ABSTRACT

The present invention relates to a recombinant polypeptide comprising a truncated von Willebrand Factor (VWF) capable of binding to blood coagulation Factor VIII (FVIII) for use in reducing the immunogenicity of Factor VIII (FVIII) wherein said recombinant polypeptide and a blood coagulation Factor VIII (FVIII) protein are co-administered to a subject suffering from a 10 blood coagulation disorder. The invention further relates to pharmaceutical compositions and kits for said use.

20 Claims, 13 Drawing Sheets
Specification includes a Sequence Listing.

(56) References Cited

FOREIGN PATENT DOCUMENTS

| WO | WO 2017/117630 | 7/2017 |
|---|---|---|
| WO | WO 2017/117631 | 7/2017 |

OTHER PUBLICATIONS

Gething et al., "Cell-Surface Expression of Influenza Haemagglutinin From a Cloned DNA Copy of the RNA Gene," Nature, 1981, vol., 293, pp. 620-625.

Mather et al., "Culture of Testicular Cells in Hormone-Supplemented Serum-Free Medium," Annals New York Academy of Sciences, 1982, vol. 383, pp. 44-68.

Lee et al., "An Effect of Predilution on Potency Assays of Factor VII Concentrates," Thrombosis Research 1983, 30, pp. 511-519.

Vehar et al., "Structure of human factor VIII," Nature, 1984, vol. 312, No. 22, pp. 337-342.

Wood et al., "Expression of active human factor VIII from recombinant DNA clones," Nature, 1984, vol. 312, No. 22, pp. 330-337.

Collins et al., "Molecular Cloning of the Human Gene for von Willebrand Factor and Identification of the Transcription Initiation Site," Proc. Natl. Acad. Sci. USA, 1987, vol. 84, pp. 4393-4397.

Mansour et al., "Disruption of the Proto-oncogene int-2 in Mouse Embryo-derived Stem Cells: A General Strategy for Targeting Mutations to Non-Selectable Genes," Nature, 1988, vol. 336, pp. 348-352.

Kaufman et al., "Effect of von Willebrand Factor Coexpression on the Synthesis and Secretion of Factor VIII in Chinese Hamster Ovary Cells," Molecular and Cellular Biology, 1989, vol. 9, pp. 1233-1242.

Keown et al., "Methods for Introducing DNA into Mammalian Cells," Introducing DNA into Mammalian Cells, Methods in Enzymology, 1990, vol. 185, pp. 527-537.

Hawley-Nelson et al., "LipofectAMINE™ REAGENT: A New, Higher Efficiency Polycationic Liposome Transfection Reagent," FOCUS, 1993, vol. 15, No. 3, pp. 73-79.

Fischer et al., "Structural Analysis of Recombinant von Willebrand Factor: Identification of Hetero- and Homo-Dimers," FEBS Letters, 1994, 351, pp. 345-348.

Josic et al., "Size-exclusion chromatography of plasma proteins with high molecular masses," Journal of Chromatography A., 1998, vol. 796, pp. 289-298.

Vlot et al, "The Half-life of Infused Factor VIII is Shorter in Hemophiliac Patients with Blood Group 0 than in those with Blood Group A," Thromb. Haemost., 2000, vol. 83, pp. 65-69.

Saenko et al., "Molecular defects in coagulation Factor VIII and their impact on Factor VIII function," Vox Sanguinis, 2002, vol. 83, pp. 89-96.

Dumont et al., "Monomeric Fc Fusions, Impact on Pharmacokinetic and Biological Activity of Protein Therapeutics" Biodrugs, 2006, vol. 20, No. 3, pp. 151-160.

Escuriola Ettingsausen et al., "Recombinant vs. plasma-Derived products, especially those with intact VWF, regarding inhibitor development" Haemophilia, 2006, vol. 12 (Suppl. 6), pp. 102-106.

Schellenberger et al., "A Recombinant Polypeptide Extends the In Vivo Half-Life of Peptides and Proteins in a Tunable Manner," Nature Biotechnology, 2009, vol. 27, No. 12, pp. 1186-1190.

Delignat,et al., "Immunoprotective effect of von Willebrand factor towards therapeutic factor VIII in experimental haemophilia A," Haemophilia, 2012, vol. 18, pp. 248-254.

Ragni, "von Willebrand factor: factor VIII protector and friend," Journal of Thrombosis and Haemostasis, 2012, vol. 10, pp. 2324-2327.

Zhou et al., "Sequence and Structure Relationships Within von Willebrand Factor," Blood, 2012, vol. 120, No. 2, pp. 449-458.

Yee et al., "A von Willebrand Factor Fragment Containing the D'D3 Domains is Sufficient to Stabilize Coagulation Factor Viii in Mice," Blood, 2014, vol. 124, No. 3, pp. 445-452.

Peyvandi et al., "A Randomized Trial of Factor VIII and Neutralizing Antibodies in Hemophilia A," N. Engl. J. Med, 2016, vol. 374, No. 21, pp. 2054-2064.

Xue et al., "Contribution of enhanced engagement of antigen presentation machinery to the clinical immunogenicity of a human interleukin (IL)-21 receptor-blocking therapeutic antibody," Clinical and Experimental Immunology, 2015, vol. 183, pp. 102-113.

Lamberth et al., "Post hoc assessment of the immunogenicity of bioengineered factor VIIa demonstrates the use of preclinical tools," Science Translational Medicine, 9, eaag1286 (2017), pp. 1-11.

Leone et al., "Surface LAMP-2 is an Endocytic Receptor that Diverts Antigen Internalized by Human Dendritic Cells into Highly Immunogenic Exosomes," The Journal of Immunology, 2017, vol. 199, pp. 531-546.

International Search Report of International Application No. PCT/EP2018/066696, dated Oct. 1, 2018, 3 pages.

Written Opinion of the International Searching Authority for PCT/EP2018/066696, dated Oct. 1, 2018, 6 pages.

* cited by examiner

A

B

C

A

B

A

B

C

A

B

C

D

E

F

SEQUENCE LISTING

```
<160> NUMBER OF SEQ ID NOS: 6

<210> SEQ ID NO 1
<211> LENGTH: 5616
<212> TYPE: DNA
<213> ORGANISM: Artificial Sequence
<220> FEATURE:
<223> OTHER INFORMATION: DNA encoding construct VWF fragment - G/S
      Linker - albumin
<220> FEATURE:
<221> NAME/KEY: misc_feature
<222> LOCATION: (1)..(6)
<223> OTHER INFORMATION: EcoRI restriction enzyme cleavage site
<220> FEATURE:
<221> NAME/KEY: misc_feature
<222> LOCATION: (32)..(3757)
<223> OTHER INFORMATION: coding sequence for VWF amino acids 1 to 1242
<220> FEATURE:
<221> NAME/KEY: misc_feature
<222> LOCATION: (3758)..(3850)
<223> OTHER INFORMATION: coding sequence for glycine/serine linker
<220> FEATURE:
<221> NAME/KEY: misc_feature
<222> LOCATION: (3851)..(5608)
<223> OTHER INFORMATION: coding sequence for human albumin
<220> FEATURE:
<221> NAME/KEY: misc_feature
<222> LOCATION: (5609)..(5616)
<223> OTHER INFORMATION: NotI restriction enzyme cleavage site

<400> SEQUENCE: 1
gaattcccgc agccctcatt tgcaggggaa gatgattcct gccagatttg ccggggtgct      60
gcttgctctg gccctcattt tgccaggggac cctttgtgca gaaggaactc gcggcaggtc    120
atccacggcc cgatgcagcc ttttcggaag tgacttcgtc aacacctttg atgggagcat    180
gtacagcttt gcgggatact gcagttacct cctggcaggg ggctgccaga aacgctcctt    240
ctcgattatt ggggacttcc agaatggcaa gagagtgagc ctctccgtgt atcttgggga    300 atttttttgac atccatttgt ttgtcaatgg taccgtgaca caggggggacc aaagagtctc    360 catgccctat gcctccaaag ggctgtatct agaaactgag gctgggtact acaagctgtc    420
cggtgaggcc tatggctttg tggccaggat cgatggcagc ggcaactttc aagtcctgct    480
gtcagacaga tacttcaaca agacctgcgg gctgtgtggc aactttaaca tctttgctga    540
agatgacttt atgacccaag aagggaccct gacctcggac ccttatgact ttgccaactc    600
atgggctctg agcagtggag aacagtggtg tgaacggca tctcctccca gcagctcatg    660
caacatctcc tctggggaaa tgcagaaggg cctgtgggag cagtgccagc ttctgaagag    720
cacctcggtg tttgcccgct gccaccctct ggtggacccc gagccttttg tggccctgtg    780
tgagaagact ttgtgtgagt gtgctggggg gctggagtgc gcctgccctg ccctcctgga    840
```

-continued

```
gtacgcccgg acctgtgccc aggagggaat ggtgctgtac ggctggaccg accacagcgc    900
gtgcagccca gtgtgccctg ctggtatgga gtataggcag tgtgtgtccc cttgcgccag    960
gacctgccag agcctgcaca tcaatgaaat gtgtcaggag cgatgcgtgg atggctgcag   1020
ctgccctgag ggacagctcc tggatgaagg cctctgcgtg gagagcaccg agtgtccctg   1080
cgtgcattcc ggaaagcgct accctcccgg cacctccctc tctcgagact gcaacacctg   1140
catttgccga acagccagt ggatctgcag caatgaagaa tgtccagggg agtgccttgt    1200
cacaggtcaa tcacacttca agagctttga caacagatac ttcaccttca gtgggatctg   1260
ccagtacctg ctggcccggg attgccagga ccactccttc tccattgtca ttgagactgt   1320
ccagtgtgct gatgaccgcg acgctgtgtg cacccgctcc gtcaccgtcc ggctgcctgg   1380
cctgcacaac agccttgtga aactgaagca tggggcagga gttgccatgg atggccagga   1440
cgtccagctc cccctcctga aggtgacct ccgcatccag catacagtga cggcctccgt    1500
gcgcctcagc tacggggagg acctgcagat ggactgggat ggccgcggga ggctgctggt   1560
gaagctgtcc cccgtctatg ccgggaagac ctgcggcctg tgtgggaatt acaatggcaa   1620
ccagggcgac gacttcctta ccccctctgg gctggcggag ccccgggtgg aggacttcgg   1680
gaacgcctgg aagctgcacg gggactgcca ggacctgcag aagcagcaca gcgatccctg   1740
cgcccctcaac ccgcgcatga ccaggttctc cgaggaggcg tgcgcggtcc tgacgtcccc   1800
cacattcgag gcctgccatc gtgccgtcag cccgctgccc tacctgcgga actgccgcta   1860
cgacgtgtgc tcctgctcgg acggccgcga gtgcctgtgc ggcgccctgg ccagctatgc   1920
cgcggcctgc gcggggagag gcgtgcgcgt cgcgtggcgc gagccaggcc gctgtgagct   1980
gaactgcccg aaaggccagg tgtacctgca gtgcgggacc ccctgcaacc tgacctgccg   2040
ctctctctct taccccggatg aggaatgcaa tgaggcctgc ctggagggct gcttctgccc   2100
cccagggctc tacatggatg agagggggga ctgcgtgccc aaggcccagt gccctgttaa   2160
ctatgacggt gagatcttcc agccagaaga catcttctca gaccatcaca ccatgtgcta   2220
ctgtgaggat ggcttcatgc actgtaccat gagtggagtc cccggaagct gctgcctga    2280
cgctgtcctc agcagtcccc tgtctcatcg cagcaaaagg agcctatcct gtcggccccc   2340
catggtcaag ctggtgtgtc ccgctgacaa cctgcgggct gaagggctcg agtgtaccaa   2400
aacgtgccag aactatgacc tggagtgcat gagcatgggc tgtgtctctg ctgcctctg    2460
ccccccgggc atggtccggc atgagaacag atgtgtggcc ctggaaaggt gtcctgctt    2520
ccatcagggc aaggagtatg cccctggaga acagtgaag attggctgca acacttgtgt    2580
ctgtcgggac cggaagtgga actgcacaga ccatgtgtgt gatgccacgt gctccacgat   2640
cggcatggcc cactacctca ccttcgacgg gctcaaatac ctgttccccg ggagtgcca    2700
gtacgttctg gtgcaggatt actgcggcag taaccctggg acctttcgga tcctagtggg   2760
gaataaggga tgcagccacc cctcagtgaa atgcaagaaa cgggtcacca tcctggtgga   2820
gggaggagag attgagctgt ttgacgggga ggtgaatgtg aagaggccca tgaaggatga   2880
gactcacttt gaggtggtgg agtctggccg gtacatcatt ctgctgctgg gcaaagccct   2940
ctccgtggtc tgggaccgcc acctgagcat tccgtggtc ctgaagcaga cataccagga   3000
gaaagtgtgt ggcctgtgtg gaattttga tggcatccag aacaatgacc tcaccagcag   3060
caacctccaa gtggaggaag accctgtgga ctttggaaac tcctggaaag tgagctcgca   3120
gtgtgctgac accagaaaag tgcctctgga ctcatcccct gccacctgcc ataacaacat   3180
catgaagcag acgatggtgg attcctcctg tagaatcctt accagtgacg tcttccagga   3240
```

```
ctgcaacaag ctggtggacc ccgagccata tctggatgtc tgcatttacg acacctgctc   3300
ctgtgagtcc attggggact gcgcctgctt ctgcgacacc attgctgcct atgcccacgt   3360
gtgtgcccag catggcaagg tggtgacctg aggacggcc acattgtgcc cccagagctg    3420
cgaggagagg aatctccggg agaacgggta tgagtgtgag tggcgctata cagctgtgc    3480 acctgcctgt caagtcacgt gtcagcaccc tgagccactg gcctgccctg tgcagtgtgt   3540
ggagggctgc catgcccact gccctccagg gaaaatcctg gatgagcttt tgcagacctg   3600
cgttgaccct gaagactgtc cagtgtgtga ggtggctggc cggcgttttg cctcaggaaa   3660
gaaagtcacc ttgaatccca gtgaccctga gcactgccag atttgccact gtgatgttgt   3720
caacctcacc tgtgaagcct gccaggagcc gggaggctcg agcggggat ctggcgggtc     3780 tggaggctct ggagggtcgg gaggctctgg aggctctggg ggatctggcg ggtctggagg   3840
gtcgggatcc gatgcacaca agagtgaggt tgctcatcgg tttaaagatt tgggagaaga   3900
aaatttcaaa gccttggtgt tgattgcctt tgctcagtat cttcagcagt gtccatttga   3960
agatcatgta aaattagtga atgaagtaac tgaatttgca aaaacatgtg ttgctgatga   4020
gtcagctgaa aattgtgaca atcacttca taccctttt ggagacaaat tatgcacagt      4080
tgcaactctt cgtgaaacct atggtgaaat ggctgactgc tgtgcaaaac aagaacctga   4140
gagaaatgaa tgcttcttgc aacacaaaga tgacaaccca aacctccccc gattggtgag   4200
accagaggtt gatgtgatgt gcactgcttt tcatgacaat aagagacat tttgaaaaa      4260 atacttatat gaaattgcca gaagacatcc ttactttat gccccggaac tccttttctt     4320
tgctaaaagg tataaagctg cttttacaga atgttgccaa gctgctgata agctgcctg     4380 cctgttgcca aagctcgatg aacttcggga tgaagggaag gcttcgtctg ccaaacagag   4440
actcaagtgt gccagtctcc aaaaatttgg agaaagagct ttcaaagcat gggcagtagc   4500
tcgcctgagc cagagatttc ccaaagctga gtttgcagaa gtttccaagt tagtgacaga   4560
tcttaccaaa gtccacacgg aatgctgcca tggagatctg cttgaatgtg ctgatgacag   4620
ggcggaccct gccaagtata tctgtgaaaa tcaagattcg atctccagta aactgaagga   4680
atgctgtgaa aaacctctgt tggaaaaatc ccactgcatt gccgaagtgg aaaatgatga   4740
gatgcctgct gacttgcctt cattagctgc tgattttgtt gaaagtaagg atgtttgcaa   4800
aaactatgct gaggcaaagg atgtcttcct gggcatgttt ttgtatgaat atgcaagaag   4860
gcatcctgat tactctgtcg tgctgctgct gagacttgcc aagacatatg aaaccactct   4920
agagaagtgc tgtgccgctg cagatcctca tgaatgctat gccaaagtgt tcgatgaatt   4980
taaacctctt gtggaagagc ctcagaattt aatcaaacaa aattgtgagc ttttgagca    5040 gcttggagag tacaaattcc agaatgcgct attagttcgt tacaccaaga agtaccccca   5100
agtgtcaact ccaactcttg tagaggtctc aagaaaccta ggaaaagtgg gcagcaaatg   5160
ttgtaaacat cctgaagcaa aaagaatgcc ctgtgcagaa gactatctat ccgtggtcct   5220
gaaccagtta tgtgtgttgc atgagaaaac gccagtaagt gacagagtca ccaaatgctg   5280
cacagaatcc ttggtgaaca ggcgaccatg ctttttcagct ctggaagtcg atgaaacata   5340
cgttcccaaa gagtttaatg ctgaaacatt caccttccat gcagatatat gcacactttc   5400
tgagaaggag agacaaatca agaaacaaac tgcacttgtt gagctcgtga acacaagcc    5460 caaggcaaca aaagagcaac tgaaagctgt tatggatgat ttcgcagctt ttgtagagaa   5520
gtgctgcaag gctgacgata aggagacctg ctttgccgag gagggtaaaa aacttgttgc   5580
```

-continued tgcaagtcaa gctgccttag gcttataggc ggccgc                                    5616

<210> SEQ ID NO 2
<211> LENGTH: 1095
<212> TYPE: PRT
<213> ORGANISM: Artificial Sequence
<220> FEATURE:
<223> OTHER INFORMATION: polypeptide encoded by SEQ ID NO:1
<220> FEATURE:
<221> NAME/KEY: MISC_FEATURE
<222> LOCATION: (1)..(479)
<223> OTHER INFORMATION: VWF D?D3 region (VWF amino acids 764 - 1242)
<220> FEATURE:
<221> NAME/KEY: MISC_FEATURE
<222> LOCATION: (480)..(510)
<223> OTHER INFORMATION: glycine/serine linker
<220> FEATURE:
<221> NAME/KEY: MISC_FEATURE
<222> LOCATION: (511)..(1095)
<223> OTHER INFORMATION: human albumin

<400> SEQUENCE: 2

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val

```
              290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
                340                 345                 350
Lys Val Val Thr Trp Arg Thr Ala Thr Leu Cys Pro Gln Ser Cys Glu
                355                 360                 365
Glu Arg Asn Leu Arg Glu Asn Gly Tyr Glu Cys Glu Trp Arg Tyr Asn
370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
                420                 425                 430
Cys Pro Val Cys Glu Val Ala Gly Arg Arg Phe Ala Ser Gly Lys Lys
                435                 440                 445
Val Thr Leu Asn Pro Ser Asp Pro Glu His Cys Gln Ile Cys His Cys
                450                 455                 460
Asp Val Val Asn Leu Thr Cys Glu Ala Cys Gln Glu Pro Gly Gly Ser
465                 470                 475                 480
Ser Gly Gly Ser Gly Gly Ser Gly Gly Ser Gly Gly Ser Gly Gly Ser
                485                 490                 495
Gly Gly Ser Gly Gly Ser Gly Gly Ser Gly Ser Asp Ala
                500                 505                 510
His Lys Ser Glu Val Ala His Arg Phe Lys Asp Leu Gly Glu Glu Asn
                515                 520                 525
Phe Lys Ala Leu Val Leu Ile Ala Phe Ala Gln Tyr Leu Gln Gln Cys
                530                 535                 540
Pro Phe Glu Asp His Val Lys Leu Val Asn Glu Val Thr Glu Phe Ala
545                 550                 555                 560
Lys Thr Cys Val Ala Asp Glu Ser Ala Glu Asn Cys Asp Lys Ser Leu
                565                 570                 575
His Thr Leu Phe Gly Asp Lys Leu Cys Thr Val Ala Thr Leu Arg Glu
                580                 585                 590
Thr Tyr Gly Glu Met Ala Asp Cys Cys Ala Lys Gln Glu Pro Glu Arg
                595                 600                 605
Asn Glu Cys Phe Leu Gln His Lys Asp Asp Asn Pro Asn Leu Pro Arg
610                 615                 620
Leu Val Arg Pro Glu Val Asp Val Met Cys Thr Ala Phe His Asp Asn
625                 630                 635                 640
Glu Glu Thr Phe Leu Lys Lys Tyr Leu Tyr Glu Ile Ala Arg Arg His
                645                 650                 655
Pro Tyr Phe Tyr Ala Pro Glu Leu Leu Phe Phe Ala Lys Arg Tyr Lys
                660                 665                 670
Ala Ala Phe Thr Glu Cys Cys Gln Ala Ala Asp Lys Ala Ala Cys Leu
                675                 680                 685
Leu Pro Lys Leu Asp Glu Leu Arg Asp Glu Gly Lys Ala Ser Ser Ala
                690                 695                 700
Lys Gln Arg Leu Lys Cys Ala Ser Leu Gln Lys Phe Gly Glu Arg Ala
705                 710                 715                 720
```

```
Phe Lys Ala Trp Ala Val Ala Arg Leu Ser Gln Arg Phe Pro Lys Ala
                725                 730                 735
Glu Phe Ala Glu Val Ser Lys Leu Val Thr Asp Leu Thr Lys Val His
            740                 745                 750
Thr Glu Cys Cys His Gly Asp Leu Leu Glu Cys Ala Asp Asp Arg Ala
        755                 760                 765
Asp Leu Ala Lys Tyr Ile Cys Glu Asn Gln Asp Ser Ile Ser Ser Lys
    770                 775                 780
Leu Lys Glu Cys Cys Glu Lys Pro Leu Leu Glu Lys Ser His Cys Ile
785                 790                 795                 800
Ala Glu Val Glu Asn Asp Glu Met Pro Ala Asp Leu Pro Ser Leu Ala
                805                 810                 815
Ala Asp Phe Val Glu Ser Lys Asp Val Cys Lys Asn Tyr Ala Glu Ala
            820                 825                 830
Lys Asp Val Phe Leu Gly Met Phe Leu Tyr Glu Tyr Ala Arg Arg His
        835                 840                 845
Pro Asp Tyr Ser Val Val Leu Leu Leu Arg Leu Ala Lys Thr Tyr Glu
    850                 855                 860
Thr Thr Leu Glu Lys Cys Cys Ala Ala Ala Asp Pro His Glu Cys Tyr
865                 870                 875                 880
Ala Lys Val Phe Asp Glu Phe Lys Pro Leu Val Glu Glu Pro Gln Asn
                885                 890                 895
Leu Ile Lys Gln Asn Cys Glu Leu Phe Glu Gln Leu Gly Glu Tyr Lys
            900                 905                 910
Phe Gln Asn Ala Leu Leu Val Arg Tyr Thr Lys Lys Val Pro Gln Val
        915                 920                 925
Ser Thr Pro Thr Leu Val Glu Val Ser Arg Asn Leu Gly Lys Val Gly
    930                 935                 940
Ser Lys Cys Cys Lys His Pro Glu Ala Lys Arg Met Pro Cys Ala Glu
945                 950                 955                 960
Asp Tyr Leu Ser Val Val Leu Asn Gln Leu Cys Val Leu His Glu Lys
                965                 970                 975
Thr Pro Val Ser Asp Arg Val Thr Lys Cys Cys Thr Glu Ser Leu Val
            980                 985                 990
Asn Arg Arg Pro Cys Phe Ser Ala Leu Glu Val Asp Glu Thr Tyr Val
        995                1000                1005
Pro Lys Glu Phe Asn Ala Glu Thr Phe Thr Phe His Ala Asp Ile
    1010                1015                1020
Cys Thr Leu Ser Glu Lys Glu Arg Gln Ile Lys Lys Gln Thr Ala
    1025                1030                1035
Leu Val Glu Leu Val Lys His Lys Pro Lys Ala Thr Lys Glu Gln
    1040                1045                1050
Leu Lys Ala Val Met Asp Asp Phe Ala Ala Phe Val Glu Lys Cys
    1055                1060                1065
Cys Lys Ala Asp Asp Lys Glu Thr Cys Phe Ala Glu Glu Gly Lys
    1070                1075                1080
Lys Leu Val Ala Ala Ser Gln Ala Ala Leu Gly Leu
    1085                1090                1095

<210> SEQ ID NO 3
<211> LENGTH: 8442
<212> TYPE: DNA
<213> ORGANISM: Homo sapiens
<220> FEATURE:
```

```
<221> NAME/KEY: CDS
<222> LOCATION: (1)..(8442)

<400> SEQUENCE: 3 atg att cct gcc aga ttt gcc ggg gtg ctg ctt gct ctg gcc ctc att     48
Met Ile Pro Ala Arg Phe Ala Gly Val Leu Leu Ala Leu Ala Leu Ile
1               5                   10                  15 ttg cca ggg acc ctt tgt gca gaa gga act cgc ggc agg tca tcc acg     96
Leu Pro Gly Thr Leu Cys Ala Glu Gly Thr Arg Gly Arg Ser Ser Thr
            20                  25                  30 gcc cga tgc agc ctt ttc gga agt gac ttc gtc aac acc ttt gat ggg    144
Ala Arg Cys Ser Leu Phe Gly Ser Asp Phe Val Asn Thr Phe Asp Gly
        35                  40                  45 agc atg tac agc ttt gcg gga tac tgc agt tac ctc ctg gca ggg ggc    192
Ser Met Tyr Ser Phe Ala Gly Tyr Cys Ser Tyr Leu Leu Ala Gly Gly
    50                  55                  60 tgc cag aaa cgc tcc ttc tcg att att ggg gac ttc cag aat ggc aag    240
Cys Gln Lys Arg Ser Phe Ser Ile Ile Gly Asp Phe Gln Asn Gly Lys
65                  70                  75                  80 aga gtg agc ctc tcc gtg tat ctt ggg gaa ttt ttt gac atc cat ttg    288
Arg Val Ser Leu Ser Val Tyr Leu Gly Glu Phe Phe Asp Ile His Leu
                85                  90                  95 ttt gtc aat ggt acc gtg aca cag ggg gac caa aga gtc tcc atg ccc    336
Phe Val Asn Gly Thr Val Thr Gln Gly Asp Gln Arg Val Ser Met Pro
            100                 105                 110 tat gcc tcc aaa ggg ctg tat cta gaa act gag gct ggg tac tac aag    384
Tyr Ala Ser Lys Gly Leu Tyr Leu Glu Thr Glu Ala Gly Tyr Tyr Lys
        115                 120                 125 ctg tcc ggt gag gcc tat ggc ttt gtg gcc agg atc gat ggc agc ggc    432
Leu Ser Gly Glu Ala Tyr Gly Phe Val Ala Arg Ile Asp Gly Ser Gly
    130                 135                 140 aac ttt caa gtc ctg ctg tca gac aga tac ttc aac aag acc tgc ggg    480
Asn Phe Gln Val Leu Leu Ser Asp Arg Tyr Phe Asn Lys Thr Cys Gly
145                 150                 155                 160 ctg tgt ggc aac ttt aac atc ttt gct gaa gat gac ttt atg acc caa    528
Leu Cys Gly Asn Phe Asn Ile Phe Ala Glu Asp Asp Phe Met Thr Gln
                165                 170                 175 gaa ggg acc ttg acc tcg gac cct tat gac ttt gcc aac tca tgg gct    576
Glu Gly Thr Leu Thr Ser Asp Pro Tyr Asp Phe Ala Asn Ser Trp Ala
            180                 185                 190 ctg agc agt gga gaa cag tgg tgt gaa cgg gca tct cct ccc agc agc    624
Leu Ser Ser Gly Glu Gln Trp Cys Glu Arg Ala Ser Pro Pro Ser Ser
        195                 200                 205 tca tgc aac atc tcc tct ggg gaa atg cag aag ggc ctg tgg gag cag    672
Ser Cys Asn Ile Ser Ser Gly Glu Met Gln Lys Gly Leu Trp Glu Gln
    210                 215                 220 tgc cag ctt ctg aag agc acc tcg gtg ttt gcc cgc tgc cac cct ctg    720
Cys Gln Leu Leu Lys Ser Thr Ser Val Phe Ala Arg Cys His Pro Leu
225                 230                 235                 240 gtg gac ccc gag cct ttt gtg gcc ctg tgt gag aag act ttg tgt gag    768
Val Asp Pro Glu Pro Phe Val Ala Leu Cys Glu Lys Thr Leu Cys Glu
                245                 250                 255 tgt gct ggg ggg ctg gag tgc gcc tgc cct gcc ctc ctg gag tac gcc    816
Cys Ala Gly Gly Leu Glu Cys Ala Cys Pro Ala Leu Leu Glu Tyr Ala
            260                 265                 270 cgg acc tgt gcc cag gag gga atg gtg ctg tac ggc tgg acc gac cac    864
Arg Thr Cys Ala Gln Glu Gly Met Val Leu Tyr Gly Trp Thr Asp His
        275                 280                 285 agc gcg tgc agc cca gtg tgc cct gct ggt atg gag tat agg cag tgt    912
Ser Ala Cys Ser Pro Val Cys Pro Ala Gly Met Glu Tyr Arg Gln Cys
```

-continued

```
      290               295                300
gtg tcc cct tgc gcc agg acc tgc cag agc ctg cac atc aat gaa atg    960
Val Ser Pro Cys Ala Arg Thr Cys Gln Ser Leu His Ile Asn Glu Met
305                 310                 315                 320 tgt cag gag cga tgc gtg gat ggc tgc agc tgc cct gag gga cag ctc   1008
Cys Gln Glu Arg Cys Val Asp Gly Cys Ser Cys Pro Glu Gly Gln Leu
                325                 330                 335 ctg gat gaa ggc ctc tgc gtg gag agc acc gag tgt ccc tgc gtg cat   1056
Leu Asp Glu Gly Leu Cys Val Glu Ser Thr Glu Cys Pro Cys Val His
            340                 345                 350 tcc gga aag cgc tac cct ccc ggc acc tcc ctc tct cga gac tgc aac   1104
Ser Gly Lys Arg Tyr Pro Pro Gly Thr Ser Leu Ser Arg Asp Cys Asn
        355                 360                 365 acc tgc att tgc cga aac agc cag tgg atc tgc agc aat gaa gaa tgt   1152
Thr Cys Ile Cys Arg Asn Ser Gln Trp Ile Cys Ser Asn Glu Glu Cys
    370                 375                 380 cca ggg gag tgc ctt gtc aca ggt caa tca cac ttc aag agc ttt gac   1200
Pro Gly Glu Cys Leu Val Thr Gly Gln Ser His Phe Lys Ser Phe Asp
385                 390                 395                 400 aac aga tac ttc acc ttc agt ggg atc tgc cag tac ctg ctg gcc cgg   1248
Asn Arg Tyr Phe Thr Phe Ser Gly Ile Cys Gln Tyr Leu Leu Ala Arg
                405                 410                 415 gat tgc cag gac cac tcc ttc tcc att gtc att gag act gtc cag tgt   1296
Asp Cys Gln Asp His Ser Phe Ser Ile Val Ile Glu Thr Val Gln Cys
            420                 425                 430 gct gat gac cgc gac gct gtg tgc acc cgc tcc gtc acc gtc cgg ctg   1344
Ala Asp Asp Arg Asp Ala Val Cys Thr Arg Ser Val Thr Val Arg Leu
        435                 440                 445 cct ggc ctg cac aac agc ctt gtg aaa ctg aag cat ggg gca gga gtt   1392
Pro Gly Leu His Asn Ser Leu Val Lys Leu Lys His Gly Ala Gly Val
    450                 455                 460 gcc atg gat ggc cag gac gtc cag ctc ccc ctc ctg aaa ggt gac ctc   1440
Ala Met Asp Gly Gln Asp Val Gln Leu Pro Leu Leu Lys Gly Asp Leu
465                 470                 475                 480 cgc atc cag cat aca gtg acg gcc tcc gtg cgc ctc agc tac ggg gag   1488
Arg Ile Gln His Thr Val Thr Ala Ser Val Arg Leu Ser Tyr Gly Glu
                485                 490                 495 gac ctg cag atg gac tgg gat ggc cgc ggg agg ctg ctg gtg aag ctg   1536
Asp Leu Gln Met Asp Trp Asp Gly Arg Gly Arg Leu Leu Val Lys Leu
            500                 505                 510 tcc ccc gtc tat gcc ggg aag acc tgc ggc ctg tgt ggg aat tac aat   1584
Ser Pro Val Tyr Ala Gly Lys Thr Cys Gly Leu Cys Gly Asn Tyr Asn
        515                 520                 525 ggc aac cag ggc gac gac ttc ctt acc ccc tct ggg ctg gcg gag ccc   1632
Gly Asn Gln Gly Asp Asp Phe Leu Thr Pro Ser Gly Leu Ala Glu Pro
    530                 535                 540 cgg gtg gag gac ttc ggg aac gcc tgg aag ctg cac ggg gac tgc cag   1680
Arg Val Glu Asp Phe Gly Asn Ala Trp Lys Leu His Gly Asp Cys Gln
545                 550                 555                 560 gac ctg cag aag cag cac agc gat ccc tgc gcc ctc aac ccg cgc atg   1728
Asp Leu Gln Lys Gln His Ser Asp Pro Cys Ala Leu Asn Pro Arg Met
                565                 570                 575 acc agg ttc tcc gag gag gcg tgc gcg gtc ctg acg tcc ccc aca ttc   1776
Thr Arg Phe Ser Glu Glu Ala Cys Ala Val Leu Thr Ser Pro Thr Phe
            580                 585                 590 gag gcc tgc cat cgt gcc gtc agc ccg ctg ccc tac ctg cgg aac tgc   1824
Glu Ala Cys His Arg Ala Val Ser Pro Leu Pro Tyr Leu Arg Asn Cys
        595                 600                 605 cgc tac gac gtg tgc tcc tgc tcg gac ggc cgc gag tgc ctg tgc ggc   1872
```

|  |  |  |  |  |  |  |  |  |  |  |  |  |  |  |
|---|---|---|---|---|---|---|---|---|---|---|---|---|---|---|
| Arg | Tyr | Asp | Val | Cys | Ser | Cys | Ser | Asp | Gly | Arg | Glu | Cys | Leu | Cys | Gly |
| 610 |  |  |  | 615 |  |  |  | 620 |  |  |  |  |  |  |

```
gcc ctg gcc agc tat gcc gcg gcc tgc gcg ggg aga ggc gtg cgc gtc    1920
Ala Leu Ala Ser Tyr Ala Ala Ala Cys Ala Gly Arg Gly Val Arg Val
625             630             635             640 gcg tgg cgc gag cca ggc cgc tgt gag ctg aac tgc ccg aaa ggc cag    1968
Ala Trp Arg Glu Pro Gly Arg Cys Glu Leu Asn Cys Pro Lys Gly Gln
        645             650             655 gtg tac ctg cag tgc ggg acc ccc tgc aac ctg acc tgc cgc tct ctc    2016
Val Tyr Leu Gln Cys Gly Thr Pro Cys Asn Leu Thr Cys Arg Ser Leu
660             665             670 tct tac ccg gat gag gaa tgc aat gag gcc tgc ctg gag ggc tgc ttc    2064
Ser Tyr Pro Asp Glu Glu Cys Asn Glu Ala Cys Leu Glu Gly Cys Phe
            675             680             685 tgc ccc cca ggg ctc tac atg gat gag agg ggg gac tgc gtc ccc aag    2112
Cys Pro Pro Gly Leu Tyr Met Asp Glu Arg Gly Asp Cys Val Pro Lys
    690             695             700 gcc cag tgc ccc tgt tac tat gac ggt gag atc ttc cag cca gaa gac    2160
Ala Gln Cys Pro Cys Tyr Tyr Asp Gly Glu Ile Phe Gln Pro Glu Asp
705             710             715             720 atc ttc tca gac cat cac acc atg tgc tac tgt gag gat ggc ttc atg    2208
Ile Phe Ser Asp His His Thr Met Cys Tyr Cys Glu Asp Gly Phe Met
                725             730             735 cac tgt acc atg agt gga gtc ccc gga agc ttg ctg cct gac gct gtc    2256
His Cys Thr Met Ser Gly Val Pro Gly Ser Leu Leu Pro Asp Ala Val
            740             745             750 ctc agc agt ccc ctg tct cat cgc agc aaa agg agc cta tcc tgt cgg    2304
Leu Ser Ser Pro Leu Ser His Arg Ser Lys Arg Ser Leu Ser Cys Arg
        755             760             765 ccc ccc atg gtc aag ctg gtg tgt ccc gct gac aac ctg cgg gct gaa    2352
Pro Pro Met Val Lys Leu Val Cys Pro Ala Asp Asn Leu Arg Ala Glu
770             775             780 ggg ctc gag tgt acc aaa acg tgc cag aac tat gac ctg gag tgc atg    2400
Gly Leu Glu Cys Thr Lys Thr Cys Gln Asn Tyr Asp Leu Glu Cys Met
785             790             795             800 agc atg ggc tgt gtc tct ggc tgc ctc tgc ccc ccg ggc atg gtc cgg    2448
Ser Met Gly Cys Val Ser Gly Cys Leu Cys Pro Pro Gly Met Val Arg
                805             810             815 cat gag aac aga tgt gtg gcc ctg gaa agg tgt ccc tgc ttc cat cag    2496
His Glu Asn Arg Cys Val Ala Leu Glu Arg Cys Pro Cys Phe His Gln
            820             825             830 ggc aag gag tat gcc cct gga gaa aca gtg aag att ggc tgc aac act    2544
Gly Lys Glu Tyr Ala Pro Gly Glu Thr Val Lys Ile Gly Cys Asn Thr
        835             840             845 tgt gtc tgt cgg gac cgg aag tgg aac tgc aca gac cat gtg tgt gat    2592
Cys Val Cys Arg Asp Arg Lys Trp Asn Cys Thr Asp His Val Cys Asp
850             855             860 gcc acg tgc tcc acg atc ggc atg gcc cac tac ctc acc ttc gac ggg    2640
Ala Thr Cys Ser Thr Ile Gly Met Ala His Tyr Leu Thr Phe Asp Gly
865             870             875             880 ctc aaa tac ctg ttc ccc ggg gag tgc cag tac gtt ctg gtg cag gat    2688
Leu Lys Tyr Leu Phe Pro Gly Glu Cys Gln Tyr Val Leu Val Gln Asp
                885             890             895 tac tgc ggc agt aac cct ggg acc ttt cgg atc cta gtg ggg aat aag    2736
Tyr Cys Gly Ser Asn Pro Gly Thr Phe Arg Ile Leu Val Gly Asn Lys
            900             905             910 gga tgc agc cac ccc tca gtg aaa tgc aag aaa cgg gtc acc atc ctg    2784
Gly Cys Ser His Pro Ser Val Lys Cys Lys Lys Arg Val Thr Ile Leu
        915             920             925
```

```
gtg gag gga gga gag att gag ctg ttt gac ggg gag gtg aat gtg aag    2832
Val Glu Gly Gly Glu Ile Glu Leu Phe Asp Gly Glu Val Asn Val Lys
            930                 935                 940 agg ccc atg aag gat gag act cac ttt gag gtg gtg gag tct ggc cgg    2880
Arg Pro Met Lys Asp Glu Thr His Phe Glu Val Val Glu Ser Gly Arg
945                 950                 955                 960 tac atc att ctg ctg ctg ggc aaa gcc ctc tcc gtg gtc tgg gac cgc    2928
Tyr Ile Ile Leu Leu Leu Gly Lys Ala Leu Ser Val Val Trp Asp Arg
                965                 970                 975 cac ctg agc atc tcc gtg gtc ctg aag cag aca tac cag gag aaa gtg    2976
His Leu Ser Ile Ser Val Val Leu Lys Gln Thr Tyr Gln Glu Lys Val
            980                 985                 990 tgt ggc ctg tgt ggg aat ttt gat ggc atc cag aac aat gac ctc acc    3024
Cys Gly Leu Cys Gly Asn Phe Asp Gly Ile Gln Asn Asn Asp Leu Thr
            995                 1000                1005 agc agc aac ctc caa gtg gag gaa gac cct gtg gac ttt ggg aac         3069
Ser Ser Asn Leu Gln Val Glu Glu Asp Pro Val Asp Phe Gly Asn
1010                1015                1020 tcc tgg aaa gtg agc tcg cag tgt gct gac acc aga aaa gtg cct         3114
Ser Trp Lys Val Ser Ser Gln Cys Ala Asp Thr Arg Lys Val Pro
    1025                1030                1035 ctg gac tca tcc cct gcc acc tgc cat aac aac atc atg aag cag         3159
Leu Asp Ser Ser Pro Ala Thr Cys His Asn Asn Ile Met Lys Gln
1040                1045                1050 acg atg gtg gat tcc tcc tgt aga atc ctt acc agt gac gtc ttc         3204
Thr Met Val Asp Ser Ser Cys Arg Ile Leu Thr Ser Asp Val Phe
    1055                1060                1065 cag gac tgc aac aag ctg gtg gac ccc gag cca tat ctg gat gtc         3249
Gln Asp Cys Asn Lys Leu Val Asp Pro Glu Pro Tyr Leu Asp Val
1070                1075                1080 tgc att tac gac acc tgc tcc tgt gag tcc att ggg gac tgc gcc         3294
Cys Ile Tyr Asp Thr Cys Ser Cys Glu Ser Ile Gly Asp Cys Ala
    1085                1090                1095 tgc ttc tgc gac acc att gct gcc tat gcc cac gtg tgt gcc cag         3339
Cys Phe Cys Asp Thr Ile Ala Ala Tyr Ala His Val Cys Ala Gln
1100                1105                1110 cat ggc aag gtg gtg acc tgg agg acg gcc aca ttg tgc ccc cag         3384
His Gly Lys Val Val Thr Trp Arg Thr Ala Thr Leu Cys Pro Gln
    1115                1120                1125 agc tgc gag gag agg aat ctc cgg gag aac ggg tat gag tgt gag         3429
Ser Cys Glu Glu Arg Asn Leu Arg Glu Asn Gly Tyr Glu Cys Glu
1130                1135                1140 tgg cgc tat aac agc tgt gca cct gcc tgt caa gtc acg tgt cag         3474
Trp Arg Tyr Asn Ser Cys Ala Pro Ala Cys Gln Val Thr Cys Gln
    1145                1150                1155 cac cct gag cca ctg gcc tgc cct gtg cag tgt gtg gag ggc tgc         3519
His Pro Glu Pro Leu Ala Cys Pro Val Gln Cys Val Glu Gly Cys
1160                1165                1170 cat gcc cac tgc cct cca ggg aaa atc ctg gat gag ctt ttg cag         3564
His Ala His Cys Pro Pro Gly Lys Ile Leu Asp Glu Leu Leu Gln
    1175                1180                1185 acc tgc gtt gac cct gaa gac tgt cca gtg tgt gag gtg gct ggc         3609
Thr Cys Val Asp Pro Glu Asp Cys Pro Val Cys Glu Val Ala Gly
1190                1195                1200 cgg cgt ttt gcc tca gga aag aaa gtc acc ttg aat ccc agt gac         3654
Arg Arg Phe Ala Ser Gly Lys Lys Val Thr Leu Asn Pro Ser Asp
    1205                1210                1215 cct gag cac tgc cag att tgc cac tgt gat gtt gtc aac ctc acc         3699
Pro Glu His Cys Gln Ile Cys His Cys Asp Val Val Asn Leu Thr
1220                1225                1230
```

```
                                              -continued tgt gaa gcc tgc cag gag ccg gga ggc ctg gtg gtg cct ccc aca      3744
Cys Glu Ala Cys Gln Glu Pro Gly Gly Leu Val Val Pro Pro Thr
1235              1240                 1245 gat gcc ccg gtg agc ccc acc act ctg tat gtg gag gac atc tcg      3789
Asp Ala Pro Val Ser Pro Thr Thr Leu Tyr Val Glu Asp Ile Ser
   1250              1255                 1260 gaa ccg ccg ttg cac gat ttc tac tgc agc agg cta ctg gac ctg      3834
Glu Pro Pro Leu His Asp Phe Tyr Cys Ser Arg Leu Leu Asp Leu
1265              1270                 1275 gtc ttc ctg ctg gat ggc tcc tcc agg ctg tcc gag gct gag ttt      3879
Val Phe Leu Leu Asp Gly Ser Ser Arg Leu Ser Glu Ala Glu Phe
   1280              1285                 1290 gaa gtg ctg aag gcc ttt gtg gtg gac atg atg gag cgg ctg cgc      3924
Glu Val Leu Lys Ala Phe Val Val Asp Met Met Glu Arg Leu Arg
1295              1300                 1305 atc tcc cag aag tgg gtc cgc gtg gcc gtg gtg gag tac cac gac      3969
Ile Ser Gln Lys Trp Val Arg Val Ala Val Val Glu Tyr His Asp
   1310              1315                 1320 ggc tcc cac gcc tac atc ggg ctc aag gac cgg aag cga ccg tca      4014
Gly Ser His Ala Tyr Ile Gly Leu Lys Asp Arg Lys Arg Pro Ser
1325              1330                 1335 gag ctg cgg cgc att gcc agc cag gtg aag tat gcg ggc agc cag      4059
Glu Leu Arg Arg Ile Ala Ser Gln Val Lys Tyr Ala Gly Ser Gln
   1340              1345                 1350 gtg gcc tcc acc agc gag gtc ttg aaa tac aca ctg ttc caa atc      4104
Val Ala Ser Thr Ser Glu Val Leu Lys Tyr Thr Leu Phe Gln Ile
1355              1360                 1365 ttc agc aag atc gac cgc cct gaa gcc tcc cgc atc gcc ctg ctc      4149
Phe Ser Lys Ile Asp Arg Pro Glu Ala Ser Arg Ile Ala Leu Leu
   1370              1375                 1380 ctg atg gcc agc cag gag ccc caa cgg atg tcc cgg aac ttt gtc      4194
Leu Met Ala Ser Gln Glu Pro Gln Arg Met Ser Arg Asn Phe Val
1385              1390                 1395 cgc tac gtc cag ggc ctg aag aag aag aag gtc att gtg atc ccg      4239
Arg Tyr Val Gln Gly Leu Lys Lys Lys Lys Val Ile Val Ile Pro
   1400              1405                 1410 gtg ggc att ggg ccc cat gcc aac ctc aag cag atc cgc ctc atc      4284
Val Gly Ile Gly Pro His Ala Asn Leu Lys Gln Ile Arg Leu Ile
1415              1420                 1425 gag aag cag gcc cct gag aac aag gcc ttc gtg ctg agc agt gtg      4329
Glu Lys Gln Ala Pro Glu Asn Lys Ala Phe Val Leu Ser Ser Val
   1430              1435                 1440 gat gag ctg gag cag caa agg gac gag atc gtt agc tac ctc tgt      4374
Asp Glu Leu Glu Gln Gln Arg Asp Glu Ile Val Ser Tyr Leu Cys
1445              1450                 1455 gac ctt gcc cct gaa gcc cct cct cct act ctg ccc ccc cac atg      4419
Asp Leu Ala Pro Glu Ala Pro Pro Pro Thr Leu Pro Pro His Met
   1460              1465                 1470 gca caa gtc act gtg ggc ccg ggg ctc ttg ggg gtt tcg acc ctg      4464
Ala Gln Val Thr Val Gly Pro Gly Leu Leu Gly Val Ser Thr Leu
1475              1480                 1485 ggg ccc aag agg aac tcc atg gtt ctg gat gtg gcg ttc gtc ctg      4509
Gly Pro Lys Arg Asn Ser Met Val Leu Asp Val Ala Phe Val Leu
   1490              1495                 1500 gaa gga tcg gac aaa att ggt gaa gcc gac ttc aac agg agc aag      4554
Glu Gly Ser Asp Lys Ile Gly Glu Ala Asp Phe Asn Arg Ser Lys
1505              1510                 1515 gag ttc atg gag gag gtg att cag cgg atg gat gtg ggc cag gac      4599
Glu Phe Met Glu Glu Val Ile Gln Arg Met Asp Val Gly Gln Asp
```

```
                                -continued
         1520                1525                1530
agc atc cac gtc acg gtg ctg cag tac tcc tac atg gtg acc gtg    4644
Ser Ile His Val Thr Val Leu Gln Tyr Ser Tyr Met Val Thr Val
    1535                1540                1545 gag tac ccc ttc agc gag gca cag tcc aaa ggg gac atc ctg cag    4689
Glu Tyr Pro Phe Ser Glu Ala Gln Ser Lys Gly Asp Ile Leu Gln
    1550                1555                1560 cgg gtg cga gag atc cgc tac cag ggc ggc aac agg acc aac act    4734
Arg Val Arg Glu Ile Arg Tyr Gln Gly Gly Asn Arg Thr Asn Thr
    1565                1570                1575 ggg ctg gcc ctg cgg tac ctc tct gac cac agc ttc ttg gtc agc    4779
Gly Leu Ala Leu Arg Tyr Leu Ser Asp His Ser Phe Leu Val Ser
    1580                1585                1590 cag ggt gac cgg gag cag gcg ccc aac ctg gtc tac atg gtc acc    4824
Gln Gly Asp Arg Glu Gln Ala Pro Asn Leu Val Tyr Met Val Thr
    1595                1600                1605 gga aat cct gcc tct gat gag atc aag agg ctg cct gga gac atc    4869
Gly Asn Pro Ala Ser Asp Glu Ile Lys Arg Leu Pro Gly Asp Ile
    1610                1615                1620 cag gtg gtg ccc att gga gtg ggc cct aat gcc aac gtg cag gag    4914
Gln Val Val Pro Ile Gly Val Gly Pro Asn Ala Asn Val Gln Glu
    1625                1630                1635 ctg gag agg att ggc tgg ccc aat gcc cct atc ctc atc cag gac    4959
Leu Glu Arg Ile Gly Trp Pro Asn Ala Pro Ile Leu Ile Gln Asp
    1640                1645                1650 ttt gag acg ctc ccc cga gag gct cct gac ctg gtg ctg cag agg    5004
Phe Glu Thr Leu Pro Arg Glu Ala Pro Asp Leu Val Leu Gln Arg
    1655                1660                1665 tgc tgc tcc gga gag ggg ctg cag atc ccc acc ctc tcc cct gca    5049
Cys Cys Ser Gly Glu Gly Leu Gln Ile Pro Thr Leu Ser Pro Ala
    1670                1675                1680 cct gac tgc agc cag ccc ctg gac gtg atc ctt ctc ctg gat ggc    5094
Pro Asp Cys Ser Gln Pro Leu Asp Val Ile Leu Leu Leu Asp Gly
    1685                1690                1695 tcc tcc agt ttc cca gct tct tat ttt gat gaa atg aag agt ttc    5139
Ser Ser Ser Phe Pro Ala Ser Tyr Phe Asp Glu Met Lys Ser Phe
    1700                1705                1710 gcc aag gct ttc att tca aaa gcc aat ata ggg cct cgt ctc act    5184
Ala Lys Ala Phe Ile Ser Lys Ala Asn Ile Gly Pro Arg Leu Thr
    1715                1720                1725 cag gtg tca gtg ctg cag tat gga agc atc acc acc att gac gtg    5229
Gln Val Ser Val Leu Gln Tyr Gly Ser Ile Thr Thr Ile Asp Val
    1730                1735                1740 cca tgg aac gtg gtc ccg gag aaa gcc cat ttg ctg agc ctt gtg    5274
Pro Trp Asn Val Val Pro Glu Lys Ala His Leu Leu Ser Leu Val
    1745                1750                1755 gac gtc atg cag cgg gag gga ggc ccc agc caa atc ggg gat gcc    5319
Asp Val Met Gln Arg Glu Gly Gly Pro Ser Gln Ile Gly Asp Ala
    1760                1765                1770 ttg ggc ttt gct gtg cga tac ttg act tca gaa atg cat ggg gcg    5364
Leu Gly Phe Ala Val Arg Tyr Leu Thr Ser Glu Met His Gly Ala
    1775                1780                1785 cgc ccg gga gcc tca aag gcg gtg gtc atc ctg gtc acg gac gtc    5409
Arg Pro Gly Ala Ser Lys Ala Val Val Ile Leu Val Thr Asp Val
    1790                1795                1800 tct gtg gat tca gtg gat gca gca gct gat gcc gcc agg tcc aac    5454
Ser Val Asp Ser Val Asp Ala Ala Ala Asp Ala Ala Arg Ser Asn
    1805                1810                1815 aga gtg aca gtg ttc cct att gga att gga gat cgc tac gat gca    5499
```

|  |  |  |  |  |  |  |  |  |  |  |  |  |
|---|---|---|---|---|---|---|---|---|---|---|---|---|
| Arg | Val | Thr | Val | Phe | Pro | Ile | Gly | Ile | Gly | Asp | Arg | Tyr | Asp | Ala |
|  | 1820 |  |  |  | 1825 |  |  |  | 1830 |  |  |  |

```
gcc cag cta cgg atc ttg gca ggc cca gca ggc gac tcc aac gtg    5544
Ala Gln Leu Arg Ile Leu Ala Gly Pro Ala Gly Asp Ser Asn Val
    1835                1840                1845 gtg aag ctc cag cga atc gaa gac ctc cct acc atg gtc acc ttg    5589
Val Lys Leu Gln Arg Ile Glu Asp Leu Pro Thr Met Val Thr Leu
1850                1855                1860 ggc aat tcc ttc ctc cac aaa ctg tgc tct gga ttt gtt agg att    5634
Gly Asn Ser Phe Leu His Lys Leu Cys Ser Gly Phe Val Arg Ile
    1865                1870                1875 tgc atg gat gag gat ggg aat gag aag agg ccc ggg gac gtc tgg    5679
Cys Met Asp Glu Asp Gly Asn Glu Lys Arg Pro Gly Asp Val Trp
    1880                1885                1890 acc ttg cca gac cag tgc cac acc gtg act tgc cag cca gat ggc    5724
Thr Leu Pro Asp Gln Cys His Thr Val Thr Cys Gln Pro Asp Gly
    1895                1900                1905 cag acc ttg ctg aag agt cat cgg gtc aac tgt gac cgg ggg ctg    5769
Gln Thr Leu Leu Lys Ser His Arg Val Asn Cys Asp Arg Gly Leu
    1910                1915                1920 agg cct tcg tgc cct aac agc cag tcc cct gtt aaa gtg gaa gag    5814
Arg Pro Ser Cys Pro Asn Ser Gln Ser Pro Val Lys Val Glu Glu
    1925                1930                1935 acc tgt ggc tgc cgc tgg acc tgc ccc tgc gtg tgc aca ggc agc    5859
Thr Cys Gly Cys Arg Trp Thr Cys Pro Cys Val Cys Thr Gly Ser
    1940                1945                1950 tcc act cgg cac atc gtg acc ttt gat ggg cag aat ttc aag ctg    5904
Ser Thr Arg His Ile Val Thr Phe Asp Gly Gln Asn Phe Lys Leu
    1955                1960                1965 act ggc agc tgt tct tat gtc cta ttt caa aac aag gag cag gac    5949
Thr Gly Ser Cys Ser Tyr Val Leu Phe Gln Asn Lys Glu Gln Asp
    1970                1975                1980 ctg gag gtg att ctc cat aat ggt gcc tgc agc cct gga gca agg    5994
Leu Glu Val Ile Leu His Asn Gly Ala Cys Ser Pro Gly Ala Arg
    1985                1990                1995 cag ggc tgc atg aaa tcc atc gag gtg aag cac agt gcc ctc tcc    6039
Gln Gly Cys Met Lys Ser Ile Glu Val Lys His Ser Ala Leu Ser
    2000                2005                2010 gtc gag ctg cac agt gac atg gag gtg acg gtg aat ggg aga ctg    6084
Val Glu Leu His Ser Asp Met Glu Val Thr Val Asn Gly Arg Leu
    2015                2020                2025 gtc tct gtt cct tac gtg ggt ggg aac atg gaa gtc aac gtt tat    6129
Val Ser Val Pro Tyr Val Gly Gly Asn Met Glu Val Asn Val Tyr
    2030                2035                2040 ggt gcc atc atg cat gag gtc aga ttc aat cac ctt ggt cac atc    6174
Gly Ala Ile Met His Glu Val Arg Phe Asn His Leu Gly His Ile
    2045                2050                2055 ttc aca ttc act cca caa aac aat gag ttc caa ctg cag ctc agc    6219
Phe Thr Phe Thr Pro Gln Asn Asn Glu Phe Gln Leu Gln Leu Ser
    2060                2065                2070 ccc aag act ttt gct tca aag acg tat ggt ctg tgt ggg atc tgt    6264
Pro Lys Thr Phe Ala Ser Lys Thr Tyr Gly Leu Cys Gly Ile Cys
    2075                2080                2085 gat gag aac gga gcc aat gac ttc atg ctg agg gat ggc aca gtc    6309
Asp Glu Asn Gly Ala Asn Asp Phe Met Leu Arg Asp Gly Thr Val
    2090                2095                2100 acc aca gac tgg aaa aca ctt gtt cag gaa tgg act gtg cag cgg    6354
Thr Thr Asp Trp Lys Thr Leu Val Gln Glu Trp Thr Val Gln Arg
    2105                2110                2115
```

| | | | | | | | | | | |
|---|---|---|---|---|---|---|---|---|---|---|
| cca | ggg | cag | acg | tgc | cag | ccc | atc | ctg | gag | gag | cag | tgt | ctt | gtc | 6399 |
| Pro | Gly | Gln | Thr | Cys | Gln | Pro | Ile | Leu | Glu | Glu | Gln | Cys | Leu | Val | |
| | 2120 | | | | 2125 | | | | | 2130 | | | | | |

| ccc | gac | agc | tcc | cac | tgc | cag | gtc | ctc | ctc | tta | cca | ctg | ttt | gct | 6444 |
|---|---|---|---|---|---|---|---|---|---|---|---|---|---|---|---|
| Pro | Asp | Ser | Ser | His | Cys | Gln | Val | Leu | Leu | Leu | Pro | Leu | Phe | Ala | |
| | 2135 | | | | 2140 | | | | | 2145 | | | | | |

| gaa | tgc | cac | aag | gtc | ctg | gct | cca | gcc | aca | ttc | tat | gcc | atc | tgc | 6489 |
|---|---|---|---|---|---|---|---|---|---|---|---|---|---|---|---|
| Glu | Cys | His | Lys | Val | Leu | Ala | Pro | Ala | Thr | Phe | Tyr | Ala | Ile | Cys | |
| | 2150 | | | | 2155 | | | | | 2160 | | | | | |

| cag | cag | gac | agt | tgc | cac | cag | gag | caa | gtg | tgt | gag | gtg | atc | gcc | 6534 |
|---|---|---|---|---|---|---|---|---|---|---|---|---|---|---|---|
| Gln | Gln | Asp | Ser | Cys | His | Gln | Glu | Gln | Val | Cys | Glu | Val | Ile | Ala | |
| | 2165 | | | | 2170 | | | | | 2175 | | | | | |

| tct | tat | gcc | cac | ctc | tgt | cgg | acc | aac | ggg | gtc | tgc | gtt | gac | tgg | 6579 |
|---|---|---|---|---|---|---|---|---|---|---|---|---|---|---|---|
| Ser | Tyr | Ala | His | Leu | Cys | Arg | Thr | Asn | Gly | Val | Cys | Val | Asp | Trp | |
| | 2180 | | | | 2185 | | | | | 2190 | | | | | |

| agg | aca | cct | gat | ttc | tgt | gct | atg | tca | tgc | cca | cca | tct | ctg | gtt | 6624 |
|---|---|---|---|---|---|---|---|---|---|---|---|---|---|---|---|
| Arg | Thr | Pro | Asp | Phe | Cys | Ala | Met | Ser | Cys | Pro | Pro | Ser | Leu | Val | |
| | 2195 | | | | 2200 | | | | | 2205 | | | | | |

| tat | aac | cac | tgt | gag | cat | ggc | tgt | ccc | cgg | cac | tgt | gat | ggc | aac | 6669 |
|---|---|---|---|---|---|---|---|---|---|---|---|---|---|---|---|
| Tyr | Asn | His | Cys | Glu | His | Gly | Cys | Pro | Arg | His | Cys | Asp | Gly | Asn | |
| | 2210 | | | | 2215 | | | | | 2220 | | | | | |

| gtg | agc | tcc | tgt | ggg | gac | cat | ccc | tcc | gaa | ggc | tgt | ttc | tgc | cct | 6714 |
|---|---|---|---|---|---|---|---|---|---|---|---|---|---|---|---|
| Val | Ser | Ser | Cys | Gly | Asp | His | Pro | Ser | Glu | Gly | Cys | Phe | Cys | Pro | |
| | 2225 | | | | 2230 | | | | | 2235 | | | | | |

| cca | gat | aaa | gtc | atg | ttg | gaa | ggc | agc | tgt | gtc | cct | gaa | gag | gcc | 6759 |
|---|---|---|---|---|---|---|---|---|---|---|---|---|---|---|---|
| Pro | Asp | Lys | Val | Met | Leu | Glu | Gly | Ser | Cys | Val | Pro | Glu | Glu | Ala | |
| | 2240 | | | | 2245 | | | | | 2250 | | | | | |

| tgc | act | cag | tgc | att | ggt | gag | gat | gga | gtc | cag | cac | cag | ttc | ctg | 6804 |
|---|---|---|---|---|---|---|---|---|---|---|---|---|---|---|---|
| Cys | Thr | Gln | Cys | Ile | Gly | Glu | Asp | Gly | Val | Gln | His | Gln | Phe | Leu | |
| | 2255 | | | | 2260 | | | | | 2265 | | | | | |

| gaa | gcc | tgg | gtc | ccg | gac | cac | cag | ccc | tgt | cag | atc | tgc | aca | tgc | 6849 |
|---|---|---|---|---|---|---|---|---|---|---|---|---|---|---|---|
| Glu | Ala | Trp | Val | Pro | Asp | His | Gln | Pro | Cys | Gln | Ile | Cys | Thr | Cys | |
| | 2270 | | | | 2275 | | | | | 2280 | | | | | |

| ctc | agc | ggg | cgg | aag | gtc | aac | tgc | aca | acg | cag | ccc | tgc | ccc | acg | 6894 |
|---|---|---|---|---|---|---|---|---|---|---|---|---|---|---|---|
| Leu | Ser | Gly | Arg | Lys | Val | Asn | Cys | Thr | Thr | Gln | Pro | Cys | Pro | Thr | |
| | 2285 | | | | 2290 | | | | | 2295 | | | | | |

| gcc | aaa | gct | ccc | acg | tgt | ggc | ctg | tgt | gaa | gta | gcc | cgc | ctc | cgc | 6939 |
|---|---|---|---|---|---|---|---|---|---|---|---|---|---|---|---|
| Ala | Lys | Ala | Pro | Thr | Cys | Gly | Leu | Cys | Glu | Val | Ala | Arg | Leu | Arg | |
| | 2300 | | | | 2305 | | | | | 2310 | | | | | |

| cag | aat | gca | gac | cag | tgc | tgc | ccc | gag | tat | gag | tgt | gtg | tgt | gac | 6984 |
|---|---|---|---|---|---|---|---|---|---|---|---|---|---|---|---|
| Gln | Asn | Ala | Asp | Gln | Cys | Cys | Pro | Glu | Tyr | Glu | Cys | Val | Cys | Asp | |
| | 2315 | | | | 2320 | | | | | 2325 | | | | | |

| cca | gtg | agc | tgt | gac | ctg | ccc | cca | gtg | cct | cac | tgt | gaa | cgt | ggc | 7029 |
|---|---|---|---|---|---|---|---|---|---|---|---|---|---|---|---|
| Pro | Val | Ser | Cys | Asp | Leu | Pro | Pro | Val | Pro | His | Cys | Glu | Arg | Gly | |
| | 2330 | | | | 2335 | | | | | 2340 | | | | | |

| ctc | cag | ccc | aca | ctg | acc | aac | cct | ggc | gag | tgc | aga | ccc | aac | ttc | 7074 |
|---|---|---|---|---|---|---|---|---|---|---|---|---|---|---|---|
| Leu | Gln | Pro | Thr | Leu | Thr | Asn | Pro | Gly | Glu | Cys | Arg | Pro | Asn | Phe | |
| | 2345 | | | | 2350 | | | | | 2355 | | | | | |

| acc | tgc | gcc | tgc | agg | aag | gag | gag | tgc | aaa | aga | gtg | tcc | cca | ccc | 7119 |
|---|---|---|---|---|---|---|---|---|---|---|---|---|---|---|---|
| Thr | Cys | Ala | Cys | Arg | Lys | Glu | Glu | Cys | Lys | Arg | Val | Ser | Pro | Pro | |
| | 2360 | | | | 2365 | | | | | 2370 | | | | | |

| tcc | tgc | ccc | ccg | cac | cgt | ttg | ccc | acc | ctt | cgg | aag | acc | cag | tgc | 7164 |
|---|---|---|---|---|---|---|---|---|---|---|---|---|---|---|---|
| Ser | Cys | Pro | Pro | His | Arg | Leu | Pro | Thr | Leu | Arg | Lys | Thr | Gln | Cys | |
| | 2375 | | | | 2380 | | | | | 2385 | | | | | |

| tgt | gat | gag | tat | gag | tgt | gcc | tgc | aac | tgt | gtc | aac | tcc | aca | gtg | 7209 |
|---|---|---|---|---|---|---|---|---|---|---|---|---|---|---|---|
| Cys | Asp | Glu | Tyr | Glu | Cys | Ala | Cys | Asn | Cys | Val | Asn | Ser | Thr | Val | |
| | 2390 | | | | 2395 | | | | | 2400 | | | | | |

| agc | tgt | ccc | ctt | ggg | tac | ttg | gcc | tca | acc | gcc | acc | aat | gac | tgt | 7254 |
|---|---|---|---|---|---|---|---|---|---|---|---|---|---|---|---|
| Ser | Cys | Pro | Leu | Gly | Tyr | Leu | Ala | Ser | Thr | Ala | Thr | Asn | Asp | Cys | |
| | 2405 | | | | 2410 | | | | | 2415 | | | | | |

-continued

```
ggc tgt acc aca acc acc tgc ctt ccc gac aag gtg tgt gtc cac    7299
Gly Cys Thr Thr Thr Thr Cys Leu Pro Asp Lys Val Cys Val His
    2420                2425                2430 cga agc acc atc tac cct gtg ggc cag ttc tgg gag gag ggc tgc    7344
Arg Ser Thr Ile Tyr Pro Val Gly Gln Phe Trp Glu Glu Gly Cys
    2435                2440                2445 gat gtg tgc acc tgc acc gac atg gag gat gcc gtg atg ggc ctc    7389
Asp Val Cys Thr Cys Thr Asp Met Glu Asp Ala Val Met Gly Leu
    2450                2455                2460 cgc gtg gcc cag tgc tcc cag aag ccc tgt gag gac agc tgt cgg    7434
Arg Val Ala Gln Cys Ser Gln Lys Pro Cys Glu Asp Ser Cys Arg
    2465                2470                2475 tcg ggc ttc act tac gtt ctg cat gaa ggc gag tgc tgt gga agg    7479
Ser Gly Phe Thr Tyr Val Leu His Glu Gly Glu Cys Cys Gly Arg
    2480                2485                2490 tgc ctg cca tct gcc tgt gag gtg gtg act ggc tca ccg cgg ggg    7524
Cys Leu Pro Ser Ala Cys Glu Val Val Thr Gly Ser Pro Arg Gly
    2495                2500                2505 gac tcc cag tct tcc tgg aag agt gtc ggc tcc cag tgg gcc tcc    7569
Asp Ser Gln Ser Ser Trp Lys Ser Val Gly Ser Gln Trp Ala Ser
    2510                2515                2520 ccg gag aac ccc tgc ctc atc aat gag tgt gtc cga gtg aag gag    7614
Pro Glu Asn Pro Cys Leu Ile Asn Glu Cys Val Arg Val Lys Glu
    2525                2530                2535 gag gtc ttt ata caa caa agg aac gtc tcc tgc ccc cag ctg gag    7659
Glu Val Phe Ile Gln Gln Arg Asn Val Ser Cys Pro Gln Leu Glu
    2540                2545                2550 gtc cct gtc tgc ccc tcg ggc ttt cag ctg agc tgt aag acc tca    7704
Val Pro Val Cys Pro Ser Gly Phe Gln Leu Ser Cys Lys Thr Ser
    2555                2560                2565 gcg tgc tgc cca agc tgt cgc tgt gag cgc atg gag gcc tgc atg    7749
Ala Cys Cys Pro Ser Cys Arg Cys Glu Arg Met Glu Ala Cys Met
    2570                2575                2580 ctc aat ggc act gtc att ggg ccc ggg aag act gtg atg atc gat    7794
Leu Asn Gly Thr Val Ile Gly Pro Gly Lys Thr Val Met Ile Asp
    2585                2590                2595 gtg tgc acg acc tgc cgc tgc atg gtg cag gtg ggg gtc atc tct    7839
Val Cys Thr Thr Cys Arg Cys Met Val Gln Val Gly Val Ile Ser
    2600                2605                2610 gga ttc aag ctg gag tgc agg aag acc acc tgc aac ccc tgc ccc    7884
Gly Phe Lys Leu Glu Cys Arg Lys Thr Thr Cys Asn Pro Cys Pro
    2615                2620                2625 ctg ggt tac aag gaa gaa aat aac aca ggt gaa tgt tgt ggg aga    7929
Leu Gly Tyr Lys Glu Glu Asn Asn Thr Gly Glu Cys Cys Gly Arg
    2630                2635                2640 tgt ttg cct acg gct tgc acc att cag cta aga gga gga cag atc    7974
Cys Leu Pro Thr Ala Cys Thr Ile Gln Leu Arg Gly Gly Gln Ile
    2645                2650                2655 atg aca ctg aag cgt gat gag acg ctc cag gat ggc tgt gat act    8019
Met Thr Leu Lys Arg Asp Glu Thr Leu Gln Asp Gly Cys Asp Thr
    2660                2665                2670 cac ttc tgc aag gtc aat gag aga gga gag tac ttc tgg gag aag    8064
His Phe Cys Lys Val Asn Glu Arg Gly Glu Tyr Phe Trp Glu Lys
    2675                2680                2685 agg gtc aca ggc tgc cca ccc ttt gat gaa cac aag tgt ctg gct    8109
Arg Val Thr Gly Cys Pro Pro Phe Asp Glu His Lys Cys Leu Ala
    2690                2695                2700 gag gga ggt aaa att atg aaa att cca ggc acc tgc tgt gac aca    8154
Glu Gly Gly Lys Ile Met Lys Ile Pro Gly Thr Cys Cys Asp Thr
```

```
                    2705                2710                2715
tgt  gag  gag  cct  gag  tgc  aac  gac  atc  act  gcc  agg  ctg  cag  tat      8199
Cys  Glu  Glu  Pro  Glu  Cys  Asn  Asp  Ile  Thr  Ala  Arg  Leu  Gln  Tyr
2720                2725                2730 gtc  aag  gtg  gga  agc  tgt  aag  tct  gaa  gta  gag  gtg  gat  atc  cac      8244
Val  Lys  Val  Gly  Ser  Cys  Lys  Ser  Glu  Val  Glu  Val  Asp  Ile  His
2735                2740                2745 tac  tgc  cag  ggc  aaa  tgt  gcc  agc  aaa  gcc  atg  tac  tcc  att  gac      8289
Tyr  Cys  Gln  Gly  Lys  Cys  Ala  Ser  Lys  Ala  Met  Tyr  Ser  Ile  Asp
2750                2755                2760 atc  aac  gat  gtg  cag  gac  cag  tgc  tcc  tgc  tgc  tct  ccg  aca  cgg      8334
Ile  Asn  Asp  Val  Gln  Asp  Gln  Cys  Ser  Cys  Cys  Ser  Pro  Thr  Arg
2765                2770                2775 acg  gag  ccc  atg  cag  gtg  gcc  ctg  cac  tgc  acc  aat  ggc  tct  gtt      8379
Thr  Glu  Pro  Met  Gln  Val  Ala  Leu  His  Cys  Thr  Asn  Gly  Ser  Val
2780                2785                2790 gtg  tac  cat  gag  gtt  ctc  aat  gcc  atg  gag  tgc  aaa  tgc  tcc  ccc      8424
Val  Tyr  His  Glu  Val  Leu  Asn  Ala  Met  Glu  Cys  Lys  Cys  Ser  Pro
2795                2800                2805 agg  aag  tgc  agc  aag  tga                                                   8442
Arg  Lys  Cys  Ser  Lys
2810

<210> SEQ ID NO 4
<211> LENGTH: 2813
<212> TYPE: PRT
<213> ORGANISM: Homo sapiens

<400> SEQUENCE: 4

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220
```

```
Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
        290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
        450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
        530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640
```

-continued

```
Ala Trp Arg Glu Pro Gly Arg Cys Glu Leu Asn Cys Pro Lys Gly Gln
                645                 650                 655
Val Tyr Leu Gln Cys Gly Thr Pro Cys Asn Leu Thr Cys Arg Ser Leu
            660                 665                 670
Ser Tyr Pro Asp Glu Glu Cys Asn Glu Ala Cys Leu Glu Gly Cys Phe
        675                 680                 685
Cys Pro Pro Gly Leu Tyr Met Asp Glu Arg Gly Asp Cys Val Pro Lys
    690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Met Ser Gly Val Pro Gly Ser Leu Leu Pro Asp Ala Val
            740                 745                 750
Leu Ser Ser Pro Leu Ser His Arg Ser Lys Arg Ser Leu Ser Cys Arg
        755                 760                 765
Pro Pro Met Val Lys Leu Val Cys Pro Ala Asp Asn Leu Arg Ala Glu
    770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
                805                 810                 815
His Glu Asn Arg Cys Val Ala Leu Glu Arg Cys Pro Cys Phe His Gln
            820                 825                 830
Gly Lys Glu Tyr Ala Pro Gly Glu Thr Val Lys Ile Gly Cys Asn Thr
        835                 840                 845
Cys Val Cys Arg Asp Arg Lys Trp Asn Cys Thr Asp His Val Cys Asp
    850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Phe Arg Ile Leu Val Gly Asn Lys
            900                 905                 910
Gly Cys Ser His Pro Ser Val Lys Cys Lys Lys Arg Val Thr Ile Leu
        915                 920                 925
Val Glu Gly Gly Glu Ile Glu Leu Phe Asp Gly Glu Val Asn Val Lys
    930                 935                 940
Arg Pro Met Lys Asp Glu Thr His Phe Glu Val Val Glu Ser Gly Arg
945                 950                 955                 960
Tyr Ile Ile Leu Leu Leu Gly Lys Ala Leu Ser Val Val Trp Asp Arg
                965                 970                 975
His Leu Ser Ile Ser Val Val Leu Lys Gln Thr Tyr Gln Glu Lys Val
            980                 985                 990
Cys Gly Leu Cys Gly Asn Phe Asp  Gly Ile Gln Asn Asn  Asp Leu Thr
        995                 1000                1005
Ser Ser  Asn Leu Gln Val Glu  Glu Asp Pro Val Asp  Phe Gly Asn
    1010                1015                1020
Ser Trp Lys Val Ser Ser Gln  Cys Ala Asp Thr Arg  Lys Val Pro
    1025                1030                1035
Leu Asp Ser Ser Pro Ala Thr  Cys His Asn Asn Ile  Met Lys Gln
    1040                1045                1050
Thr Met Val Asp Ser Ser Cys  Arg Ile Leu Thr Ser  Asp Val Phe
```

-continued

```
            1055                1060                1065
Gln Asp Cys Asn Lys Leu Val Asp Pro Glu Pro Tyr Leu Asp Val
            1070                1075                1080

Cys Ile Tyr Asp Thr Cys Ser Cys Glu Ser Ile Gly Asp Cys Ala
            1085                1090                1095

Cys Phe Cys Asp Thr Ile Ala Ala Tyr Ala His Val Cys Ala Gln
            1100                1105                1110

His Gly Lys Val Val Thr Trp Arg Thr Ala Thr Leu Cys Pro Gln
            1115                1120                1125

Ser Cys Glu Glu Arg Asn Leu Arg Glu Asn Gly Tyr Glu Cys Glu
            1130                1135                1140

Trp Arg Tyr Asn Ser Cys Ala Pro Ala Cys Gln Val Thr Cys Gln
            1145                1150                1155

His Pro Glu Pro Leu Ala Cys Pro Val Gln Cys Val Glu Gly Cys
            1160                1165                1170

His Ala His Cys Pro Pro Gly Lys Ile Leu Asp Glu Leu Leu Gln
            1175                1180                1185

Thr Cys Val Asp Pro Glu Asp Cys Pro Val Cys Glu Val Ala Gly
            1190                1195                1200

Arg Arg Phe Ala Ser Gly Lys Lys Val Thr Leu Asn Pro Ser Asp
            1205                1210                1215

Pro Glu His Cys Gln Ile Cys His Cys Asp Val Val Asn Leu Thr
            1220                1225                1230

Cys Glu Ala Cys Gln Glu Pro Gly Gly Leu Val Val Pro Pro Thr
            1235                1240                1245

Asp Ala Pro Val Ser Pro Thr Thr Leu Tyr Val Glu Asp Ile Ser
            1250                1255                1260

Glu Pro Pro Leu His Asp Phe Tyr Cys Ser Arg Leu Leu Asp Leu
            1265                1270                1275

Val Phe Leu Leu Asp Gly Ser Ser Arg Leu Ser Glu Ala Glu Phe
            1280                1285                1290

Glu Val Leu Lys Ala Phe Val Val Asp Met Met Glu Arg Leu Arg
            1295                1300                1305

Ile Ser Gln Lys Trp Val Arg Val Ala Val Val Glu Tyr His Asp
            1310                1315                1320

Gly Ser His Ala Tyr Ile Gly Leu Lys Asp Arg Lys Arg Pro Ser
            1325                1330                1335

Glu Leu Arg Arg Ile Ala Ser Gln Val Lys Tyr Ala Gly Ser Gln
            1340                1345                1350

Val Ala Ser Thr Ser Glu Val Leu Lys Tyr Thr Leu Phe Gln Ile
            1355                1360                1365

Phe Ser Lys Ile Asp Arg Pro Glu Ala Ser Arg Ile Ala Leu Leu
            1370                1375                1380

Leu Met Ala Ser Gln Glu Pro Gln Arg Met Ser Arg Asn Phe Val
            1385                1390                1395

Arg Tyr Val Gln Gly Leu Lys Lys Lys Lys Val Ile Val Ile Pro
            1400                1405                1410

Val Gly Ile Gly Pro His Ala Asn Leu Lys Gln Ile Arg Leu Ile
            1415                1420                1425

Glu Lys Gln Ala Pro Glu Asn Lys Ala Phe Val Leu Ser Ser Val
            1430                1435                1440

Asp Glu Leu Glu Gln Gln Arg Asp Glu Ile Val Ser Tyr Leu Cys
            1445                1450                1455
```

```
Asp Leu Ala Pro Glu Ala Pro Pro Thr Leu Pro Pro His Met
1460            1465            1470

Ala Gln Val Thr Val Gly Pro Gly Leu Leu Gly Val Ser Thr Leu
1475            1480            1485

Gly Pro Lys Arg Asn Ser Met Val Leu Asp Val Ala Phe Val Leu
1490            1495            1500

Glu Gly Ser Asp Lys Ile Gly Glu Ala Asp Phe Asn Arg Ser Lys
1505            1510            1515

Glu Phe Met Glu Glu Val Ile Gln Arg Met Asp Val Gly Gln Asp
1520            1525            1530

Ser Ile His Val Thr Val Leu Gln Tyr Ser Tyr Met Val Thr Val
1535            1540            1545

Glu Tyr Pro Phe Ser Glu Ala Gln Ser Lys Gly Asp Ile Leu Gln
1550            1555            1560

Arg Val Arg Glu Ile Arg Tyr Gln Gly Gly Asn Arg Thr Asn Thr
1565            1570            1575

Gly Leu Ala Leu Arg Tyr Leu Ser Asp His Ser Phe Leu Val Ser
1580            1585            1590

Gln Gly Asp Arg Glu Gln Ala Pro Asn Leu Val Tyr Met Val Thr
1595            1600            1605

Gly Asn Pro Ala Ser Asp Glu Ile Lys Arg Leu Pro Gly Asp Ile
1610            1615            1620

Gln Val Val Pro Ile Gly Val Gly Pro Asn Ala Asn Val Gln Glu
1625            1630            1635

Leu Glu Arg Ile Gly Trp Pro Asn Ala Pro Ile Leu Ile Gln Asp
1640            1645            1650

Phe Glu Thr Leu Pro Arg Glu Ala Pro Asp Leu Val Leu Gln Arg
1655            1660            1665

Cys Cys Ser Gly Glu Gly Leu Gln Ile Pro Thr Leu Ser Pro Ala
1670            1675            1680

Pro Asp Cys Ser Gln Pro Leu Asp Val Ile Leu Leu Leu Asp Gly
1685            1690            1695

Ser Ser Ser Phe Pro Ala Ser Tyr Phe Asp Glu Met Lys Ser Phe
1700            1705            1710

Ala Lys Ala Phe Ile Ser Lys Ala Asn Ile Gly Pro Arg Leu Thr
1715            1720            1725

Gln Val Ser Val Leu Gln Tyr Gly Ser Ile Thr Thr Ile Asp Val
1730            1735            1740

Pro Trp Asn Val Val Pro Glu Lys Ala His Leu Leu Ser Leu Val
1745            1750            1755

Asp Val Met Gln Arg Glu Gly Gly Pro Ser Gln Ile Gly Asp Ala
1760            1765            1770

Leu Gly Phe Ala Val Arg Tyr Leu Thr Ser Glu Met His Gly Ala
1775            1780            1785

Arg Pro Gly Ala Ser Lys Ala Val Val Ile Leu Val Thr Asp Val
1790            1795            1800

Ser Val Asp Ser Val Asp Ala Ala Ala Asp Ala Ala Arg Ser Asn
1805            1810            1815

Arg Val Thr Val Phe Pro Ile Gly Ile Gly Asp Arg Tyr Asp Ala
1820            1825            1830

Ala Gln Leu Arg Ile Leu Ala Gly Pro Ala Gly Asp Ser Asn Val
1835            1840            1845
```

```
Val Lys Leu Gln Arg Ile Glu Asp Leu Pro Thr Met Val Thr Leu
1850                1855                1860

Gly Asn Ser Phe Leu His Lys Leu Cys Ser Gly Phe Val Arg Ile
1865                1870                1875

Cys Met Asp Glu Asp Gly Asn Glu Lys Arg Pro Gly Asp Val Trp
1880                1885                1890

Thr Leu Pro Asp Gln Cys His Thr Val Thr Cys Gln Pro Asp Gly
1895                1900                1905

Gln Thr Leu Leu Lys Ser His Arg Val Asn Cys Asp Arg Gly Leu
1910                1915                1920

Arg Pro Ser Cys Pro Asn Ser Gln Ser Pro Val Lys Val Glu Glu
1925                1930                1935

Thr Cys Gly Cys Arg Trp Thr Cys Pro Cys Val Cys Thr Gly Ser
1940                1945                1950

Ser Thr Arg His Ile Val Thr Phe Asp Gly Gln Asn Phe Lys Leu
1955                1960                1965

Thr Gly Ser Cys Ser Tyr Val Leu Phe Gln Asn Lys Glu Gln Asp
1970                1975                1980

Leu Glu Val Ile Leu His Asn Gly Ala Cys Ser Pro Gly Ala Arg
1985                1990                1995

Gln Gly Cys Met Lys Ser Ile Glu Val Lys His Ser Ala Leu Ser
2000                2005                2010

Val Glu Leu His Ser Asp Met Glu Val Thr Val Asn Gly Arg Leu
2015                2020                2025

Val Ser Val Pro Tyr Val Gly Gly Asn Met Glu Val Asn Val Tyr
2030                2035                2040

Gly Ala Ile Met His Glu Val Arg Phe Asn His Leu Gly His Ile
2045                2050                2055

Phe Thr Phe Thr Pro Gln Asn Asn Glu Phe Gln Leu Gln Leu Ser
2060                2065                2070

Pro Lys Thr Phe Ala Ser Lys Thr Tyr Gly Leu Cys Gly Ile Cys
2075                2080                2085

Asp Glu Asn Gly Ala Asn Asp Phe Met Leu Arg Asp Gly Thr Val
2090                2095                2100

Thr Thr Asp Trp Lys Thr Leu Val Gln Glu Trp Thr Val Gln Arg
2105                2110                2115

Pro Gly Gln Thr Cys Gln Pro Ile Leu Glu Glu Gln Cys Leu Val
2120                2125                2130

Pro Asp Ser Ser His Cys Gln Val Leu Leu Leu Pro Leu Phe Ala
2135                2140                2145

Glu Cys His Lys Val Leu Ala Pro Ala Thr Phe Tyr Ala Ile Cys
2150                2155                2160

Gln Gln Asp Ser Cys His Gln Glu Gln Val Cys Glu Val Ile Ala
2165                2170                2175

Ser Tyr Ala His Leu Cys Arg Thr Asn Gly Val Cys Val Asp Trp
2180                2185                2190

Arg Thr Pro Asp Phe Cys Ala Met Ser Cys Pro Pro Ser Leu Val
2195                2200                2205

Tyr Asn His Cys Glu His Gly Cys Pro Arg His Cys Asp Gly Asn
2210                2215                2220

Val Ser Ser Cys Gly Asp His Pro Ser Glu Gly Cys Phe Cys Pro
2225                2230                2235

Pro Asp Lys Val Met Leu Glu Gly Ser Cys Val Pro Glu Glu Ala
```

-continued

|  | 2240 |  |  | 2245 |  |  |  | 2250 |  |  |
|---|---|---|---|---|---|---|---|---|---|---|

Cys Thr Gln Cys Ile Gly Glu Asp Gly Val Gln His Gln Phe Leu
2255          2260              2265

Glu Ala Trp Val Pro Asp His Gln Pro Cys Gln Ile Cys Thr Cys
2270          2275              2280

Leu Ser Gly Arg Lys Val Asn Cys Thr Thr Gln Pro Cys Pro Thr
2285          2290              2295

Ala Lys Ala Pro Thr Cys Gly Leu Cys Glu Val Ala Arg Leu Arg
2300          2305              2310

Gln Asn Ala Asp Gln Cys Cys Pro Glu Tyr Glu Cys Val Cys Asp
2315          2320              2325

Pro Val Ser Cys Asp Leu Pro Pro Val Pro His Cys Glu Arg Gly
2330          2335              2340

Leu Gln Pro Thr Leu Thr Asn Pro Gly Glu Cys Arg Pro Asn Phe
2345          2350              2355

Thr Cys Ala Cys Arg Lys Glu Glu Cys Lys Arg Val Ser Pro Pro
2360          2365              2370

Ser Cys Pro Pro His Arg Leu Pro Thr Leu Arg Lys Thr Gln Cys
2375          2380              2385

Cys Asp Glu Tyr Glu Cys Ala Cys Asn Cys Val Asn Ser Thr Val
2390          2395              2400

Ser Cys Pro Leu Gly Tyr Leu Ala Ser Thr Ala Thr Asn Asp Cys
2405          2410              2415

Gly Cys Thr Thr Thr Thr Cys Leu Pro Asp Lys Val Cys Val His
2420          2425              2430

Arg Ser Thr Ile Tyr Pro Val Gly Gln Phe Trp Glu Glu Gly Cys
2435          2440              2445

Asp Val Cys Thr Cys Thr Asp Met Glu Asp Ala Val Met Gly Leu
2450          2455              2460

Arg Val Ala Gln Cys Ser Gln Lys Pro Cys Glu Asp Ser Cys Arg
2465          2470              2475

Ser Gly Phe Thr Tyr Val Leu His Glu Gly Glu Cys Cys Gly Arg
2480          2485              2490

Cys Leu Pro Ser Ala Cys Glu Val Val Thr Gly Ser Pro Arg Gly
2495          2500              2505

Asp Ser Gln Ser Ser Trp Lys Ser Val Gly Ser Gln Trp Ala Ser
2510          2515              2520

Pro Glu Asn Pro Cys Leu Ile Asn Glu Cys Val Arg Val Lys Glu
2525          2530              2535

Glu Val Phe Ile Gln Gln Arg Asn Val Ser Cys Pro Gln Leu Glu
2540          2545              2550

Val Pro Val Cys Pro Ser Gly Phe Gln Leu Ser Cys Lys Thr Ser
2555          2560              2565

Ala Cys Cys Pro Ser Cys Arg Cys Glu Arg Met Glu Ala Cys Met
2570          2575              2580

Leu Asn Gly Thr Val Ile Gly Pro Gly Lys Thr Val Met Ile Asp
2585          2590              2595

Val Cys Thr Thr Cys Arg Cys Met Val Gln Val Gly Val Ile Ser
2600          2605              2610

Gly Phe Lys Leu Glu Cys Arg Lys Thr Thr Cys Asn Pro Cys Pro
2615          2620              2625

Leu Gly Tyr Lys Glu Glu Asn Asn Thr Gly Glu Cys Cys Gly Arg
2630          2635              2640

Cys Leu Pro Thr Ala Cys Thr Ile Gln Leu Arg Gly Gly Gln Ile
             2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 5
<211> LENGTH: 1444
<212> TYPE: PRT
<213> ORGANISM: Artificial Sequence
<220> FEATURE:
<223> OTHER INFORMATION: amino acid sequence of a single chain factor
      viii molecule

<400> SEQUENCE: 5

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu

```
                165                 170                 175
Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
                195                 200                 205

His Ser Glu Thr Lys Asn Ser Leu Met Gln Asp Arg Asp Ala Ala Ser
                210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
                290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
                370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
                450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
                515                 520                 525

Leu Thr Arg Tyr Tyr Ser Ser Phe Val Asn Met Glu Arg Asp Leu Ala
                530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590
```

```
Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                    645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                    725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Thr Thr Leu Gln
        755                 760                 765

Ser Asp Gln Glu Glu Ile Asp Tyr Asp Asp Thr Ile Ser Val Glu Met
        770                 775                 780

Lys Lys Glu Asp Phe Asp Ile Tyr Asp Glu Asp Asn Gln Ser Pro
785                 790                 795                 800

Arg Ser Phe Gln Lys Lys Thr Arg His Tyr Phe Ile Ala Ala Val Glu
                    805                 810                 815

Arg Leu Trp Asp Tyr Gly Met Ser Ser Ser Pro His Val Leu Arg Asn
                820                 825                 830

Arg Ala Gln Ser Gly Ser Val Pro Gln Phe Lys Lys Val Val Phe Gln
        835                 840                 845

Glu Phe Thr Asp Gly Ser Phe Thr Gln Pro Leu Tyr Arg Gly Glu Leu
        850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
                    885                 890                 895

Phe Tyr Ser Ser Leu Ile Ser Tyr Glu Glu Asp Gln Arg Gln Gly Ala
                900                 905                 910

Glu Pro Arg Lys Asn Phe Val Lys Pro Asn Glu Thr Lys Thr Tyr Phe
                915                 920                 925

Trp Lys Val Gln His His Met Ala Pro Thr Lys Asp Glu Phe Asp Cys
        930                 935                 940

Lys Ala Trp Ala Tyr Phe Ser Asp Val Asp Leu Glu Lys Asp Val His
945                 950                 955                 960

Ser Gly Leu Ile Gly Pro Leu Leu Val Cys His Thr Asn Thr Leu Asn
                    965                 970                 975

Pro Ala His Gly Arg Gln Val Thr Val Gln Glu Phe Ala Leu Phe Phe
                980                 985                 990

Thr Ile Phe Asp Glu Thr Lys Ser  Trp Tyr Phe Thr Glu  Asn Met Glu
                995                 1000                1005
```

```
Arg Asn Cys Arg Ala Pro Cys Asn Ile Gln Met Glu Asp Pro Thr
1010                1015                1020

Phe Lys Glu Asn Tyr Arg Phe His Ala Ile Asn Gly Tyr Ile Met
1025                1030                1035

Asp Thr Leu Pro Gly Leu Val Met Ala Gln Asp Gln Arg Ile Arg
1040                1045                1050

Trp Tyr Leu Leu Ser Met Gly Ser Asn Glu Asn Ile His Ser Ile
1055                1060                1065

His Phe Ser Gly His Val Phe Thr Val Arg Lys Lys Glu Glu Tyr
1070                1075                1080

Lys Met Ala Leu Tyr Asn Leu Tyr Pro Gly Val Phe Glu Thr Val
1085                1090                1095

Glu Met Leu Pro Ser Lys Ala Gly Ile Trp Arg Val Glu Cys Leu
1100                1105                1110

Ile Gly Glu His Leu His Ala Gly Met Ser Thr Leu Phe Leu Val
1115                1120                1125

Tyr Ser Asn Lys Cys Gln Thr Pro Leu Gly Met Ala Ser Gly His
1130                1135                1140

Ile Arg Asp Phe Gln Ile Thr Ala Ser Gly Gln Tyr Gly Gln Trp
1145                1150                1155

Ala Pro Lys Leu Ala Arg Leu His Tyr Ser Gly Ser Ile Asn Ala
1160                1165                1170

Trp Ser Thr Lys Glu Pro Phe Ser Trp Ile Lys Val Asp Leu Leu
1175                1180                1185

Ala Pro Met Ile Ile His Gly Ile Lys Thr Gln Gly Ala Arg Gln
1190                1195                1200

Lys Phe Ser Ser Leu Tyr Ile Ser Gln Phe Ile Ile Met Tyr Ser
1205                1210                1215

Leu Asp Gly Lys Lys Trp Gln Thr Tyr Arg Gly Asn Ser Thr Gly
1220                1225                1230

Thr Leu Met Val Phe Phe Gly Asn Val Asp Ser Ser Gly Ile Lys
1235                1240                1245

His Asn Ile Phe Asn Pro Pro Ile Ile Ala Arg Tyr Ile Arg Leu
1250                1255                1260

His Pro Thr His Tyr Ser Ile Arg Ser Thr Leu Arg Met Glu Leu
1265                1270                1275

Met Gly Cys Asp Leu Asn Ser Cys Ser Met Pro Leu Gly Met Glu
1280                1285                1290

Ser Lys Ala Ile Ser Asp Ala Gln Ile Thr Ala Ser Ser Tyr Phe
1295                1300                1305

Thr Asn Met Phe Ala Thr Trp Ser Pro Ser Lys Ala Arg Leu His
1310                1315                1320

Leu Gln Gly Arg Ser Asn Ala Trp Arg Pro Gln Val Asn Asn Pro
1325                1330                1335

Lys Glu Trp Leu Gln Val Asp Phe Gln Lys Thr Met Lys Val Thr
1340                1345                1350

Gly Val Thr Thr Gln Gly Val Lys Ser Leu Leu Thr Ser Met Tyr
1355                1360                1365

Val Lys Glu Phe Leu Ile Ser Ser Ser Gln Asp Gly His Gln Trp
1370                1375                1380

Thr Leu Phe Phe Gln Asn Gly Lys Val Lys Val Phe Gln Gly Asn
1385                1390                1395

Gln Asp Ser Phe Thr Pro Val Val Asn Ser Leu Asp Pro Pro Leu
```

```
                1400                1405                1410

Leu Thr Arg Tyr Leu Arg Ile His Pro Gln Ser Trp Val His Gln
    1415                1420                1425

Ile Ala Leu Arg Met Glu Val Leu Gly Cys Glu Ala Gln Asp Leu
    1430                1435                1440

Tyr

<210> SEQ ID NO 6
<211> LENGTH: 585
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
```

```
                        325                 330                 335
Arg His Pro Asp Tyr Ser Val Val Leu Leu Arg Leu Ala Lys Thr
                340                 345                 350
Tyr Glu Thr Thr Leu Glu Lys Cys Cys Ala Ala Ala Asp Pro His Glu
                355                 360                 365
Cys Tyr Ala Lys Val Phe Asp Glu Phe Lys Pro Leu Val Glu Glu Pro
                370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
                435                 440                 445
Ala Glu Asp Tyr Leu Ser Val Val Leu Asn Gln Leu Cys Val Leu His
                450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
                515                 520                 525
Leu Val Glu Leu Val Lys His Lys Pro Lys Ala Thr Lys Glu Gln Leu
                530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
                580                 585
```

MODULATION OF FVIII IMMUNOGENICITY BY TRUNCATED VWF

This is a national stage entry under 35 U.S.C. § 371 of International Application No. PCT/EP2018/066696, filed Jun. 22, 2018, which claims priority to EP 17177477.1, filed Jun. 22, 2017, and EP 18153579.0, filed Jan. 26, 2018, all of which are incorporated herein by reference.

FIELD OF THE INVENTION

The present invention relates to a recombinant polypeptide comprising a truncated von Willebrand Factor (VWF) capable of binding to blood coagulation Factor VIII (FVIII) for use in reducing the immunogenicity of Factor VIII (FVIII) wherein said recombinant polypeptide and a Factor VIII (FVIII) protein are co-administered to a subject suffering from a blood coagulation disorder.

BACKGROUND OF THE INVENTION

There are various bleeding disorders caused by deficiencies of blood coagulation factors. The most common disorders are hemophilia A and B, resulting from deficiencies of blood coagulation factor VIII and IX, respectively. Another known bleeding disorder is von Willebrand's disease (VWD).

Hemophilia A is an inherited bleeding disorder. It results from a chromosome X-linked deficiency of blood coagulation Factor VIII, and affects almost exclusively males with an incidence of between one and two individuals per 10.000. The X-chromosome defect is transmitted by female carriers who are not themselves hemophiliacs. The clinical manifestation of hemophilia A is an increased bleeding tendency. Before treatment with Factor VIII concentrates was introduced the mean life span for a person with severe hemophilia was less than 20 years. The use of concentrates of Factor VIII from plasma has considerably improved the situation for the hemophilia A patients increasing the mean life span extensively, giving most of them the possibility to live a more or less normal life. However, there have been certain problems with the plasma derived concentrates and their use, the most serious of which have been the transmission of viruses. So far, viruses causing hepatitis B, non-A non-B hepatitis and AIDS have hit the population seriously. Since then different virus inactivation methods and new highly purified Factor VIII concentrates have recently been developed which established a very high safety standard also for plasma derived Factor VIII.

The cloning of the cDNA for Factor VIII (Wood et al. 1984. Nature 312:330-336; Vehar et al. 1984. Nature 312:337-342) made it possible to express Factor VIII recombinantly leading to the development of several recombinant Factor VIII products, which were approved by the regulatory authorities between 1992 and 2003. The fact that the central B domain of the Factor VIII polypeptide chain residing between amino acids Arg-740 and Glu-1649 does not seem to be necessary for full biological activity has also led to the development of B domain deleted Factor VIII products.

The mature Factor VIII molecule consists of 2332 amino acids which can be grouped into three homologous A domains, two homologous C domains and a B Domain which are arranged in the order: A1-A2-B-A3-C1-C2. During its secretion into plasma Factor VIII is processed intracellularly into a series of metal-ion linked heterodimers as single chain Factor VIII is cleaved at the B-A3 boundary and at different sites within the B-domain. This processing leads to heterogeneous heavy chain molecules consisting of the A1, the A2 and various parts of the B-domain which have a molecular size ranging from 90 kDa to 200 kDa. The heavy chains are bound via a metal ion to the light chains, which consist of the A3, the C1 and the C2 domain (Saenko et al. 2002. Vox Sang. 83:89-96). In plasma this heterodimeric Factor VIII binds with high affinity to von Willebrand Factor (vWF), which protects it from premature catabolism. The half-life of non-activated Factor VIII bound to vWF is about 12 hours in plasma.

VWF is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). Once secreted into plasma the protease ADAMTS13 cleaves VWF within the A1 domain of VWF.

In plasma FVIII binds with high affinity to von VWF, which protects it from premature catabolism and thus, plays in addition to its role in primary hemostasis a crucial role to regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al., Mol Cell Biol 9: 1233-1242, 1989). Free FVIII which is not bound to VWF has a half-life in circulation of approx. 2 hrs. (Vlot et al. Thromb Haemost 2000; 83:65-91).

In severe hemophilia A patients undergoing prophylactic treatment Factor VIII has to be administered intravenously (i.v.) about 3 times per week due to the short plasma half-life of Factor VIII of about 12 hours. Each i.v. administration is cumbersome, associated with pain and entails the risk of an infection especially as this is mostly done at home by the patients themselves or by the parents of children being diagnosed for hemophilia A.

It was thus highly desirable to create a Factor VIII with increased functional half-life allowing the manufacturing of pharmaceutical compositions containing Factor VIII, which have to be administered less frequently.

VWF-derived polypeptides, in particular VWF fragments, have been described to stabilize FVIII in vitro and in vivo. WO 2013/106787 A1 is directed to chimeric proteins comprising certain VWF fragments and a FVIII protein. Those chimeric hetero-dimers of FVIII and VWF-fragment do have a fixed molar ratio of VWF to FVIII of 1:1.

WO 2014/198699 A2 and WO 2013/083858 A2 describe VWF fragments and their use in the treatment of hemophilia. It was found that bioavailability of FVIIIs may be significantly improved upon extravascular co-administration with similar molar amounts of VWF fragments. Yee et al. (2014)

Blood 124(3):445-452 found that a VWF fragment containing the D'D3 domains is sufficient to stabilize Factor VIII in VWF-deficient mice.

One approach to provide a prolonged in vivo half-life of Factor VIII by co-administration of a truncated VWF has been disclosed in WO 2016/188907 A1.

However, a major complication in up to 30% of patients suffering from hemophilia A is the occurrence of inhibitors, in particular alloantibodies, that inactivate FVIII activity and may nullify replacement therapy. It has been described, that the risk of FVIII inhibitor generation in previously untreated patients with hemophilia A is higher when treated with recombinant FVIII products, and it has been speculated that the binding of VWF to different epitopes in the FVIII-LC (A3 and C2 domains) shields these epitopes and might therefore have a beneficial effect in reducing immunogenicity (C. Escuriola Ettinghausen, W. Kreuz; *Haemophilia* (2006), 12, (Suppl. 6), 102-106). Unshielded epitopes of FVIII appear to pose a risk of triggering the generation of inhibitors. In addition, the interaction of the FVIII-HC and the FVIII-LC in the two-chain FVIII complex is assumed to also have a shielding effect on otherwise freely accessible epitopes in the FVIII-HC and the FVIII-LC.

The development of neutralizing anti-factor VIII alloantibodies (inhibitors) in patients with severe hemophilia A may depend on the concentrate used for replacement therapy. Patients treated with plasma-derived factor VIII containing von Willebrand factor had a lower incidence of inhibitors than those treated with recombinant factor VIII. The incidence of inhibitors in young boys (age<6 years, severe hemophilia A, and no previous treatment with any factor VIII concentrate before) treated with recombinant FVIII was measured 1.87-fold higher compared with those patients treated with pdFVIII. Inhibitor incidence was 26.8% in the cohort treated with recombinant FVIII compared with 44.5% in the cohort of pdFVIII (Peyvandi F, N Engl J Med (2016), 74:2054-64).

Hence, in addition to an increased in vivo half-life of FVIII, there is an ongoing need for improved therapies to avoid or reduce the occurrence of such FVIII inhibitors.

It has been suggested that VWF might decrease immunoreactions against Factor VIII when in complex with Factor VIII by shielding FVIII from known potential inhibitor antibody sites on the heavy chain (A2 domain) and the light chain (A3/C2 domain) (Ragni, J Thromb. Haemost. 10: 2324-2327, 2012).

The purity of FVIII concentrates, and in particular the presence of von Willebrand factor (VWF), was controversially discussed to influence the immunogenicity of exogenous FVIII. Thus, S. Delignat et al. (Haemophilia (2012), 18, 248-254) assessed in vivo and in vitro the immunoprotective effect of VWF towards FVIII. VWF reduced the immunogenicity of FVIII in FVIII-deficient mice and prevented in vitro the endocytosis of FVIII by professional antigen-presenting cells (e.g. DCs). It was proposed that VWF, by virtue of increasing the half-life of FVIII in the circulation, may allow an increased contact time with tolerogenic marginal zone B cells in the spleen.

With WO13106787A1 chimeric proteins comprising a VWF fragment and a FVIII protein are shown, wherein the VWF fragment and the FVIII protein are covalently associated with each other or covalently linked to each other. The chimeric proteins are proposed to have less immunogenicity than a FVIII protein without the covalently linked fragment VWF. Data regarding immunogenicity are not shown. The molar ratio of the constructs is fixed at 1:1.

According to the disclosure of WO15185758A2 a composition comprising a non-covalent complex of Factor VIII and VWF peptides is proposed for reduction of inhibitor formation against FVIII. However, the VWF peptides still exhibit amino acids 764 to 1035 and 1691 to 1905 and no data regarding immunogenicity are presented.

WO 2013/083858 A2 describes that VWF and fragments thereof may protect FVIII against cellular uptake by human antigen-presenting cells. Compared to full-length plasma-derived VWF (amino acids 764-2813), the tested fragments, however, did only show moderate reduction of FVIII uptake. The tested VWF fragments did not comprise any half-life extending moiety for increasing the half-life of VWF fragments and/or of FVIII.

Thus, there is still an unmatched clinical need to provide FVIII products or compositions having a long half-life and a reduced immunogenicity.

SUMMARY OF THE INVENTION

It has been found by the inventors that the uptake of Factor VIII by antigen-presenting cells, particularly monocyte-derived dendritic cells, can be substantially reduced by coadministering a Factor VIII protein together with a dimeric recombinant polypeptide comprising a truncated VWF, preferably a truncated VWF comprising amino acids 764 to 1242 of SEQ ID NO:4. The recombinant polypeptide comprises preferably a half-life extending moiety (HLEM), in particular, may be fused to human albumin.

Thus, an aspect of the present invention refers to a recombinant polypeptide comprising a truncated von Willebrand Factor (VWF) capable of binding to blood coagulation Factor VIII (FVIII) for use in reducing the immunogenicity of Factor VIII (FVIII), wherein said recombinant polypeptide and a Factor VIII (FVIII) protein are co-administered to a subject suffering from a blood coagulation disorder. This includes, that said recombinant polypeptide and the Factor VIII (FVIII) protein may preferably be administered simultaneously, sequentially or separately, said modes of administration being encompassed by the term "co-administered". The immunogenicity of Factor VIII (FVIII) is preferably reduced when compared to a reference treatment, wherein said reference treatment is identical to said treatment, except said FVIII is administered without co-administration of the recombinant polypeptide.

In addition, it has been found by the inventors that the uptake of Factor VIII by antigen-presenting cells, particularly monocyte-derived dendritic cells, can be further reduced by coadministering a Factor VIII protein together with a molar excess of recombinant polypeptide comprising a truncated VWF. With other words, by increasing the molar ratio of recombinant polypeptide comprising a truncated VWF over coadministered FVIII an enhanced reduction of the uptake of Factor VIII by antigen-presenting cells, particularly monocyte-derived dendritic cells, can be achieved.

Thus, a further aspect of the present invention relates to the molar ratio of the recombinant polypeptide to the FVIII to be co-administered being at least 2:1, at least 3:1, at least 4:1, at least 5:1, at least 8:1, at least 10:1, at least 15:1, at least 20:1, at least 25:1 or at least 50:1 or even higher molar ratios.

A further aspect of the present invention refers to a pharmaceutical composition comprising (i) a recombinant polypeptide comprising a truncated von Willebrand Factor (VWF) according to the invention, and (ii) a Factor VIII protein (FVIII), for use in reducing the immunogenicity of Factor VIII (FVIII) wherein said composition is administered to a subject suffering from a blood coagulation disorder, wherein, preferably, said subject is expected to develop an immune reaction against FVIII, particularly an immune reaction characterized by inhibitory antibodies against FVIII.

Still a further aspect refers to pharmaceutical kit comprising (i) a first composition comprising a Factor VIII (FVIII) protein and (ii) a second composition comprising a recombinant polypeptide comprising a truncated von Willebrand Factor (VWF) for use in reducing the immunogenicity of Factor VIII (FVIII) wherein said compositions are co-administered to a subject suffering from a blood coagulation disorder, wherein, preferably, said subject is expected to develop an immune reaction against FVIII, particularly an immune reaction characterized by inhibitory antibodies against FVIII, and wherein said FVIII and said recombinant polypeptide are provided within the kit in order to allow prior to administration for at least a proportion of said recombinant polypeptide to bind to said FVIII.

Still a further aspect of the present invention refers to a method for reducing the immunogenicity of FVIII, the method comprising co-administering an effective amount of a recombinant polypeptide comprising a truncated von Willebrand Factor (VWF) and a Factor VIII (FVIII) protein to a subject suffering from a blood coagulation disorder, wherein said recombinant polypeptide reduces the immunogenicity of FVIII. Preferably, said subject is expected to develop an immune reaction against FVIII, particularly an immune reaction characterized by inhibitory antibodies against FVIII.

In a particular aspect, the recombinant polypeptide comprises a truncated VWF which is a dimer.

In a further particular aspect, the recombinant polypeptide comprises a truncated VWF having a functional VWF D' domain and a functional VWF D3 domain and preferably lacking a functional VWF A1 domain.

In a further particular aspect, the recombinant polypeptide comprises a truncated VWF having a functional VWF D' domain and a functional VWF D3 domain, preferably lacking any other VWF functional domains.

In a further particular aspect, the recombinant polypeptide comprises a truncated VWF having a functional VWF D' domain and a functional VWF D3 domain, preferably lacking any other VWF functional domains, and carrying one or multiple amino acid mutations increasing the affinity to FVIII.

In a still further particular embodiment, the recombinant polypeptide comprises a half-life extending moiety (HLEM) such as albumin.

The present invention therefore relates to the following preferred embodiments [1] to [44]:

[1] A recombinant polypeptide comprising a truncated von Willebrand Factor (VWF) capable of binding to blood coagulation Factor VIII (FVIII) for use in reducing the immunogenicity of Factor VIII (FVIII), wherein said recombinant polypeptide and a blood coagulation Factor VIII (FVIII) protein are co-administered to a subject suffering from a blood coagulation disorder. The immunogenicity of Factor VIII (FVIII) is preferably reduced when compared to a reference treatment, wherein said reference treatment is identical to said treatment, except said FVIII is administered without co-administration of the recombinant polypeptide.

[2] The recombinant polypeptide for use according to embodiment [1], wherein the reduced immunogenicity of FVIII comprises a subject's reduced humoral immune response against FVIII, in particular a lower titer and/or frequency of inhibitory antibodies against FVIII, and/or a reduced cell-mediated immune response against FVIII.

[3] The recombinant polypeptide for use according to any one of the preceding embodiments, wherein the reduction of immunogenicity of FVIII following administration is achieved or accompanied by a reduced uptake of FVIII into subject's antigen presenting cells (APCs) in the presence of the co-administered recombinant polypeptide, preferably when compared to a reference treatment, wherein said reference treatment is identical to said treatment, except said FVIII is administered without co-administration of the recombinant polypeptide.

[4] The recombinant polypeptide for use according to embodiment [3], wherein the APCs are selected from the group consisting of dendritic cells and macrophages.

[5] The recombinant polypeptide for use according to embodiments [3] or [4], wherein following co-administration of the recombinant polypeptide and FVIII, the portion of the subject's APCs having internalized FVIII are reduced by at least a factor of 1.1, by at least a factor of 1.2, by at least a factor of 1.3, by at least a factor of 1.4, by at least a factor of 1.5, by at least a factor of 2, by at least a factor of 3, by at least a factor of 4, by at least a factor of 5, or by at least a factor of 10, when compared to a reference treatment, wherein said reference treatment is identical to said treatment, except said FVIII is administered without co-administration of the recombinant polypeptide.

[6] The recombinant polypeptide for use according to any one of embodiments [3] to [5], wherein the $IC_{50}$ value for the co-administered recombinant polypeptide representing the potential of FVIII uptake inhibition into APCs is only moderately increased when compared to a respective $IC_{50}$ value for a full length VWF, preferably the $IC_{50}$ value of co-administered recombinant polypeptide does exceed the $IC_{50}$ value of full length VWF by not more than a factor of 3, by not more than a factor of 2.5, by not more than a factor of 2.4, by not more than a factor of 2.3, by not more than a factor of 2.2, by not more than a factor of 2.1, by not more than a factor of 2.0, by not more than a factor of 1.8, by not more than a factor of 1.5, by not more than a factor of 1.3, by not more than a factor of 1.2, or by not more than a factor of 1.1. The calculation of $IC_{50}$ values within the present disclosure is based on molar concentration of the recombinant polypeptide monomer even when present as a dimer.

[7] The recombinant polypeptide for use according to any one of embodiments [3] to [5], wherein the $IC_{50}$ value for the co-administered recombinant polypeptide representing the potential of FVIII uptake inhibition into APCs (calculation based on molar concentration of the monomer) is either identical or even reduced when compared to a respective $IC_{50}$ value for a full length VWF, preferably the $IC_{50}$ value of co-administered recombinant polypeptide is reduced compared to the $IC_{50}$ value of full length VWF by a factor of at least 1.2, of at least 1.5, of at least 2, of at least 2.5 or of at least 3.

[8] The recombinant polypeptide for use according to any one of the preceding embodiments, wherein the reduction of immunogenicity of FVIII following administration of the recombinant polypeptide is achieved or accompanied by a quenched MHC class II type antigen presentation of FVIII peptides by subject's antigen presenting cells (APCs) in the presence of the recombinant polypeptide, preferably when compared to a reference treatment, wherein said reference treatment is identical to said treatment, except said FVIII is administered without administration of the recombinant polypeptide. Said MHC class II type antigen presentation of FVIII peptides by subject's antigen presenting cells (APCs) is preferably being quenched (i.e. reduced) by a factor of at least 1.5, at least 2.0, at least 2.5, at least 3.0, at least 3.5, or at least 4.0.

[9] The recombinant polypeptide for use according to any one of the preceding embodiments, wherein the reduction of immunogenicity of FVIII following administration of the recombinant polypeptide is achieved or accompanied by a quenched number of unique MHC class II type binding FVIII peptides by subject's antigen presenting cells (APCs) in the presence of the recombinant polypeptide, preferably when compared to a reference treatment, wherein said reference treatment is identical to said treatment, except said FVIII is administered without administration of the recombinant polypeptide. Said number of unique MHC class II type binding FVIII peptides by subject's antigen presenting cells (APCs) is preferably being quenched (i.e. reduced) by a factor of at least 1.5, at least 2.0, at least 2.5, at least 3.0, at least 3.5, or at least 4.0.

[10] The recombinant polypeptide for use according to any one of the preceding embodiments, wherein the reduction of immunogenicity of FVIII following administration of the recombinant polypeptide is achieved or accompanied by a quenched number of clustered MHC class II type binding FVIII peptides by subject's antigen presenting cells (APCs) in the presence of the recombinant polypeptide, preferably when compared to a reference treatment, wherein said reference treatment is identical to said treatment, except said FVIII is administered without administration of the recombinant polypeptide. Said number of clustered MHC class II type binding FVIII peptides by subject's antigen presenting cells (APCs) is preferably being quenched (i.e. reduced) by a factor of at least 1.5, at least 2.0, at least 2.5, at least 3.0, at least 3.5, or at least 4.0.

[11] The recombinant polypeptide for use according to any one of the preceding embodiments, wherein the subject is a subject previously untreated with FVIII.

[12] The recombinant polypeptide for use according to any one of the embodiments [1] to [10], wherein the subject is a subject having been pre-treated with FVIII and/or is subjected to a treatment change.

[13] The recombinant polypeptide for use according to any one of the preceding embodiments, wherein the subject has a risk and/or is expected of developing an immune reaction against FVIII, particularly an immune reaction characterized by inhibitory antibodies against FVIII.

[14] The recombinant polypeptide for use according to any one of the preceding embodiments, wherein the recombinant polypeptide and FVIII are co-administered for prophylactic or therapeutic treatment of a subject suffering from a blood coagulation disorder.

[15] The recombinant polypeptide for use according to any one of the preceding embodiments, wherein the reduced immunogenicity of FVIII is characterized by a lower titer of inhibitory antibodies directed against FVIII, preferably the titer of inhibitory antibodies directed against FVIII is reduced by at least 2%, by at least 5%, by at least 10%, by at least 15%, by at least 20%, by at least 30%, by at least 40%, by at least 50%, or by at least 80%, when compared to the titer of FVIII antibodies in a subject following a reference treatment, wherein said reference treatment is identical to said treatment, except said FVIII is administered without co-administration of said recombinant polypeptide.

[16] The recombinant polypeptide for use according to any one of the preceding embodiments, wherein the reduced immunogenicity of FVIII is characterized by a lower frequency of inhibitory antibodies directed against FVIII in a subject population, preferably the frequency of inhibitory antibodies directed against FVIII is reduced by at least 5%, by at least 10%, by at least 15%, by at least 20%, by at least 30%, by at least 40%, by at least 50%, by at least 80%, or by at least 90%, when compared to the frequency of FVIII antibodies in a subject population following a reference treatment, wherein said reference treatment is identical to said treatment, except said FVIII is administered without co-administration of said recombinant polypeptide.

[17] The recombinant polypeptide for use according to any one of the preceding embodiments, wherein the reduced immunogenicity of FVIII is provided in patients for at least 3 months, at least 4 months, at least 5 months, at least 6 months, at least 7 months, at least 8 months, at least 9 months, or at least 12 months following treatment.

[18] The recombinant polypeptide for use according to any one of the preceding embodiments, wherein the recombinant polypeptide is administered as a dimer, preferably as a homo-dimer.

[19] The recombinant polypeptide for use according to any one of the preceding embodiments, wherein the molar ratio of the recombinant polypeptide to the FVIII to be co-administered is at least 2:1, at least 3:1, at least 4:1, at least 5:1, at least 6:1, at least 8:1, at least 10:1, at least 15:1, at least 20:1, at least 25:1, at least 50:1, at least 70:1, at least 80:1, at least 100:1, at least 150:1, based on the amount of recombinant polypeptide calculated as a monomer and the amount of FVIII calculated as a monomer.

[20] The recombinant polypeptide for use according to any one of the preceding embodiments, wherein the subject is a human subject.

[21] The recombinant polypeptide for use according to any one of the preceding embodiments, wherein said polypeptide is administered intravenously, subcutaneously, intradermally, orally, transdermally, intranasally, intraperitoneally, topically or locally, sublingually or intramuscularly, preferably intravenously or subcutaneously.

[22] The recombinant polypeptide for use according to any one of the preceding embodiments, wherein said polypeptide comprises a functional VWF D' domain and/or a functional VWF D3 domain.

[23] The recombinant polypeptide for use according to any one of the preceding embodiments, wherein said polypeptide lacks a functional VWF A1 domain.

[24] The recombinant polypeptide for use according to any one of the preceding embodiments, wherein said recombinant polypeptide comprises a functional VWF D' domain and/or a functional VWF D3 domain and the recombinant polypeptide lacks any other of VWF functional domains.

[25] The recombinant polypeptide for use according to any one of the preceding embodiments, wherein the truncated VWF comprises an amino acid sequence having a sequence identity of at least 90% to amino acids 776 to 805 of SEQ ID NO:4, preferably comprises an amino acid sequence having a sequence identity of at least 90% to amino acids 764 to 1242 of SEQ ID NO:4.

[26] The recombinant polypeptide for use according to any one of the preceding embodiments, wherein the truncated VWF consists of (a) amino acids 764 to 1242 of SEQ ID NO:4, of (b) an amino acid sequence having a sequence identity of at least 90% to amino acids 764 to 1242 of SEQ ID NO:4, or of (c) a fragment of (a) or (b).

[27] The recombinant polypeptide for use according to any one of the preceding embodiments, the recombinant polypeptide has at least one of the following amino acid substitutions compared to the VWF wild-type amino acid sequence when referring to the sequence numbering of SEQ ID NO:4, the substitution being selected from the group consisting of: S764G/S766Y, S764P/S766I, S764P/S766M, S764V/S766Y, S764E/S766Y, S764Y/S766Y, S764L/S766Y, S764P/S766W, S766W/S806A, S766Y/P769K, S766Y/P769N, S766Y/P769R and S764P/S766L, S764P/S766W/V1083A, S764G/S766Y/V1083A, S764E/S766Y/V1083A, N1011S/V1083A/K1181E, S766Y/V1083A, V1083A, 51042T, V805A/Q1158L, K912E/T1088S, and L781P.

[28] The recombinant polypeptide for use according to embodiment [27], the recombinant polypeptide has at least one of the amino acid substitutions S764E/S766Y or S764E/S766Y/V1083A, preferably the recombinant polypeptide has the two amino acid substitutions S764E/S766Y or has the three amino acid substitutions S764E/S766Y/V1083A.

[29] The recombinant polypeptide for use according to any one of the preceding embodiments, wherein said polypeptide comprises a half-life extending moiety (HLEM).

[30] The recombinant polypeptide for use according to embodiment [29], wherein the HLEM is a heterologous amino acid sequence fused to the truncated VWF.

[31] The recombinant polypeptide for use according to embodiment [30], wherein said heterologous amino acid sequence comprises or consists of a polypeptide selected from the group consisting of immunoglobulin constant regions and portions thereof, preferably the Fc portion of immunoglobulin, albumin and fragments thereof, transferrin and fragments thereof, the C-terminal peptide of human chorionic gonadotropin, an XTEN sequence, homo-amino acid repeats (HAP), proline-alanine-serine repeats (PAS), albumin or fragments thereof, afamin, alpha-fetoprotein, Vitamin D binding protein, polypeptides capable of binding under physiological conditions to albumin or immunoglobulin constant regions, polypeptides capable of binding to the neonatal Fc receptor (FcRn) and combinations thereof.

[32] The recombinant polypeptide for use according to embodiment [29], wherein the HLEM is conjugated to the recombinant polypeptide.

[33] The recombinant polypeptide for use according to embodiment [32], wherein said HLEM is selected from the group consisting of hydroxyethyl starch (HES), polyethylene glycol (PEG), polysialic acids (PSAs), elastin-like polypeptides, heparosan polymers, hyaluronic acid and albumin binding ligands, e.g. fatty acid chains, and combinations thereof.

[34] The recombinant polypeptide for use according to any one of the preceding embodiments, wherein the blood coagulation disorder is hemophilia A.

[35] The recombinant polypeptide for use according to any one of the preceding embodiments, wherein co-administration of the recombinant polypeptide and the FVIII protein is achieved either (i) by administration together in a single composition comprising the recombinant polypeptide and the FVIII protein, or (ii) by administration of the recombinant polypeptide (first compound) and the FVIII protein (second compound) provided in separate compositions as part of a combined therapy, wherein the first compound is administered before, after or concurrently with the second compound.

[36] The recombinant polypeptide for use according to any one of the preceding embodiments, wherein following administration hypersensitivity against FVIII is being reduced and/or a risk of anaphylaxis is being a reduced.

[37] The recombinant polypeptide for use according to any one of the preceding embodiments, wherein the FVIII is a plasma derived FVIII protein or a recombinant FVIII protein.

[38] The recombinant polypeptide for use according to any one of the preceding embodiments, wherein the dosage of co-administered FVIII protein does not exceed 2500 IU/kg, 1500 IU/kg, 1000 IU/kg, 600 IU/kg, 500 IU/kg or 400 IU/kg.

[39] A pharmaceutical composition comprising
  (i) a recombinant polypeptide comprising a truncated von Willebrand Factor (VWF), in particular a recombinant polypeptide according to any embodiment disclosed herein, and
  (ii) optionally a Factor VIII protein (FVIII), the composition being for use in reducing the immunogenicity of Factor VIII (FVIII), wherein said composition is administered to a subject suffering from a blood coagulation disorder, preferably wherein said subject has a risk and/or is expected to develop an immune reaction against FVIII, particularly an immune reaction characterized by inhibitory antibodies against FVIII.

[40] A pharmaceutical composition comprising a recombinant polypeptide comprising a truncated von Willebrand Factor (VWF), in particular a recombinant polypeptide according to any embodiment disclosed herein, the composition being provided for use in reducing the immunogenicity of Factor VIII (FVIII), wherein said composition is not comprising any Factor VIII protein (FVIII) and said composition is administered in conjunction with a Factor VIII protein (FVIII) to a subject suffering from a blood coagulation disorder, preferably wherein said subject has a risk and/or is expected to develop an immune reaction against FVIII, particularly an immune reaction characterized by inhibitory antibodies against FVIII.

[41] A pharmaceutical composition according to any one of embodiments [39] to [40], wherein the patient is on or is about to start with prophylactic treatment with a FVIII product.

[42] A pharmaceutical kit comprising
  (i) a first composition comprising a Factor VIII (FVIII) protein and
  (ii) a second composition comprising a recombinant polypeptide comprising a truncated von Willebrand Factor (VWF), in particular a recombinant polypeptide according to any embodiment disclosed herein,
the kit being provided for use in reducing the immunogenicity of Factor VIII (FVIII), wherein said compositions are to be co-administered to a subject suffering from a blood coagulation disorder, preferably wherein said subject has a risk and/or is expected to develop an immune reaction against FVIII, particularly an immune reaction characterized by inhibitory antibodies against FVIII,
and wherein said FVIII and said recombinant polypeptide are provided within the kit in order to allow prior to administration for at least a proportion of said recombinant polypeptide to bind to said FVIII.

[43] A method for reducing the immunogenicity of FVIII, the method comprising co-administering an effective amount of a recombinant polypeptide comprising a truncated von Willebrand Factor (VWF), preferably a recombinant polypeptide according to any embodiment disclosed herein, and a Factor VIII (FVIII) protein to a subject suffering from a blood coagulation disorder, wherein said recombinant polypeptide reduces the immunogenicity of FVIII.

[44] The method of embodiment [43], wherein said subject has a risk and/or is expected to develop an immune reaction against FVIII, particularly an immune reaction characterized by inhibitory antibodies against FVIII.

DETAILED DESCRIPTION OF PREFERRED EMBODIMENTS

Reduction of FVIII Immunogenicity

Figure 1:
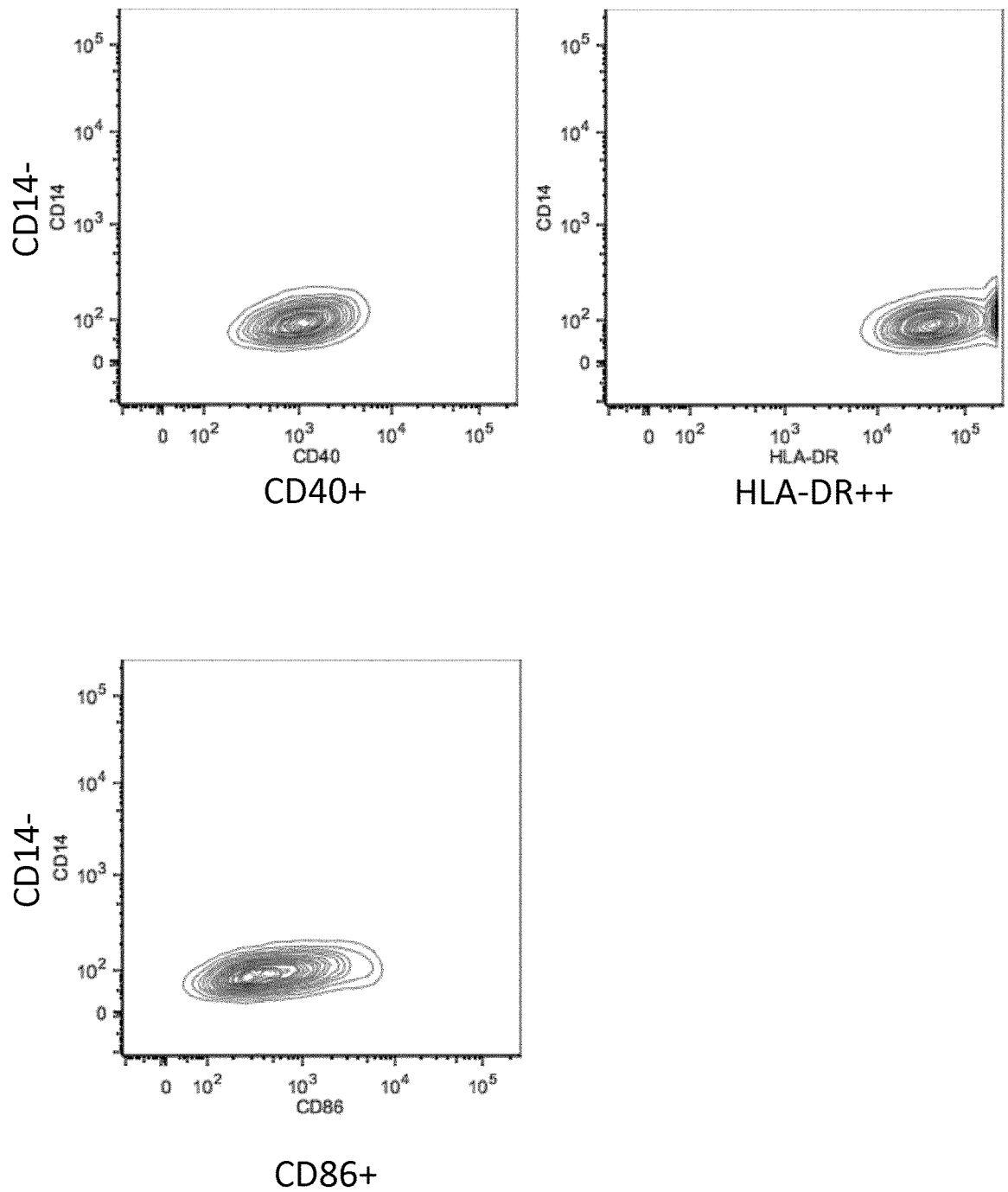
FIG. 1 shows surface marker phenotyping of MDDCs showing a negative staining for CD14 and positive stains for CD40, HLA-DR and CD86 by flow cytometry.

Within the present disclosure "the recombinant polypeptide" is alternatively also referred to as "the polypeptide of the invention".

The present invention is based on an observation that uptake of FVIII into antigen-presenting cells (APCs) is substantially reduced in the presence of a recombinant polypeptide comprising a truncated VWF when compared to the uptake following a reference treatment wherein said reference treatment is identical to the treatment of the invention, except that FVIII is administered without coadministration of the recombinant polypeptide.

In terms of present invention the achieved reduced immunogenicity of FVIII may also be understood as inducing less immunogenicity against FVIII.

The reduced immunogenicity of FVIII includes, but is not limited to, a reduced humoral immune response, i.e. a lower titer and/or frequency of inhibitory anti-FVIII antibodies and/or a reduced cell-mediated immune response against FVIII. Further, the reduced immunogenicity may include a reduced hypersensitivity reaction against FVIII including a reduced risk of anaphylaxis. For example, the reduced immunogenicity of FVIII may be characterized by a lower titer of inhibitory antibodies directed against FVIII, preferably the titer of inhibitory antibodies directed against FVIII is reduced by at least 2%, by at least 5%, by at least 10%, by at least 15% or by at least 20%, when compared to the titer of inhibitory antibodies in a subject following a reference treatment, wherein said reference treatment is identical to said treatment, except said FVIII is administered without co-administration of said recombinant polypeptide. Inhibiting antibodies are herein alternatively referred to as "inhibitor".

Further, the reduced immunogenicity of FVIII may be characterized by a lower frequency of inhibitory antibodies directed against FVIII, preferably the frequency of inhibitory antibodies directed against FVIII is reduced by at least 5%, by at least 10%, by at least 15%, by at least 20% or by at least 30%, when compared to the frequency of inhibitory antibodies in a subject population following a reference treatment, wherein said reference treatment is identical to said treatment, except said FVIII is administered without co-administration of said recombinant polypeptide. The titer and/or frequency of inhibitory antibodies directed against FVIII may be determined according to standard methods, e.g. according to a Bethesda assay.

The reduction of immunogenicity of FVIII may be achieved by reduced uptake of FVIII into antigen-presenting cells (APCs) in the presence of the coadministered recombinant polypeptide, wherein the APCs may be selected from the group consisting of dendritic cells or macrophages. For example, coadministration of the recombinant polypeptide and FVIII reduces the portion of subject's APCs having internalized FVIII by at least a factor of 1.1, by at least a factor of 1.2, by at least a factor of 1.3, by at least a factor of 1.4, by at least a factor of 1.5, by at least a factor of 2, by at least a factor of 3 or by at least a factor of 4, when compared to a reference treatment, wherein said reference treatment is identical to said treatment, except said FVIII is administered without co-administration of the recombinant polypeptide.

According to a preferred embodiment, the reduction of immunogenicity of FVIII following administration of the recombinant polypeptide is achieved or accompanied by a quenched MHC class II type antigen presentation of FVIII peptides by subject's antigen presenting cells (APCs) in the presence of the recombinant polypeptide, preferably when compared to a reference treatment, wherein said reference treatment is identical to said treatment, except said FVIII is administered without administration of the recombinant polypeptide. Said MHC class II type antigen presentation of FVIII peptides by subject's antigen presenting cells (APCs) is preferably being quenched (i.e. reduced) by a factor of at least 1.5, at least 2.0, at least 2.5, at least 3.0, at least 3.5, or at least 4.0.

According to a further preferred embodiment, the reduction of immunogenicity of FVIII following administration of the recombinant polypeptide is achieved or accompanied by a quenched number of unique MHC class II type binding FVIII peptides by subject's antigen presenting cells (APCs) in the presence of the recombinant polypeptide, preferably when compared to a reference treatment, wherein said reference treatment is identical to said treatment, except said FVIII is administered without administration of the recombinant polypeptide. Said number of unique MHC class II type binding FVIII peptides by subject's antigen presenting cells (APCs) is preferably being quenched (i.e. reduced) by a factor of at least 1.5, at least 2.0, at least 2.5, at least 3.0, at least 3.5, or at least 4.0.

According to a further preferred embodiment, the reduction of immunogenicity of FVIII following administration of the recombinant polypeptide is achieved or accompanied by a quenched number of clustered MHC class II type binding FVIII peptides by subject's antigen presenting cells (APCs) in the presence of the recombinant polypeptide, preferably when compared to a reference treatment, wherein said reference treatment is identical to said treatment, except said FVIII is administered without administration of the recombinant polypeptide. Said number of clustered MHC class II type binding FVIII peptides by subject's antigen presenting cells (APCs) is preferably being quenched (i.e. reduced) by a factor of at least 1.5, at least 2.0, at least 2.5, at least 3.0, at least 3.5, or at least 4.0.

The subject's MHC class II haplotype may in particular be selected from the group consisting of HLA-DR, HLA-DP, and HLA-DQ.

According to a further preferred embodiment, at least a portion of said FVIII peptides is capable of triggering T cell proliferation which is a necessary step for T helper mediated B cell activation/antibody secretion.

The number of unique MHC class II binding FVIII peptides is the number of distinct peptide sequences that can be uniquely assigned to FVIII. These are the peptides that are unique to the FVIII protein, and which do not occur in other proteins. The number of unique MHC class II binding FVIII peptides is used to quantify antigen presentation by subject's antigen presenting cells (APCs).

Unique MHC class binding FVIII peptides may overlap and may be grouped. MHC class II binding FVIII peptide clusters are imbedded alignments of overlapping unique MHC class II binding FVIII peptides. The number of MHC class II binding FVIII peptide clusters presented by subject's antigen presenting cells (APCs) is also used to quantify antigen presentation Ratios As described in more detail below, the polypeptide of the invention may be a monomer, a dimer, or a mixture thereof. Preferably, the polypeptide is a dimer. Any molar ratios according to the invention refer to a ratio of the molar concentration of the monomeric subunit of the polypeptide of the invention, whether actually present as monomer or dimer. Ratios are formed over the molar concentration of the co-administered FVIII. Any ratios of polypeptide of the invention over FVIII in this application refer to the amount of monomers comprised in the polypeptide of the invention, which is preferably present as a dimer, to be administered (in mole) divided by the amount of FVIII to be administered (in mole), unless indicated otherwise. By way of non-limiting example the co-administration of 100 μM of a monomeric polypeptide of the invention with 1 μM of FVIII means a ratio of 100. The same ratio of 100 is obtained if 50 μM of a dimeric polypeptide of the invention are co-administered with 1 μM of FVIII. A ratio of, for example, 100 is being alternatively referred to herein as 100:1.

The molar ratio of the recombinant polypeptide of the invention to be administered to FVIII to be administered is preferably at least 2:1, at least 3:1, at least 4:1, at least 5:1, at least 6:1, at least 8:1, at least 10:1, at least 15:1, at least 20:1, at least 25:1 or at least 50:1 based on the amount of recombinant polypeptide calculated as a monomer and the amount of FVIII calculated as a monomer.

The molar ratio of the polypeptide of the invention to be administered to FVIII to be administered is according to another aspect of the invention above 50:1, more preferably the ratio is greater than 60:1, at least 75:1, at least 100:1, greater than 200:1, at least 300:1, at least 400:1, at least 500:1, at least 600:1, at least 700:1, at least 800:1, at least 900:1, at least 1,000:1, at least 1,500:1, at least 2,000:1, at least 2,500:1, at least 3,000:1 at least 5,000:1, at least 8,000:1 or up to 10,000:1.

The molar ratio of the polypeptide of the invention to be administered to FVIII to be administered may according to certain embodiments not exceed a ratio of 10,000, a ratio of 5,000, a ratio of 2,500, a ratio of 2,000, a ratio of 1,500, a ratio of 1,000, a ratio of 750 or not exceed a ratio of 500.

The molar ratio of the polypeptide of the invention to be administered to FVIII to be administered according to further embodiments may range from 2 to 1,000, or from 4 to 750, or from 10 to 500.

The ratio of the polypeptide of the invention to be administered to FVIII to be administered is provided in a range to ensure a sufficiently increased half-life of FVIII and simultaneously to ensure the herein identified reduced immunogenicity of FVIII by co-administration of the polypeptide of the invention. In particular in light of prior published disclosures, specifically considering above cited Delignet et al., 2012, it was very surprisingly found herewith that both objects could be achieved simultaneously.

Further details of the treatment in accordance with the invention are described further below.

The Truncated VWF

The present invention relates to a recombinant polypeptide comprising a truncated von Willebrand Factor (VWF). The term "von Willebrand Factor" (VWF) as used herein includes naturally occurring (native) VWF, but also variants thereof retaining at least the FVIII binding activity of naturally occurring VWF, e.g. sequence variants where one or more residues have been inserted, deleted or substituted. The FVIII binding activity is determined by a FVIII-VWF binding assay as described in Example 2 of WO 2016/188907 A1 herein incorporated by reference.

A preferred VWF in accordance with this invention is human VWF represented by the amino acid sequence shown in SEQ ID NO:4. The cDNA encoding SEQ ID NO:4 is shown in SEQ ID NO:3.

The gene encoding human native VWF is transcribed into a 9 kb mRNA which is translated into a pre-propolypeptide of 2813 amino acids with an estimated molecular weight of 310,000 Da. The pre-propolypeptide contains an N-terminal 22 amino acids signal peptide, followed by a 741 amino acid pro-polypeptide (amino acids 23-763 of SEQ ID NO:4) and the mature subunit (amino acids 764-2813 of SEQ ID NO:4). Cleavage of the 741 amino acids propolypeptide from the N-terminus results in mature VWF consisting of 2050 amino acids. The amino acid sequence of the human native VWF pre-propolypeptide is shown in SEQ ID NO:4. Unless indicated otherwise, the amino acid numbering of VWF residues in this application refers to SEQ ID NO:4, even if the VWF molecule, in particular a truncated VWF, does not comprise all residues of SEQ ID NO:4.

The propolypeptide of native VWF comprises multiple domains. Different domain annotations can be found in the literature (see, e.g. Zhou et al. (2012) Blood 120(2): 449-458). The following domain annotation of native pre-propolypeptide of VWF is applied in this application:

D1-D2-D'-D3-A1-A2-A3-D4-C1-C2-C3-C4-C5-C6-CK

With reference to SEQ ID NO:4, the D' domain consists of amino acids 764-865; and the D3 domain consists of amino acids 866-1242.

The feature "truncated" in terms of the present invention means that the polypeptide does not comprise the entire amino acid sequence of mature VWF (amino acids 764-2813 of SEQ ID NO:4). Typically, the truncated VWF does not comprise all amino acids 764-2813 of SEQ ID NO:4 but only a fragment thereof. A truncated VWF may also be referred to as a VWF fragment, or in the plural as VWF fragments.

Typically, the truncated VWF is capable of binding to a Factor VIII. Preferably, the truncated VWF is capable of binding to the mature form of human native Factor VIII. In another embodiment, the truncated VWF is capable of binding to a recombinant FVIII, preferably to a FVIII as described herein, further preferred to a the single-chain Factor VIII consisting of the amino acid sequence SEQ ID NO:5. Binding of the truncated VWF to Factor VIII can be determined by a FVIII-VWF binding assay as described in Example 2 of WO 2016/188907 A1 herein incorporated by reference.

The truncated VWF of the present invention preferably comprises or consists of a functional D' domain and/or a functional D3 domain, in particular a functional D' domain and a functional D3 domain. The truncated von Willebrand Factor (VWF) of the invention is at least capable of binding to Factor VIII (FVIII). More preferably, the truncated VWF comprises or consists of an amino acid sequence having a sequence identity of at least 90% to amino acids 776 to 805 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 776 to 805 of SEQ ID NO:4 and is capable of binding to FVIII. Most preferably, the truncated VWF comprises or consists of amino acids 776 to 805 of SEQ ID NO:4. Unless indicated otherwise herein, sequence identities are determined over the entire length of the reference sequence (e.g. amino acids 776 to 805 of SEQ ID NO:4).

The truncated VWF of the present invention preferably comprises or consists of an amino acid sequence having a sequence identity of at least 90% to amino acids 766 to 864 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 766 to 864 of SEQ ID NO:4 and is capable of binding to FVIII. Most preferably, the truncated VWF comprises or consists of amino acids 766 to 864 of SEQ ID NO:4.

In another preferred embodiment, the truncated VWF consists of (a) an amino acid sequence having a sequence identity of at least 90% to amino acids 764 to 1242 of SEQ ID NO:4, or (b) a fragment thereof, provided that the truncated VWF is still capable of binding to FVIII. More preferably, the truncated VWF consists of (a) an amino acid sequence having a sequence identity of at least 95%, at least 96%, at least 97%, at least 98%, or at least 99%, to amino acids 764 to 1242 of SEQ ID NO:4, or (b) a fragment thereof, provided that the truncated VWF is still capable of binding to FVIII. Most preferably, the truncated VWF consists of (a) amino acids 764 to 1242 of SEQ ID NO:4, or (b) a fragment thereof, provided that the truncated VWF is still capable of binding to FVIII.

As described in more detail below, the polypeptide of the invention may be prepared by a method which uses cells comprising a nucleic acid encoding the polypeptide comprising the truncated VWF. The nucleic acid is introduced into suitable host cells by techniques that are known per se.

In a preferred embodiment, the nucleic acid in the host cell encodes (a) an amino acid sequence having a sequence identity of at least 90% to amino acids 1 to 1242 of SEQ ID NO:4, or (b) a fragment thereof, provided that the truncated mature VWF is still capable of binding to FVIII. More preferably, the nucleic acid encodes (a) an amino acid sequence having a sequence identity of at least 95%, at least 96%, at least 97%, at least 98%, or at least 99%, to amino acids 1 to 1242 of SEQ ID NO:4, or (b) a fragment thereof, provided that the truncated VWF is still capable of binding to FVIII. Most preferably, the nucleic acid encodes (a) amino acids 1 to 1242 of SEQ ID NO:4, or (b) a fragment thereof, provided that the truncated VWF is still capable of binding to FVIII. Especially if the polypeptide in accordance with this invention is a dimer, the nucleic acid will comprise a sequence encoding amino acids 1 to 763 of VWF (e.g. SEQ ID NO:4), even if the truncated VWF in the polypeptide does not comprise amino acids 1 to 763 of VWF (e.g. SEQ ID NO:4).

The truncated VWF of the recombinant polypeptide of the invention according to a preferred embodiment may not comprise amino acid sequence 1 to 763 of VWF of SEQ ID NO:4.

According to further preferred embodiments, the truncated VWF comprises or consists of one of the following amino acid sequences, each referring to SEQ ID NO:4: 776-805; 766-805; 764-805; 776-810; 766-810; 764-810; 776-815; 766-815; 764-815; 776-820; 766-820; 764-820; 776-825; 766-825; 764-825; 776-830; 766-830; 764-830; 776-835; 766-835; 764-835; 776-840; 766-840; 764-840; 776-845; 766-845; 764-845; 776-850; 766-850; 764-850; 776-855; 766-855; 764-855; 776-860; 766-860; 764-860; 776-864; 766-864; 764-864; 776-865; 766-865; 764-865; 776-870; 766-870; 764-870; 776-875; 766-875; 764-875; 776-880; 766-880; 764-880; 776-885; 766-885; 764-885; 776-890; 766-890; 764-890; 776-895; 766-895; 764-895; 776-900; 766-900; 764-900; 776-905; 766-905; 764-905; 776-910; 766-910; 764-910; 776-915; 766-915; 764-915; 776-920; 766-920; 764-920; 776-925; 766-925; 764-925; 776-930; 766-930; 764-930; 776-935; 766-935; 764-935; 776-940; 766-940; 764-940; 776-945; 766-945; 764-945; 776-950; 766-950; 764-950; 776-955; 766-955; 764-955; 776-960; 766-960; 764-960; 776-965; 766-965; 764-965; 776-970; 766-970; 764-970; 776-975; 766-975; 764-975; 776-980; 766-980; 764-980; 776-985; 766-985; 764-985; 776-990; 766-990; 764-990; 776-995; 766-995; 764-995; 776-1000; 766-1000; 764-1000; 776-1005; 766-1005; 764-1005; 776-1010; 766-1010; 764-1010; 776-1015; 766-1015; 764-1015; 776-1020; 766-1020; 764-1020; 776-1025; 766-1025; 764-1025; 776-1030; 766-1030; 764-1030; 776-1035; 766-1035; 764-1035; 776-1040; 766-1040; 764-1040; 776-1045; 766-1045; 764-1045; 776-1050; 766-1050; 764-1050; 776-1055; 766-1055; 764-1055; 776-1060; 766-1060; 764-1060; 776-1065; 766-1065; 764-1065; 776-1070; 766-1070; 764-1070; 776-1075; 766-1075; 764-1075; 776-1080; 766-1080; 764-1080; 776-1085; 766-1085; 764-1085; 776-1090; 766-1090; 764-1090; 776-1095; 766-1095; 764-1095; 776-1100; 766-1100; 764-1100; 776-1105; 766-1105; 764-1105; 776-1110; 766-1110; 764-1110; 776-1115; 766-1115; 764-1115; 776-1120; 766-1120; 764-1120; 776-1125; 766-1125; 764-1125; 776-1130; 766-1130; 764-1130; 776-1135; 766-1135; 764-1135; 776-1140; 766-1140; 764-1140; 776-1145; 766-1145; 764-1145; 776-1150; 766-1150; 764-1150; 776-1155; 766-1155; 764-1155; 776-1160; 766-1160; 764-1160; 776-1165; 766-1165; 764-1165; 776-1170; 766-1170; 764-1170; 776-1175; 766-1175; 764-1175; 776-1180; 766-1180; 764-1180; 776-1185; 766-1185; 764-1185; 776-1190; 766-1190; 764-1190; 776-1195; 766-1195; 764-1195; 776-1200; 766-1200; 764-1200; 776-1205; 766-1205; 764-1205; 776-1210; 766-1210; 764-1210; 776-1215; 766-1215; 764-1215; 776-1220; 766-1220; 764-1220; 776-1225; 766-1225; 764-1225; 776-1230; 766-1230; 764-1230; 776-1235; 766-1235; 764-1235; 776-1240; 766-1240; 764-1240; 776-1242; 766-1242; 764-1242; 764-1464; 764-1250; 764-1041; 764-828; 764-865; 764-1045; 764-1035; 764-1128; 764-1198; 764-1268; 764-1261; 764-1264; 764-1459; 764-1463; 764-1464; 764-1683; 764-1873; 764-1482; 764-1479; 764-1672; and 764-1874.

In certain embodiments the truncated VWF has an internal deletion relative to mature wild type VWF. For example one, more or all of the A1, A2, A3, D4, C1, C2, C3, C4, C5, C6, CK domains or combinations thereof are deleted, and the D' domain and/or the D3 domain is retained. According to further embodiments, the truncated VWF lacks one, more or all of the domains A1, A2, A3, D4, C1, C2, C3, C4, C5, C6 or CK. According to further embodiments, the truncated VWF lacks amino acids 1243 to 2813 of SEQ ID NO:4, i.e. the domains A1-A2-A3-D4-C1-C2-C3-C4-C5-C6-CK.

In further embodiments the truncated VWF does not comprise the binding sites for platelet glycoprotein Ibα (GPIbα), collagen and/or integrin αIIbβIII (RGDS sequence within the C1 domain). In other embodiments, the truncated VWF does not comprise the cleavage site (Tyr1605-Met1606) for ADAMTS13 which is located at the central A2 domain of VWF. In yet another embodiment, the truncated VWF does not comprise the binding sites for GPIbα, and/or does not comprise the binding site for collagen, and/or does not comprise the binding site for integrin αIIbβIII, and/or it does not comprise the cleavage site (Tyr1605-Met1606) for ADAMTS13 which is located at the central A2 domain of VWF.

In other embodiments the truncated VWF comprises or consists of an amino acid sequence that has a sequence identity of at least 90%, or at least 91%, or at least 92%, or at least 93%, or at least 94%, or at least 95%, or at least 96%, or at least 97%, or at least 98%, or at least 99%, to one of the amino acid sequences recited in the preceding paragraph, provided that the truncated VWF is capable of binding to FVIII.

A polypeptide of the invention is termed a "dimer" in the present invention if two monomers of polypeptide of the invention are linked covalently. Preferably, the covalent bond is located within the truncated VWF portion of the polypeptide of the invention. Preferably, the two monomeric subunits are covalently linked via at least one disulfide bridge, e.g. by one, two, three or four disulfide bridges. The cysteine residues forming the at least one disulfide bridge are preferably located within the truncated VWF portion of the polypeptide of the invention. In one embodiment, these cysteine residues are Cys-1099, Cys-1142, Cys-1222, Cys-1225, or Cys-1227 or combinations thereof. Preferably, the dimeric polypeptide of the invention does not comprise any further covalent bond linking the monomers in addition to said covalent bond located within the truncated VWF portion of the polypeptide, in particular does not comprise any further covalent bond located within the HLEM or HLEP portion of the polypeptide. According to alternative embodiments, however, the dimeric polypeptide of the invention may comprise a covalent bond located in the HLEM or HLEP portion of the polypeptide linking the monomers.

The dimer is preferably a homo-dimer, whereby each monomer comprises preferably a HLEM as disclosed herein. If the polypeptide of the invention is a dimer, the truncated VWF preferably comprises or consists of two polypeptides each with an amino acid sequence having a sequence identity of at least 90% to amino acids 764 to 1099, amino acids 764 to 1142, amino acids 764 to 1222, amino acids 764 to 1225, or amino acids 764 to 1227 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 764 to 1099, amino acids 764 to 1142, amino acids 764 to 1222, amino acids 764 to 1225, or amino acids 764 to 1227 of SEQ ID NO:4 and is capable of binding to FVIII. Most preferably, the truncated VWF comprises or consists of amino acids 764 to 1099, amino acids 764 to 1142, amino acids 764 to 1222, amino acids 764 to 1225, amino acids 764 to 1227 or amino acids 764 to 1242 of SEQ ID NO:4.

The truncated VWF may be any one of the VWF fragments disclosed in WO 2013/106787 A1, WO 2014/198699 A2, WO 2011/060242 A2, WO 2013/093760 A2 or WO 2016/188907 A1, the disclosure of which is incorporated herein by reference.

According to further preferred embodiments the truncated VWF as disclosed above may comprise at least one of the amino acid substitutions as disclosed in WO 2016/000039

A1. Those modified versions of the truncated VWF comprise at least one amino acid substitution within its D' domain, as compared to the amino acid sequence of the D' domain of wild-type VWF according to SEQ ID NO: 4. The amino acid sequence of the modified versions of the truncated VWF can have one or more amino acid substitutions relative to the respective wild type sequence. Those modified versions of the truncated VWF exhibit preferably a higher binding affinity to FVIII when compared to the binding affinity of a reference polypeptide which has the same amino acid sequence except for said modifications.

Unless indicated otherwise, the amino acid numbering of truncated VWF residues herein refers to SEQ ID NO:4, even if the truncated VWF molecule does not need to comprise all residues of SEQ ID NO:4.

The amino acid sequence of the D' domain of the modified truncated VWF preferably has one or 2 amino acid substitutions relative to the D' domain of SEQ ID NO:4. It is preferred that S at position 764 of SEQ ID NO:4, corresponding to position 1 of SEQ ID NO:2, is substituted with an amino acid selected from the group consisting of G, P, V, E, Y, A and L. It is also preferred that S at position 766 of SEQ ID NO:4, corresponding to position 3 of SEQ ID NO:2 is substituted with an amino acid selected from the group consisting of Y, I, M, V, F, H, R and W. Preferred combinations of substitutions include S764G/S766Y, S764P/5766I, S764P/S766M, S764V/S766Y, S764E/S766Y, S764Y/S766Y, S764L/S766Y, S764P/S766W, S766W/S806A, S766Y/P769K, S766Y/P769N, S766Y/P769R and S764P/S766L, referring to the sequence of SEQ ID NO:4. The binding affinity of the polypeptide of the present invention to FVIII may be further increased by introduction of said substitutions compared to the binding affinity of a reference polypeptide which has the same amino acid sequence except for said modifications. As the interaction of VWF with FVIII typically has a high on-rate, changes in the dissociation constant is largely dependent on changes in the off-rate. Accordingly the main focus in increasing the association of VWF with FVIII involves efforts to decrease the offrate between FVIII and VWF. Preferably the off-rate of the truncated VWF variants having said modifications and FVIII in comparison to wild type VWF and FVIII is at least two fold lower, more preferably at least 5 fold lower, preferably at least 10 fold lower and more preferably at least 20 fold lower. Said substitutions within the truncated VWF may contribute to increase the half-life of co-administered FVIII and/or may allow for reduction of the to be administered dose of the recombinant polypeptide of the invention.

According to further preferred embodiments the truncated VWF as disclosed herein may comprise at least one of the amino acid substitutions as described in copending PCT/AU2017/050010 A1. Those modified versions of the truncated VWF exhibit preferably a higher binding affinity to FVIII when compared to the binding affinity of a reference polypeptide which has the same amino acid sequence except for said modifications. Thus, the truncated VWF as disclosed herein may comprise one of the following amino acid substitutions or combination of amino acid substitutions: S764P/S766W/V1083A, S764G/S766Y/V1083A, S764E/S766Y/V1083A, N1011S/V1083A/K1181E, S766Y/V1083A, V1083A, 51042T, V805A/Q1158L, K912E/T1088S, or L781P. Said substitutions within the truncated VWF may contribute to increase the half-life of co-administered FVIII and/or may allow for reduction of the to be administered dose of the recombinant polypeptide of the invention.

Polypeptides of the invention having said substitutions can preferably be used to ensure a further increased half-life of co-administered FVIII and simultaneously provide reduced immunogenicity of FVIII, even in case only a moderate molar excess of the polypeptide of the invention over co-administered FVIII is applied.

The term "endogenous VWF" as used herein refers to monomeric subunits of VWF, independent of its degree of di- or oligomerization.

Half-Life Extending Moiety (HLEM)

In addition to the truncated VWF, the polypeptide of the invention may in certain preferred embodiments further comprise a half-life extending moiety (HLEM). The half-life-extending moiety may be a heterologous amino acid sequence, particularly a half-life enhancing protein (HLEP). Alternatively, the half-life-extending moiety may be a non-peptidic moiety chemically conjugated to the polypeptide comprising the truncated VWF by a covalent bond different from a peptide bond.

In certain embodiments of the invention, the half-life of the recombinant polypeptide of the invention is extended by chemical modification, e.g. attachment of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the polypeptide of the invention is conjugated to a HLEP such as albumin via a chemical linker. The principle of this conjugation technology has been described in an exemplary manner by Conjuchem LLC (see, e.g., U.S. Pat. No. 7,256,253).

The recombinant polypeptide further comprises preferably a chemical bond or a linker sequence positioned between the truncated VWF and the HLEM or HLEP.

Said linker sequence may be a peptidic linker consisting of one or more amino acids, in particular of 1 to 50, 1 to 30, 1 to 20, 1 to 15, 1 to 10, 1 to 5 or 1 to 3 (e.g. 1, 2 or 3) amino acids and which may be equal or different from each other. Preferably, the linker sequence is not present at the corresponding position in the wild-type VWF. Preferred amino acids present in said linker sequence include Gly and Ser. The linker sequence should be non-immunogenic. Preferred linkers may be comprised of alternating glycine and serine residues. Suitable linkers are described for example in WO2007/090584.

In another embodiment of the invention the peptidic linker between the truncated VWF moiety and the HLEM consists of peptide sequences, which serve as natural inter-domain linkers in human proteins. Preferably such peptide sequences in their natural environment are located close to the protein surface and are accessible to the immune system so that one can assume a natural tolerance against this sequence. Examples are given in WO 2007/090584. Cleavable linker sequences are described, e.g., in WO 2013/120939 A1.

In a preferred embodiment of the recombinant polypeptide the linker between the truncated VWF and the HLEM is a glycine/serine peptidic linker having or consisting of amino acid sequence 480-510 of SEQ ID NO:2.

In one embodiment the polypeptide has the following structure:

$$tVWF-L1-H, \tag{I}$$

wherein tVWF is the truncated VWF, L1 is a chemical bond or a linker sequence, and H is a HLEM, in particular a HLEP.

L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type VWF. Examples of suitable amino acids present in L1 include Gly and Ser. The linker should be non-immunogenic and may be a non-cleavable or cleavable linker. Non-cleavable linkers may be comprised of alternating glycine and serine residues as exemplified in WO2007/090584. In another embodiment of the invention the peptidic linker between the truncated VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584. Cleavable linker sequences are described, e.g., in WO 2013/120939 A1.

Preferred HLEP sequences are described infra. Likewise encompassed by the invention are fusions to the exact "N-terminal amino acid" or to the exact "C-terminal amino acid" of the respective HLEP, or fusions to the "N-terminal part" or "C-terminal part" of the respective HLEP, which includes N-terminal deletions of one or more amino acids of the HLEP. The polypeptide may comprise more than one HLEP sequence, e.g. two or three HLEP sequences. These multiple HLEP sequences may be fused to the C-terminal part of VWF in tandem, e.g. as successive repeats.

Half-Life Enhancing Polypeptides (HLEPs)

Preferably, the half-life extending moiety is a half-life extending polypeptide (HLEP). One or more HLEPs may be fused to the C-terminal part of VWF provided that they do not to interfere with or abolish the binding capability of the truncated VWF to FVIII. More preferably HLEP is selected from polypeptides capable of binding to the neonatal Fc receptor (FcRn), such as albumin or fragments thereof, or immunoglobulin constant regions and portions thereof, e.g. the Fc fragment, solvated random chains with large hydrodynamic volume (e.g. XTEN (Schellenberger et al. 2009; Nature Biotechnol. 27:1186-1190), homo-amino acid repeats (HAP), proline-alanine-serine repeats (PAS), afamin, alpha-fetoprotein, Vitamin D binding protein, transferrin or fragments thereof, carboxyl-terminal peptide (CTP) of human chorionic gonadotropin-R subunit, polypeptides or lipids capable of binding under physiological conditions to albumin or immunoglobulin constant region. The immunoglobulin constant region or portions thereof is preferably a Fc fragment of immunoglobulin G1, a Fc fragment of immunoglobulin G2 or a Fc fragment of immunoglobulin A.

A "half-life enhancing polypeptide" as used herein is preferably selected from the group consisting of albumin, a member of the albumin-family, the constant region of immunoglobulin G and fragments thereof, region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to the respective polypeptide without the HLEP.

The HLEP portion of the polypeptide of the invention may be a variant of a wild type HLEP. The term "variants" includes insertions, deletions and substitutions, either conservative or non-conservative, where such changes do not substantially alter the FVIII-binding activity of the truncated VWF.

In particular, the proposed VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

According to certain embodiments of present disclosure the HLEM, in particular a HLEP, portion of the recombinant polypeptide of the invention may be specified with the alternative term "FP". Preferably, the term "FP" represents a human albumin.

According to certain preferred embodiments, the recombinant polypeptide is a fusion protein. A fusion protein in terms of present invention is a protein created by in-frame joining of at least two DNA sequences encoding the truncated VWF as well as the HLEP. The skilled person understands that translation of the fusion protein DNA sequence will result in a single protein sequence. As a result of an in frame insertion of a DNA sequence encoding a peptidic linker according to a further preferred embodiment, a fusion protein comprising the truncated VWF, a suitable linker and the HELP may be obtained.

According to some embodiments, the co-administered FVIII does neither comprise any of the herein described HLEM or HLEP structures. According to certain other embodiments, the co-administered FVIII may comprise at least one of the herein described HLEM or HLEP structures.

Albumin as HELP

Preferably, the HLEP is an albumin or a fragment thereof. The N-terminus of the albumin may be fused to the C-terminus of the truncated VWF. Alternatively, the C-terminus of the albumin may be fused to the N-terminus of the truncated VWF.

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:6 herein or albumin from other vertebrates or fragments thereof, or analogs or variants of these molecules or fragments thereof.

According to certain embodiments of present disclosure the alternative term "FP" is used to identify the HLEP, in particular to define albumin as HLEP.

According to a further preferred embodiment the recombinant polypeptide of the invention comprising the truncated VWF comprises or consists of the amino acid sequence as defined in SEQ ID NO:2.

In particular, the proposed polypeptides of the invention may include naturally occurring polymorphic variants of human albumin and fragments of human albumin. Generally speaking, an albumin fragment or variant will be at least 10, preferably at least 40, most preferably more than 70 amino acids long.

Preferred embodiments of the invention include albumin variants used as a HLEP of the polypeptide of the invention with enhanced binding to the FcRn receptor. Such albumin variants may lead to a longer plasma half-life of a truncated VWF albumin variant fusion protein as compared to a truncated VWF fusion with a wild-type albumin. Variants include those described in WO 2014072481, WO 2012150319, WO 2013135896, WO 2011124718, WO 2011051489 and WO 2012059486, the disclosures of which are incorporated by cross-reference. The albumin portion of the polypeptides of the invention may comprise at least one subdomain or domain of HA or conservative modifications thereof.

Immunoglobulins as HLEPs

In a further preferred embodiment, the HLEP may be an immunoglobulin constant region (Fc). Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

Various HLEPs which can be used in accordance with this invention are described in detail in WO 2013/120939 A1.

N-Glycans and Sialylation of the Polypeptide of the Invention

The polypeptide of the invention preferably comprises N-glycans, and at least 75%, preferably at least 85%, more preferably at least 90% of said N-glycans comprise, on average, at least one sialic acid moiety. In preferred embodiments, at least 91%, at least 92%, at least 93%, at least 94%, at least 95%, at least 96%, at least 97%, at least 98%, or at least 99%, of said N-glycans comprise, on average, at least one sialic acid moiety. The inventors found that polypeptides comprising highly sialylated VWF fragments not only may have a further prolonged half-life themselves, but may also be capable to extend the half-life of co-administered FVIII further. In other words, administration of the polypeptide of the invention leads to an extended half-life and/or to a reduced clearance of co-administered FVIII.

The polypeptide of the invention preferably comprises N-glycans, and at least 50% of the sialyl groups of the N-glycans of the glycoproteins are $\alpha$-2,6-linked sialyl groups. In general, terminal sialyl groups can be attached to the galactose groups via a $\alpha$-2,3- or via a $\alpha$-2,6-linkage. Typically, N-glycans of the polypeptide of the invention comprise more $\alpha$-2,6-linked sialyl groups than $\alpha$-2,3-linked sialyl groups. Preferably, at least 60%, or at least 70%, or at least 80%, or at least 90% of the sialyl groups of the N-glycans are $\alpha$-2,6-linked sialyl groups. These embodiments can be obtained by, e.g., co-expressing human $\alpha$-2,6-sialyltransferase in mammalian cells.

Suitable methods of producing such glycoproteins are described in WO2016/188905 A1. Accordingly, a method of producing a glycoprotein comprising N-glycans with increased sialylation is described therein, which method comprises (i) providing cells comprising a nucleic acid encoding a polypeptide comprising a truncated von Willebrand Factor (VWF), and (ii) culturing said cells at a temperature of less than 36.0° C. In addition, a method of producing a dimer of a glycoprotein comprising a truncated von Willebrand Factor (VWF), or for increasing the dimerization of said glycoprotein is described, which method comprises (i) providing cells comprising a nucleic acid encoding the amino acid sequence of the glycoprotein, and (ii) culturing said cells at a temperature of less than 36.0° C. Further, a method of producing a glycoprotein comprising N-glycans with increased sialylation is described therein, which comprises (i) providing cells comprising a nucleic acid encoding a polypeptide comprising a truncated von Willebrand Factor (VWF) and a recombinant nucleic acid encoding an $\alpha$-2,6-sialyltransferase, and (ii) culturing the cells under conditions that allow expression of the glycoprotein and of the $\alpha$-2,6-sialyltransferase.

In one embodiment, at least 85%, at least 90%, at least 95%, at least 96%, at least 97%, at least 98%, or at least 99%, of the N-glycans of the polypeptide of the invention comprise at least one sialic acid group. In another embodiment, at least 90%, at least 95%, at least 96%, at least 97%, at least 98%, or at least 99%, of the N-glycans of the polypeptide of the invention comprise at least one sialic acid group.

In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they are N-glycans lacking a sialic acid group. In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they do not have a sialic acid group.

Other embodiments of the invention comprise a truncated von Willebrand Factor (VWF), wherein said truncated VWF is capable of binding to a Factor VIII (FVIII), and wherein said glycoprotein comprises N-glycans, wherein less than 35%, preferably less than 34%, preferably less than 33%, preferably less than 32%, preferably less than 31%, preferably less than 30%, preferably less than 29%, preferably less than 28%, preferably less than 27% preferably less than 26%, preferably less than 25%, preferably less than 24%, preferably less than 23%, preferably less than 22%, preferably less than 21%, preferably less than 20%, preferably less than 19%, preferably less than 18%, preferably less than 17%, preferably less than 16%, preferably less than 15%, preferably less than 14%, preferably less than 13%, preferably less than 12%, preferably less than 11%, preferably less than 10%, preferably less than 9%, preferably less than 8%, preferably less than 7%, preferably less than 6% and preferably less than 5% of said N-glycans comprise, on average, two or more terminal and non-sialylated galactose residues.

Still other embodiments of the invention comprise a truncated von Willebrand Factor (VWF), wherein said truncated VWF is capable of binding to a Factor VIII (FVIII), and wherein said truncated VWF comprises N-glycans, wherein less than 6%, preferably less than 5%, preferably less than 4%, preferably less than 3%, preferably less than 2%, and preferably less than 1% of said N-glycans comprise, on average, three or more terminal and non-sialylated galactose residues.

The above-described embodiments can be combined with each other. Any percentages of N-glycans mentioned above, or any indications of the degree of sialylation, are to be understood as average percentages or degrees, i.e. they refer to a population of molecules, not to a single molecule. It is clear that the glycosylation or sialylation of the individual glycoprotein molecules within a population of glycoproteins will show some heterogeneity.

Dimers

The polypeptides of this invention have a high proportion of dimers. The polypeptide of the invention is therefore preferably present as dimer. In one embodiment, at least 50%, or at least 60%, or at least 70%, or at least 80%, or at least 90%, or at least 95% or about 100% of the polypeptides are present as dimers. In another embodiment, the ratio dimer:monomer of the polypeptide of the invention is at least 1.5, preferably at least 2, more preferably at least 2.5 or at least 3. Most preferably all polypeptides of the invention are present as dimers. Further preferred is that polypeptide of the invention does not comprise multimeric forms. The use of dimers is favorable, as the dimer has an improved affinity to Factor VIII as compared to the monomer. The dimer content, and the ratio of dimer to monomer of the polypeptide of the invention can be determined as described in Example 2 of WO 2016/188907, herein incorporated by reference.

In one embodiment, the affinity of the polypeptide of the invention to Factor VIII is greater than that of human native VWF to the same Factor VIII molecule. The Factor VIII affinity may refer to human native Factor VIII, or to the Factor VIII molecule characterized by SEQ ID NO:5.

It has been found that preparations of the polypeptide of this invention with a high proportion of dimers do have an increased affinity to Factor VIII. Such increased affinity to Factor VIII does lead to an enhanced stabilization of Factor VIII by the polypeptides of the present invention. Alternatively to or in combination with an increased dimer proportion also polypeptides in accordance with the invention with mutations within the Factor VIII binding domain which do increase the affinity to Factor VIII are preferred embodiments of the invention. Suitable mutations are disclosed herein.

Preparation of the Polypeptide

The nucleic acid encoding the polypeptide of the invention can be prepared according to methods known in the art. Based on the cDNA sequence of pre-pro form of human native VWF (SEQ ID NO:3), recombinant DNA encoding the above-mentioned truncated VWF constructs or polypeptides of the invention can be designed and generated.

Even if the polypeptide which is secreted by the host cells does not comprise amino acids 1 to 763 of pre-pro form of human native VWF, it is preferred that the nucleic acid (e.g. the DNA) encoding the intracellular precursor of the polypeptide comprises a nucleotide sequence encoding an amino acid sequence having a sequence identity of at least 95%, at least 96%, at least 97%, at least 98%, or at least 99%, to amino acids 23 to 763 or preferably to amino acids 1 to 763 of SEQ ID NO:4. Most preferably, the nucleic acid (e.g. the DNA) encoding the intracellular precursor of the polypeptide comprises a nucleotide sequence encoding amino acids 23 to 763 of SEQ ID NO:4, or amino acids 1 to 763 of SEQ ID NO:4.

Constructs in which the DNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Typically, the cells to be provided are obtained by introducing the nucleic acid encoding a polypeptide of the invention into mammalian host cells.

Any host cell susceptible to cell culture, and to expression of glycoproteins, may be utilized in accordance with the present invention. In certain embodiments, a host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243 251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB 8065); mouse mammary tumor (MMT 060562, ATCC CCL51); TRI cells (Mather et al., Annals NY. Acad. Sci., 383:44-68, 1982); MRC 5 cells; PS4 cells; human amniocyte cells (CAP); and a human hepatoma line (Hep G2). Preferably, the cell line is a rodent cell line, especially a hamster cell line such as CHO or BHK.

Methods suitable for introducing nucleic acids sufficient to achieve expression of a glycoprotein of interest into mammalian host cells are known in the art. See, for example, Gething et al., Nature, 293:620-625, 1981; Mantei et al., Nature, 281:40-46, 1979; Levinson et al. EP 117,060; and EP 117,058. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in U.S. Pat. No. 4,399,216. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988.

The cells are cultured under conditions that allow expression of the polypeptide. The polypeptide can be recovered and purified using methods that are known to the skilled artisan.

Treatment of Coagulation Disorder

The recombinant polypeptide comprising a truncated VWF as described above is used for reducing the immunogenicity of FVIII, wherein the recombinant polypeptide and a FVIII protein are coadministered to a subject suffering from a blood coagulation disorder. In particular, the blood coagulation disorder includes hemophilia A. The term "hemophilia A" refers to a deficiency in functional coagulation FVIII, which is usually inherited.

In one embodiment, the blood coagulation disorder is severe hemophilia A, preferably associated with an endogenous FVIII activity level that is below 1% of the endogenous FVIII activity level in NHP. In terms of present invention, the blood coagulation disorder preferably is severe hemophilia A.

In another embodiment, the blood coagulation disorder is moderate hemophilia A. Moderate hemophilia A is preferably characterized by an endogenous FVIII activity level which is from about 1% to about 5% of the endogenous FVIII activity level in NHP. Typically, subjects having moderate hemophilia A have an endogenous FVIII activity level from 0.01 to 0.05 IU/mL in plasma.

In another embodiment, the blood coagulation disorder is mild hemophilia A. Mild hemophilia A is preferably characterized by an endogenous FVIII activity level which is from about 5% to about 40% of the endogenous FVIII activity level in NHP. Typically, subjects having mild hemophilia A have an endogenous FVIII activity level from 0.05 to 0.4 IU/mL in plasma.

Treatment of a blood coagulation disorder encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom a polypeptide of the invention is administered preferably is a human. In certain aspects, the human is a pediatric patient. In other aspects, the human is an adult patient.

In certain embodiments, the subject is expected to and/or has a risk to develop an immune reaction against FVIII.

In certain embodiments, the subject is a subject being previously untreated with FVIII.

In other embodiments, the subject is a subject having been pre-treated with FVIII, e.g. a subject which is subjected to a treatment change from a first FVIII product to a second different FVIII product, in particular from treatment with cryoprecipitate and/or fresh frozen plasma to treatment with a factor concentrate, or from treatment with a plasma-derived factor concentrate to a recombinant factor concentrate or from a first manufacturer's FVIII concentrate to another manufacturer's FVIII concentrate. The treatment change is according to certain embodiments also encompassing a change from a FVIII concentrate only administration to a treatment including an administration of FVIII in conjunction with the recombinant polypeptide of the invention.

In particular embodiments, the subject has a risk for developing an immune reaction against FVIII, particularly an immune reaction characterized by inhibitory antibodies against FVIII. Several types of such risk factors for the development of inhibitory anti-FVIII antibodies in patients, in particular in patients with hemophilia A, following FVIII administration are known. For example, the subject may exhibit a genotype characterized by inversions, large deletions and/or nonsense mutations of the FVIII gene that eliminate or substantially eliminate endogenous production of FVIII in said subject. Thus certain types of F8 gene mutation have been identified to be associated with a genetic risk factor. Further genetic risk factors comprise polymorphisms in IL10, TNFA, FCGR2A or CTLA4.

In certain embodiments, coadministration of the recombinant polypeptide with FVIII is prophylactic, e.g. in a situation where the subject suffering from a blood coagulation disorder as described supra is undergoing a continuous treatment comprising regular coadministration of the recombinant polypeptide and FVIII.

In other embodiments, coadministration may be therapeutic, e.g. under circumstances wherein the subject suffering from a blood coagulation disorder experiences an acute bleeding episode or has the risk of experiencing an acute bleeding episode.

Compositions and kits comprising a polypeptide of the invention as well as compositions and kits comprising a polypeptide of the invention and FVIII are described herein. The compositions typically are supplied as part of a sterile, pharmaceutical composition that includes a pharmaceutically acceptable carrier. This composition can be in any suitable form (depending upon the desired method of administering it to a patient).

The term "Factor VIII" and "FVIII" or "Factor VIII protein" are used interchangeably herein and encompass both plasma derived FVIII and recombinant FVIII. Recombinant FVIII encompasses without limitation full-length FVIII as well as two-chain B-domain deleted or truncated variants as well as single-chain B-domain deleted or truncated variants for example those described in WO 2004/067566 and other FVIII variants with mutations outside the B-domain but having the biological activity of FVIII. According to one preferred embodiment the FVIII is a single-chain Factor VIII consisting of the amino acid sequence of SEQ ID NO:5.

The polypeptide of the invention can be administered to a patient by a variety of routes such as orally, transdermally, subcutaneously, intradermally, intranasally, intravenously, intraperitoneally, intramuscularly, sublingually, topically or locally. The most suitable route for administration in any given case will depend on the particular polypeptide, the subject, and the nature and severity of the disease and the physical condition of the subject. Preferably, a polypeptide of the invention will be administered intravenously or subcutaneously. The polypeptide and the FVIII are preferably co-administered.

Determination of the total number of doses and length of treatment with a polypeptide of the invention and FVIII is well within the capabilities of those skilled in the art. The dosage of the polypeptide of the invention as well as FVIII to be administered depends on the concentrations of the FVIII to be administered, the concentration of endogenous VWF in the patient to be treated, or both. An effective dosage based on the ratios defined by the inventors of this application can be determined by the skilled person, taking into account the molecular weight of the polypeptide of the invention as well as the molecular weight of the FVIII to be administered. The degree of severity of the blood coagulation disorder may also be considered to determine the appropriate dosage of the polypeptide of the invention as well as of FVIII to be administered. Typical dosages for FVIII may range from about 20 IU/kg body weight to about 1000 IU/kg body weight, preferably from about 20 IU/kg body weight to about 500 IU/kg body weight, further preferred from about 20 IU/kg body weight to about 400 IU/kg body weight, more preferred from about 20 IU/kg body weight to about 300 IU/kg body weight.

In accordance with this invention, the patient being treated with the polypeptide of the invention is also or at least has been treated with blood coagulation Factor VIII. The polypeptide of the invention and the FVIII may be administered simultaneously, i.e. together, or in a sequential fashion. Alternatively, an administration in a separate fashion can be performed. All of said modes of administration herein are encompassed by the term "combination therapy" and "co-administration".

According to a certain embodiment, the polypeptide of the invention and the FVIII may be administered as a mixture, i.e. either within the same composition or following a mixing step of two compositions; or may be administered sequentially or separately, i.e. as separate compositions.

Co-administration of the recombinant polypeptide and the FVIII protein is according to one preferred embodiment achieved by administration together in a single composition comprising the recombinant polypeptide and the FVIII protein. According to further preferred embodiments, co-administration of the recombinant polypeptide and the FVIII protein is achieved by providing a combination product comprising the recombinant polypeptide and the FVIII blended in a single composition or by providing a set or kit of at least two separate products arranged to be mixed before administration, whereby a first product comprises the recombinant polypeptide and a second product comprises the FVIII. Said combination product is particularly suited for simultaneous administration. Said set or kit is particularly suited for simultaneous administration or sequential administration.

According to a certain embodiment, the polypeptide of the invention and the FVIII may be administered separately, i.e. as separate compositions and, if appropriate, at different dosing schedules. Preferably, the polypeptide of the invention and the FVIII may be administered in conjunction. The administration schedule for the polypeptide of the invention may be identical to the administration schedule of FVIII or may be different. One can recognize that in particular according to this embodiment the co-presence in vivo of both, the polypeptide of the invention and the FVIII, at least transiently is more important than the mode of administration. An identical dosing regimen is not crucial for the polypeptide of the invention to have its benefit to reduce the FVIII immunogenicity as long as administered in conjunction. Thus, the administration with regard to the dosing regime and/or route of administration of the polypeptide of the invention and the FVIII could be provided independently as long as a co-presence in vivo is achieved. According to this embodiment, a composition comprising the polypeptide of the invention, but not comprising any FVIII, may be particularly suitable, since FVIII is provided and administered independently, however, preferably in conjunction with the polypeptide of the invention.

In particular, in case that the recombinant polypeptide and the FVIII protein are provided in separate compositions or products to be mixed prior to co-administration, the mixture may be treated before administration in such a manner to allow prior to administration for at least a proportion of said recombinant polypeptide to bind to said FVIII. For example, the mixture could be incubated for a certain time. Such incubation could be conducted in less than 1 min, or less than 5 min at either ambient temperature or, if appropriate, at elevated temperature, however, preferably at a temperature below 40° C. Such a quick incubation step may also be appropriate during reconstitution for a combination product comprising the recombinant polypeptide and the FVIII blended in a single composition.

The concentration of Factor VIII in the composition used is typically in the range of 10-10,000 IU/mL. In different embodiments, the concentration of FVIII in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, or 1,000 IU/mL, or 800 IU/mL, or 750 IU/mL, or 600 IU/mL, or 500 IU/mL, or 400 IU/mL, or 300 IU/mL, or 250 IU/mL, or 200 IU/mL, or 150 IU/mL, or 125 IU/mL, or 100 IU/mL, or 62.5 IU/mL, or 50 IU/mL, provided the requirements regarding the ratio with respect to the VWF polypeptide of the invention as defined herein are fulfilled.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated in "IU" against an international standard preparation. One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the coamatic FVIII test kit (Chromogenix-Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of $Ca^{2+}$, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

Pharmaceutical Compositions

Therapeutic formulations of the polypeptide of the invention suitable in the methods described herein can be prepared for storage as lyophilized formulations or aqueous solutions by mixing the polypeptide having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to a polypeptide of the invention. Examples of suitable second therapeutic agents are provided below.

The dosing schedule can vary from once a month to daily depending on a number of clinical factors, including the type of disease, severity of disease, and the patient's sensitivity to the polypeptide of the invention. In specific embodiments, a polypeptide of the invention is administered, twice weekly, every 5 days, once weekly, every 10 days, every two weeks, every three weeks, every four weeks or once a month, or in any range between any two of the foregoing values, for example from every four weeks to every month, from every 10 days to every two weeks, or from two to three times a week, etc.

The dosage of a polypeptide of the invention to be administered will vary according to the particular polypeptide, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of a polypeptide of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

The pharmaceutical composition is preferably formulated to be administered extravascularly, preferably to be administered subcutaneously.

According to a certain embodiment, the pharmaceutical composition comprises as active component either both, the polypeptide of the invention as well as a FVIII, or alternatively comprises only the polypeptide of the invention without any FVIII depending on the herein disclosed mode of administration.

Those skilled in the art will appreciate that the invention described herein is susceptible to variations and modifications other than those specifically described. It is to be understood that the invention includes all such variations and modifications which fall within the spirit and scope. The invention also includes all of the features, compositions, steps, and compounds referred to or indicated in this specification, individually or collectively and any and all combinations of any two or more of said features, compositions, steps, and compounds.

The nucleotide and amino acid sequences shown in the sequence listing are summarized in the Table 1.

TABLE 1

| SEQ ID NO: | Remarks |
|---|---|
| 1 | DNA sequence encoding a polypeptide comprising acids 1 to 1242 of human VWF, a glycine/serine linker and human albumin; nucleotide positions (nt): nt 1-6: EcoRI restriction enzyme cleavage site nt 32-3757: coding sequence for VWF amino acids 1 to 1242 nt 3758-3850: coding sequence for glycine/serine linker nt 3851-5608: coding sequence for human albumin nt 5609-5616: NotI restriction enzyme cleavage site |
| 2 | Amino acid sequence encoded by SEQ ID NO: 1 (mature form): amino acid positions (aa): aa 1-479: VWF D'D3 region (VWF amino acids 764-1242) aa 480-510: glycine/serine linker aa 511-1095: human albumin |
| 3 | DNA sequence encoding the pre-pro form of human native VWF |
| 4 | Amino acid sequence encoded by SEQ ID NO: 3 |
| 5 | Amino acid sequence of a single chain Factor VIII molecule |
| 6 | Amino acid sequence of mature human serum albumin |

Certain embodiments of the invention will now be described with reference to the following examples which are intended for the purpose of illustration only and are not intended to limit the scope of the generality hereinbefore described.

EXAMPLES

Example 1

Levels of Factor VIII Uptake by Monocyte Derived Dendritic Cells when Treated with Plasma Derived VWF and Recombinant Truncated VWF 1.1 Definitions/Abbreviations

| Term/Abbreviation | Description |
|---|---|
| Ab | Antibody |
| mAb | Monoclonal Antibody |
| IgG | Immunoglobulin |
| rVWF | Recombinant Von Willebrand Factor |
| PBMC | Peripheral Blood Mononuclear Cell |
| RBC | Red Blood Cell |
| MDDC | Monocyte derived dendritic cell |
| BDD | B domain deleted |
| PBS | Phosphate-buffered saline |
| BSA | Bovine Serum Albumin |
| FBS | Fetal Bovine Serum |

1.2 Materials and Methods

BIOSTATE (human plasma derived (pd) VWF from CSL Behring)
CSL626 (truncated VWF (764-1242)-albumin fusion, dimer)
CSL650 (rec. VWF-albumin fusion from CSL Behring)
CSL627 (rec. single chain FVIII from CSL Behring)
Advate® (rec. FVIII from Shire)
Helixate® (rec. FVIII from CSL Behring)
ReFacto® (rec. FVIII from Pfizer)

Generation of D'D3 albumin fusion protein (D'D3-FP), also specified herein as truncated VWF-albumin fusion CSL 626, as well as characterisation of D'D3-FP dimer binding to FVIII has been disclosed in WO 2016/188907 A1 which is incorporated herein by reference. The nucleotide sequence of the coding sequence D'D3-FP is displayed as SEQ ID NO:1, the amino acid sequence of the mature D'D3-FP is shown as SEQ ID NO:2.

The recombinant B-Domain-deleted single chain FVIII (CSL627), i.e. rVIII-SingleChain, has an amino acid sequence as defined in SEQ ID NO:5.

CSL650 (rec. VWF-albumin fusion) has an amino acid sequence as described in WO 2009/156137 A1.

1.3 Uptake of FVIII in Monocyte Derived Dendritic Cells

A whole buffy coat was decanted into a 50 ml falcon tube and diluted 1:2 with sterile PBS (Sigma #D8537, 25 ml blood/25 ml PBS). The blood was mixed and layered onto a Ficoll gradient, (GE, #17-1440-02) containing 15 ml of Ficoll. The gradient was separated by centrifugation at 1000×g (accel (5); brake (1)), for 20 minutes. The central layer containing PBMCs was collected and transferred into a fresh 50 ml collection tube.

The cells were then pelleted by centrifugation (1400 rpm) and washed two times with 50 ml of sterile PBS, decanting the supernatant each time. The pellet was then resuspended in ammonium chloride (10 ml) and incubated at room temperature (RT) for 10 min to lyse remaining RBCs. After lysis, the cells were topped up with 40 ml of PBS and spun down to pellet the remaining PBMCs. The cells were washed once more with 50 ml of PBS and spun down (1200 rpm) to collect final cell pellet. The cell pellet was resuspended into 20 ml of PBS and cells were counted using a haemocytometer to prepare for monocyte purification.

$2\times10^8$ PBMCs were taken and pelleted by centrifugation (1200 rpm, 10 min, 4° C.). The cell pellet was resuspended in 1600 µl of purification buffer, (PBS pH 7.2, 0.5% BSA (Miltenyi Biotec #130-091-376), 2 mM EDTA). CD14 microbeads (Miltenyi Biotec #130-050-201) were then added to the cells (400 µl) and incubated for 15 min at 4° C. After the incubation, the cells were washed with ice cold purification buffer (20 ml) and pelleted once again by centrifugation (1200 rpm, 10 min, 4° C.). The supernatant was aspirated completely and resuspended with ice cold purification buffer (500 µl).

The cells were run through a 70 µm cell strainer to remove clumpy cells and then added directly onto an equilibrated MACS LS column (Miltenyi Biotec #130-041-401). The column was washed 3 times with 3 ml of purification buffer to remove unbound cells. The MACS column was then removed from the magnet and 5 ml of purification buffer was added to the column. The cells were decanted by pressure through a syringe and pelleted by centrifugation (1200 rpm, 5 min).

The cells were resuspended in complete growth media, (RPMI 1640 (Sigma #R0883) supplemented with 10% FBS (GE #SV30176.03), 50 U/ml Penicillin and 50 µg/ml Streptomycin (Pen-Strep, Gibco #15070-63), 2 mM Glutamax (Gibco #35050) and counted. Cells were plated on a petri dish ($1 \times 10^7$ cells/dish), and cytokines were added to the cells to induce differentiation (500 IU IL-4/$10^6$ cells, 1000 IU GM-CSF/$10^6$ cells, R&D Systems, 204-IL-010/CF/215-GM-050/CF). The plates were left to incubate at 37° C., 5% $CO_2$. On day three the cells were topped up with cytokines in 5 ml of fresh complete media (500 IU IL-4/$10^6$ cells, 1000 IU GM-CSF/$10^6$ cells).

After day 5 the cultured cells were removed from each plate and pelleted by centrifugation, (1200 rpm, 10 min). The cells were then washed once with pre-warmed XVIVO media (LONZA #04-743Q), resuspended in XVIVO media (2 ml) and counted. Cells were characterised by flow cytometry for expression of CD14 (BD Biosciences CD14-V450, #560349), CD40 (BD Biosciences, CD40-PE, #555589), CD86 (BD Biosciences, CD86-PE, #555658) and HLA-DR (BD Biosciences, HLA-DR-PE, #347401). The cells were then plated in a 96-well round bottom plate, ($2.5 \times 10^5$ cells/well). The cells prepared for 37° C. analysis were placed into an incubator (37° C., 5% $CO_2$), and the plates to be used as a 4° C. baseline control were placed on ice.

The VWF proteins were diluted in a volume of 50 µl and added to the wells. The dilutions were made to achieve final concentrations of 2222 nM, 1111 nM, 555.5 nM, and 0 nM for pdVWF and CSL650, based on monomeric subunit, and 4444 nM, 2222 nM and 1111 nM for CSL626 based on the monomeric subunit. After a 10-minute pre-incubation of the VWF proteins, the FVIII proteins were also diluted, (88.88 nM final) and added to each corresponding well. The plates were left to incubate for 2 hours to allow factor VIII uptake.

After incubation, the plates were spun to pellet cells, (1200 rpm, 5 min) and the supernatant was discarded. The wells were washed twice with FACS buffer, (PBS+2% FBS, GE #SV30176.03) and then resuspended in 100 µl of Intrapep Reagent 2 (Beckman Coulter, #IM2389) to fix the cells. Cells were left to fix at RT for 15 minutes, then spun down (1200 rpm, 5 min) and the supernatant was discarded. The cells were washed with 200 µl of FACS buffer, and resuspended with 100 µl of Intrapep Reagent 2 (Beckman Coulter, #IM2389) to permeabilize the cells. The cells were left to incubate at RT for 5 minutes, then treated with 10 µg/ml of anti-factor VIII A2 antibody (Thermo Fisher #MA1-27389) for 15 minutes. The cells were then pelleted and washed with FACS wash and stained with a secondary antibody (Jackson #115-115-164, Anti-mouse IgG, 50 µl, 1:100 dilution) for 15 minutes at RT in the dark. After incubation, the cells were washed twice with FACS buffer and analysed by flow cytometry.

1.4 Data Analysis

Using flowjo, cells were gated on single MDDCs by FSC and SSC, a baseline quadrant was set on MDDCs not treated with either Factor VIII or VWF. Positive migration above the baseline quadrant was represented as a percentage and final values were determined by subtracting the 4° C. uptake for equivalent treatments. The final percentage of migration was plotted using prism against the corresponding ratio of VWF uptake.

1.5 Results

Surface marker phenotyping of the MDDCs showed a negative staining for CD14 and positive stains for CD40, HLA-DR and CD86 (FIG. 1).

Figure 2:
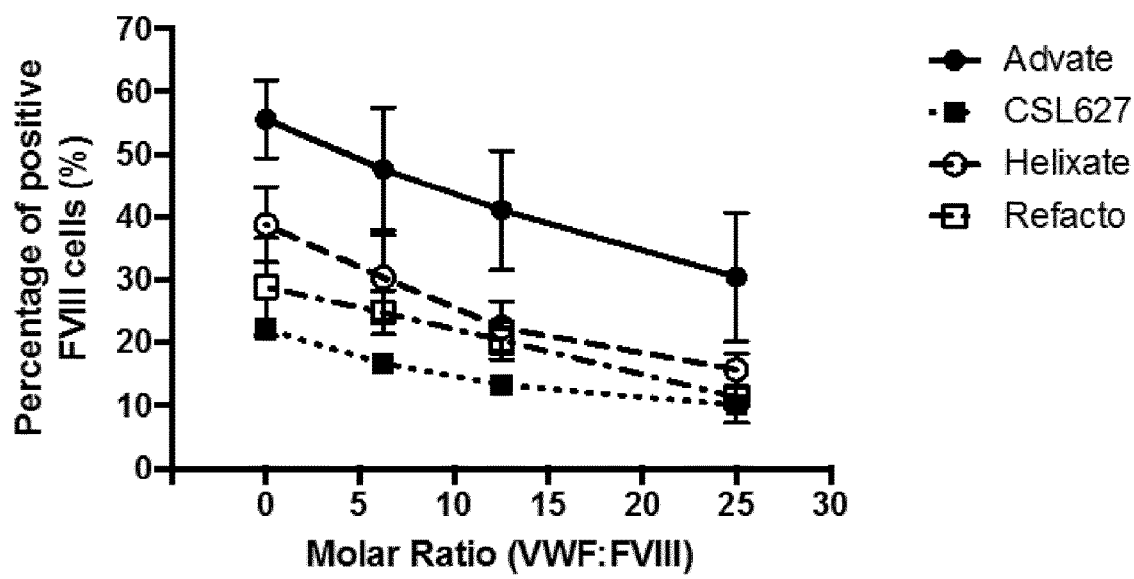
FIG. 2 shows VWF Inhibition of factor VIII uptake in MDDCs: commercial FVIII proteins (Advate, Helixate and Refacto) and rec scFVIII (CSL 627) were evaluated for uptake in the presence of the pdVWF product Biostate (a), the truncated VWF-albumin fusion CSL 626 (b) and the full-length recVWF-albumin fusion CSL 650 (c). The percentage of FVIII uptake in MDDCs of four different FVIII products, Advate, CSL 627, Helixate and Refacto, are plotted separately against an increasing molar ratio of VWF: FVIII. The molar ratios VWF:FVIII refer to the monomeric subunit for the different VWF products. Experiments were done in triplicate (a) or quadruplicate (b) and (c), respectively.
Figure 2:
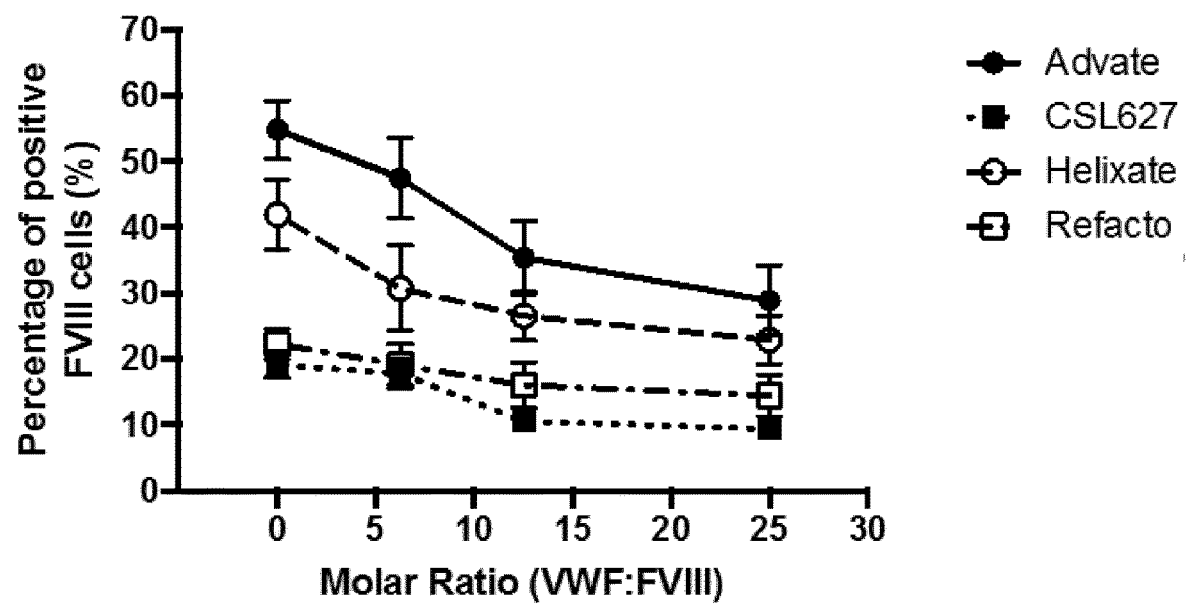
Figure 2:
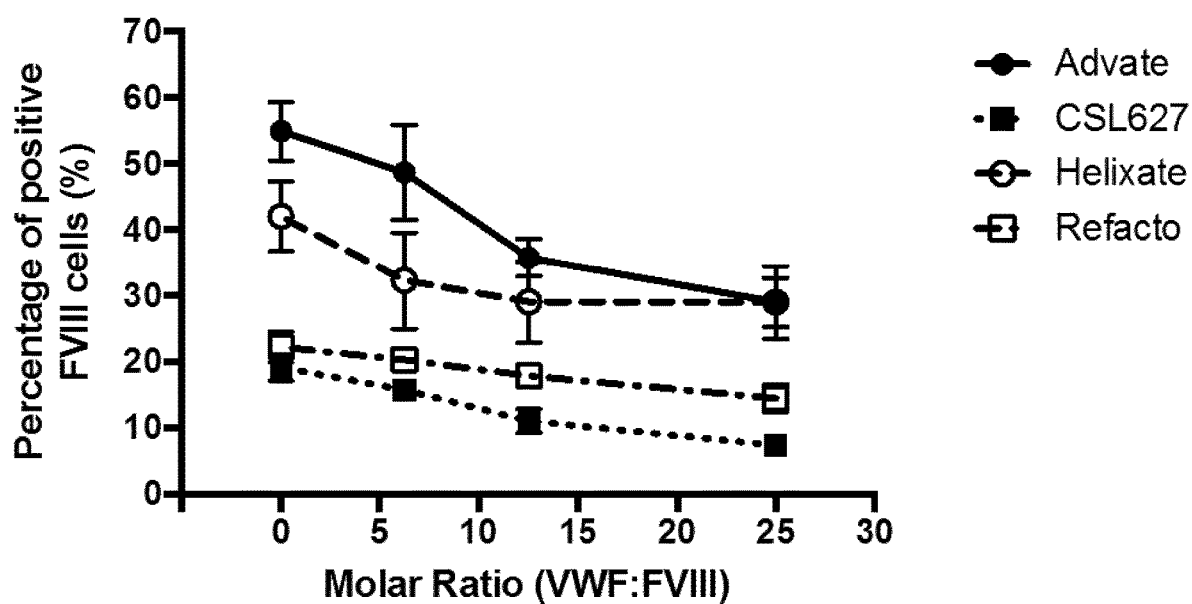
Figure 3:
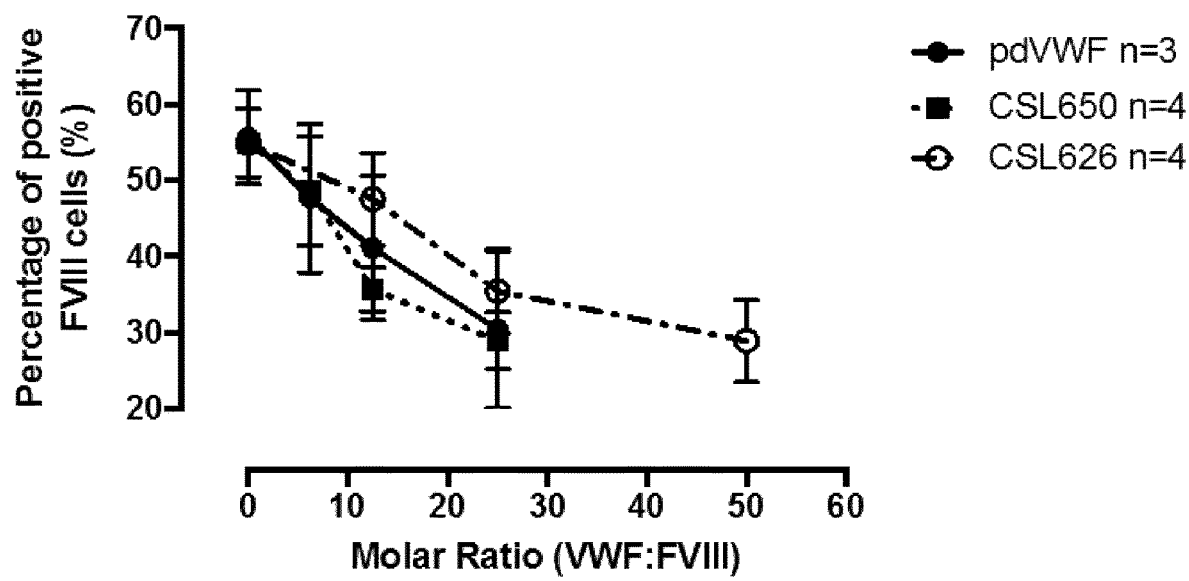
FIG. 3 shows VWF Inhibition of factor VIII uptake in MDDCs: Different VWF proteins (the pdVWF product Biostate, the truncated VWF-albumin fusion CSL 626 and the full-length recVWF-albumin fusion CSL 650) were evaluated for inhibition of FVIII uptake in MDDCs. The percentage of FVIII uptake in MDDCs of four different FVIII products, Advate (a), CSL 627 (b), Helixate (c) and Refacto (d) are plotted separately against an increasing molar ratio of VWF:FVIII. The molar ratios VWF:FVIII refer to the monomeric subunit for the different VWF products.
Figure 3:
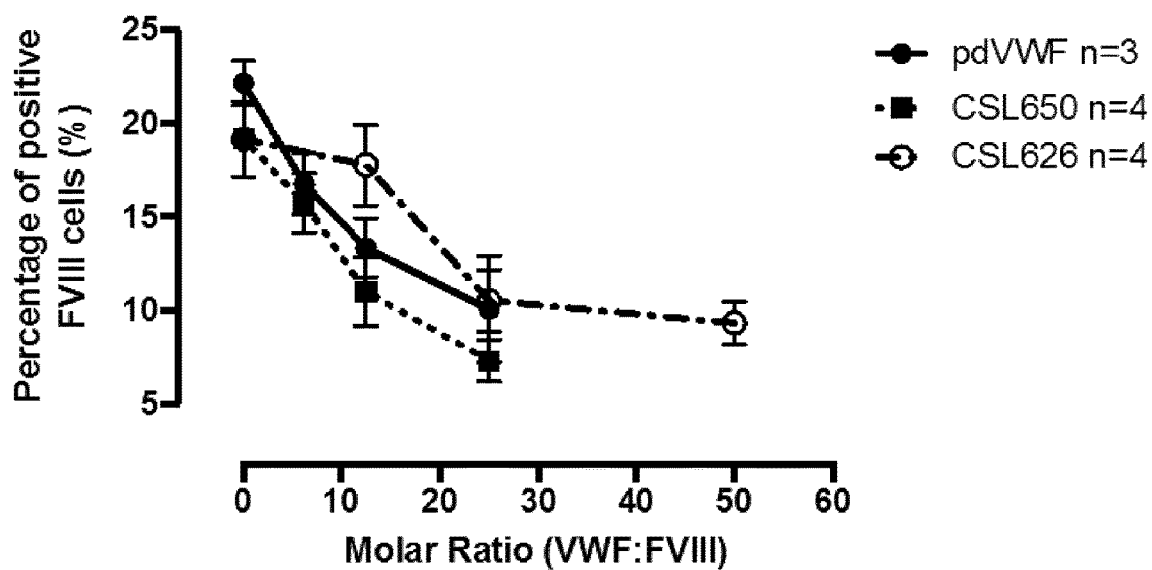
Figure 3:
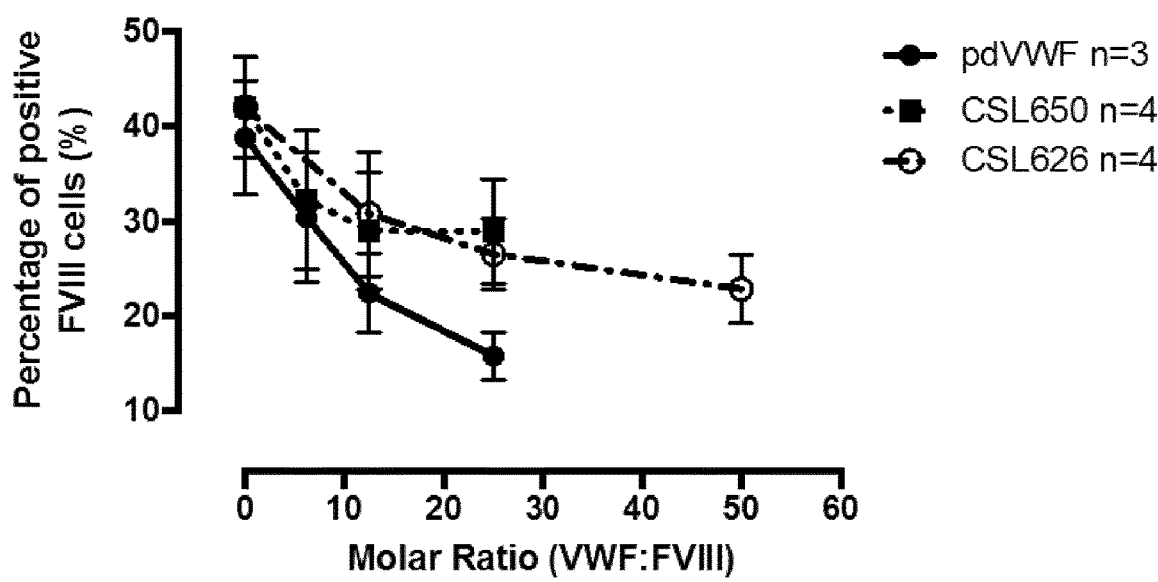
Figure 3:
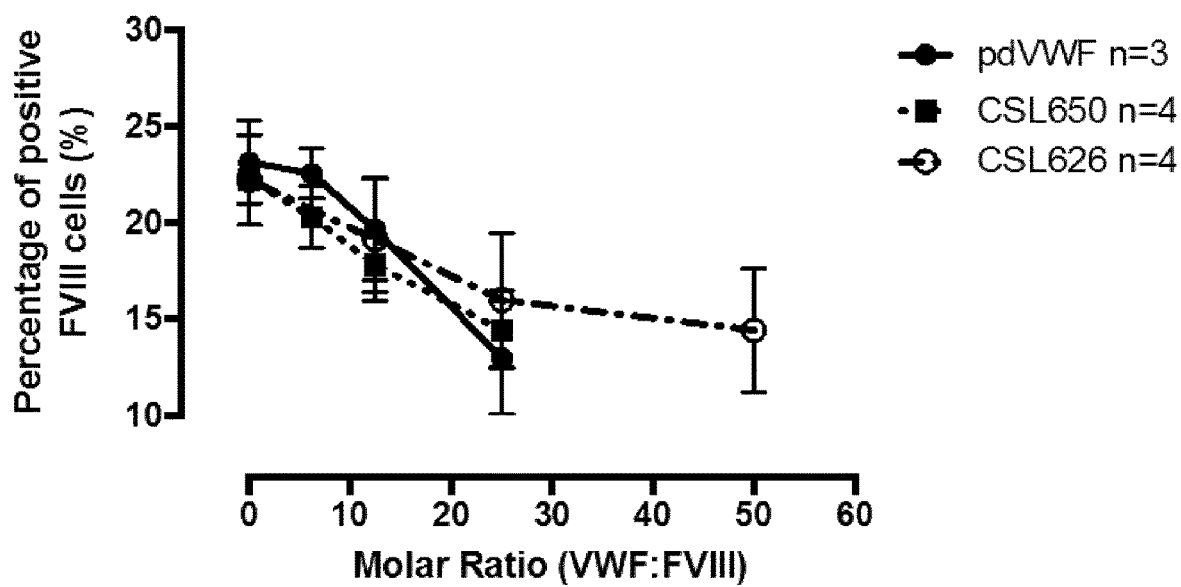

FIGS. 2 and 3 show the percentage of factor VIII uptake in MDDCs. Three commercially available FVIII proteins (Advate®, Helixate® and Refacto®) and rec scFVIII (CSL 627) were evaluated for uptake in the presence of the pdVWF product Biostate, the truncated VWF-albumin fusion CSL 626 and the full-length recVWF-albumin fusion CSL 650. Different molar ratios of VWF:FVIII were applied. The VWF concentrations refer to the monomeric subunit for the different VWF products. Factor VIII uptake was evaluated in the absence of VWF (molar ratio of VWF:FVIII=0) up to a 25-fold molar excess of the pdVWF product Biostate and the full-length recVWF-albumin fusion CSL 650 and up to a 50-fold molar excess of the truncated VWF-albumin fusion CSL 626.

FIG. 2 shows the results in three individual panels for the pdVWF product Biostate (a), the truncated VWF-albumin fusion CSL 626 (b) and the full-length recVWF-albumin fusion CSL 650 (c). Results of three commercial FVIII proteins (Advate®, Helixate® and Refacto®) and rec scFVIII (CSL 627) are plotted separately in each panel. FIG. 3 represent the data of FIG. 2 in a different arrangement. Four individual panels for Advate® (a), CSL 627 (b), Helixate® (c) and Refacto® (d) show the results of FVIII uptake in MDDCs in presence of increasing molar ratios of VWF:FVIII. In each panel the pdVWF product Biostate, the truncated VWF-albumin fusion CSL 626 and the results of the full-length recVWF-albumin fusion CSL 650 are plotted separately.

The FVIII uptake in MDDCs was reduced for all factor VIII proteins when the molar ratio of VWF:FVIII was increased using the pdVWF product Biostate, the truncated VWF-albumin fusion CSL 626 as well as the full-length recVWF-albumin fusion CSL 650.

Figure 4:
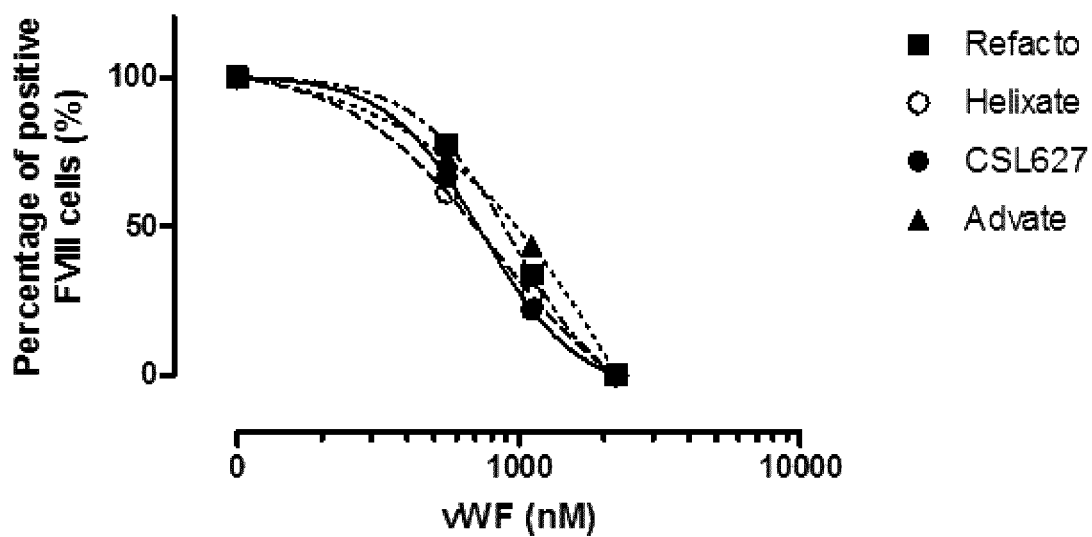
FIG. 4 shows Normalized curves of VWF Inhibition of factor VIII uptake in MDDCs: commercial FVIII proteins (Advate®, Helixate® and Refacto®) and rec scFVIII (CSL 627) were evaluated for uptake in the presence of the pdVWF product Biostate (a), the truncated VWF-albumin fusion CSL 626 (b) and the full-length recVWF-albumin fusion CSL 650 (c). The VWF concentrations refer to the monomeric subunit for the different VWF products. Experiments were done in triplicate (a) or quadruplicate (b) and (c), respectively. The data was normalized for each individual experiment. The readout in the absence of VWF (0 nM) was defined as 100% and the readout in presence of the highest VWF concentration (2222 nM or 4444 nM) was defined with 0% for each individual experiment. Curves were fitted using GraphPad Prism Software (log(inhibitor) vs. response—Variable slope, four parameters, least squares ordinary fit). Based on these fitted curves, IC50 values for the respective VWF proteins have been calculated and summarized in Table 2.
Figure 4:
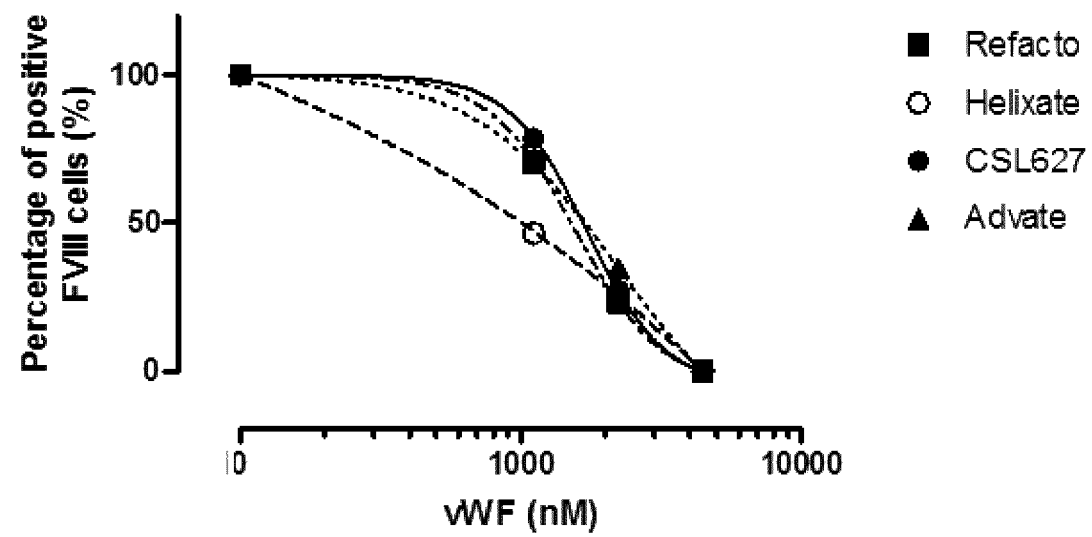
Figure 4:
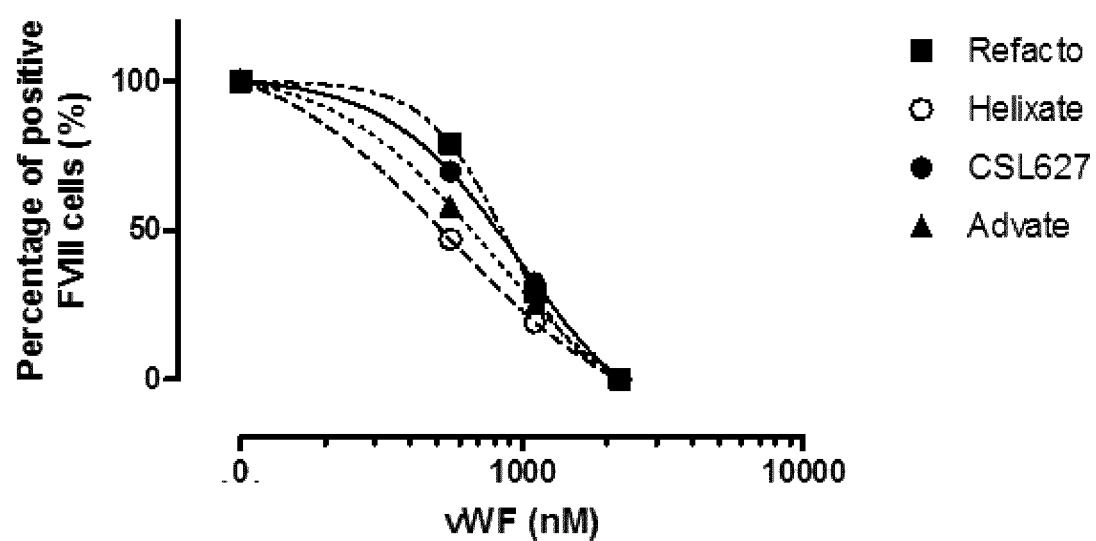

FIG. 4 shows the normalized percentage of factor VIII uptake in MDDCs based on the data shown in FIG. 2. Three individual panels for the pdVWF product Biostate (a), the truncated VWF-albumin fusion CSL 626 (b) and the full-length recVWF-albumin fusion CSL 650 (c) show the results of three commercial FVIII proteins (Advate®, Helixate® and Refacto®) and rec scFVIII (CSL 627) separately. Data was plotted against the molar VWF concentration. The VWF concentrations refer to the monomeric subunit for the different VWF products. The data was normalized for each individual experiment. Experiments were done in triplicate (a) or quadruplicate (b) and (c), respectively. The readout in the absence of VWF (0 nM) was defined as 100% and the readout in presence of the highest VWF concentration (2222 nM or 4444 nM) was defined with 0% for each individual experiment. Negative values as well as outliers were excluded after normalization. Curves were fitted using GraphPad Prism Software (log(inhibitor) vs. response—Variable slope, four parameters, least squares ordinary fit) and IC50 values calculated. Based on these fitted curves, IC50 values for the respective VWF products have been calculated and summarized in Table 2.

TABLE 2

Calculated IC$_{50}$ values of VWF proteins for inhibition of factor VIII uptake in MDDCs

|  | Advate® | CSL627 | Helixate® | Refacto® | all FVIII | std. dev. |
|---|---|---|---|---|---|---|
| pdVWF | ambiguous fit | 744 nM | 823 nM | 963 nM | 843 nM | +/−111 nM |
| CSL626 | 2226 nM | 1718 nM | 1692 nM | 1569 nM | 1801 nM | +/−291 nM |
| CSL650 | 769 nM | 750 nM | 552 nM | 778 nM | 712 nM | +/−107 nM |

Table 2 shows the calculated IC$_{50}$ values for inhibition of factor VIII uptake in MDDCs. IC50 values for each FVIII product, Advate®, CSL 627, Helixate® and Refacto®, were calculated separately for the three different VWF proteins pdVWF/Biostate, CSL 626 and CSL 650 (FIG. 4). A mean and standard deviation of the IC$_{50}$ for all FVIII was also calculated separately for three different VWF proteins. IC$_{50}$ for all FVIII products tested in presence of the truncated VWF-albumin fusion CSL 626 was only moderately increased compared with the pdVWF product Biostate and the full-length recVWF-albumin fusion CSL 650.

The results shown in FIG. 2, in FIG. 3 and in Table 2 demonstrate that pdVWF, full-length rec VWF, but surprisingly also truncated VWF albumin fusion CSL 626 were able to inhibit endocytosis of different FVIII products into monocyte dendritic cells at similar rates. Increasing VWF concentrations showed an increase in reduction of FVIII uptake for both full-length and BDD FVIII products.

Notably, the IC50 value for the tested truncated VWF albumin fusion CSL 626 compares at least similarly with the IC50 values of the full-length VWF products tested.

Since uptake of FVIII by antigen-presenting cells such as monocyte dendritic cells is the first step of an immune reaction against administered FVIII, the results demonstrate a reduction of FVIII immunity by administering the truncated VWF-albumin fusion CSL 626 which is present as a dimer. The quantitative reduction of cellular uptake mediated by CSL 626 compared to full-length VWF products is surprisingly strong.

Example 2

Factor VIII Antigen Presentation by Monocyte Derived Dendritic Cells when Treated with Plasma Derived VWF and Recombinant Truncated VWF

2.1 Definitions/Abbreviations

| Term/Abbreviation | Description |
|---|---|
| CD209 | Cluster of differentiation, surface marker expressed on the surface of immature dendritic cells (DCs) |
| CD86 | luster of differentiation, surface marker expressed on the surface of antigen-presenting cells |
| DC | dendritic cell |
| GM-CSF | granulocyte macrophage colony-stimulating factor |
| HLA | human leukocyte antigen |
| HLA-DPB1 | HLA class II histocompatibility antigen, DPB1 beta chain |
| HLA-DQB1 | HLA class II histocompatibility antigen, DQB1 beta chain |
| HLA-DR | HLA class II heterodimer, alpha and beta chain |
| HLA-DRB1 | HLA class II histocompatibility antigen, DRB1 beta chain |
| IL-4 | interleukin 4 |

-continued

| Term/Abbreviation | Description |
|---|---|
| LC-MS/MS | Liquid chromatography-mass spectrometry |
| LPS | lipopolysaccharides |
| MHC-II | major histocompatibility complex class II |
| MODC | monocyte-derived dendritic cells |
| PBMC | Peripheral Blood Mononuclear Cell |

2.2 Materials and Methods

Plasma-derived von Willebrand Factor (pdVWF): The source of pdVWF is human plasma. Residual plasma-derived FVIII bound to pdVWF was separated from the concentrate intermediate through a size exclusion chromatography step (HiPrep Sephacryl S500, GE Healthcare) using a HEPES buffer containing 400 nM Calcium (Josica D. et al. Journal of Chromatography (1998); 796(2), p. 289-298).

CSL627 (rec. single chain FVIII from CSL Behring): is a recombinant B-Domain-deleted single chain FVIII, i.e. rVIII-SingleChain, having an amino acid sequence as defined in SEQ ID NO:5. CSL626 (truncated VWF (764-1242)-albumin fusion, dimer) was used as described under Example 1. A variant of CSL626 was used having a further increased binding affinity to FVIII having amino acid substitutions compared to the VWF wild-type amino acid sequence when referring to the sequence numbering of SEQ ID NO:4, the substitution being S764E/S766Y/V1083A. This D'D3-FP variant is also referred to as EYA-FP in Example 2.

2.3 ProPresent Antigen Presentation Assay

The ProPresent assay was performed by Proimmune (Oxford, U.K.) to identify unique CSL627 and pdVWF, CSL626 or EYA-FP peptides bound to HLA molecules in monocyte-derived dendritic cells (MODC) following antigen uptake and processing. Test antigens (CSL627, pdVWF, CSL626 and EYA-FP) were prepared by us.

Figure 5:
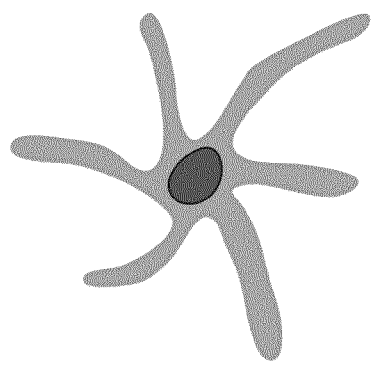
FIG. 5 shows ProImmune's workflow of the ProPresent® MHC class II antigen presentations assay: (A) Isolated Monocytes of HLA-typed PBMCs, (B) Culturing of Monocytes and generation of immature dendritic cells, (C) Antigen Loading (CSL627, pdVWF), intracellular processing, maturation of dendritic cells and antigen presentation (D) Lysis of dendritic cells, (E) Isolation of peptide/MHC class II complexes by immunoaffinity step and elution of peptides, (F) Sequencing of peptides by LC-MS$^2$ (adapted from ProImmune ProPresent® homepage)
Figure 5:
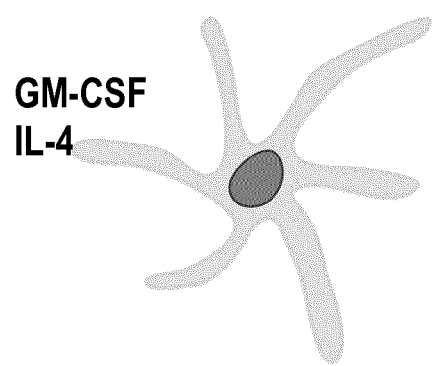
Figure 5:
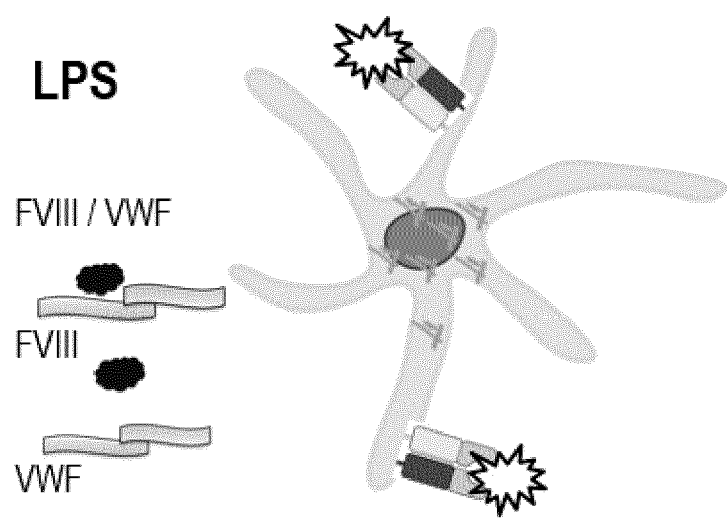
Figure 5:
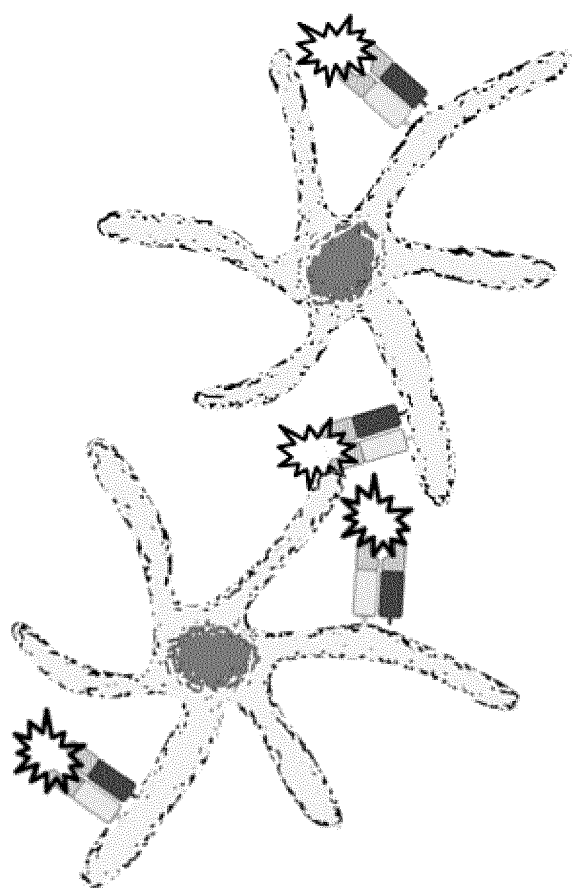
Figure 5:
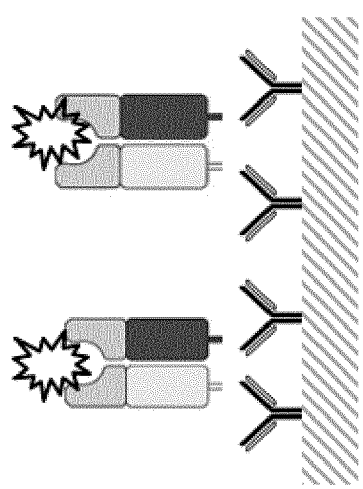
Figure 5:
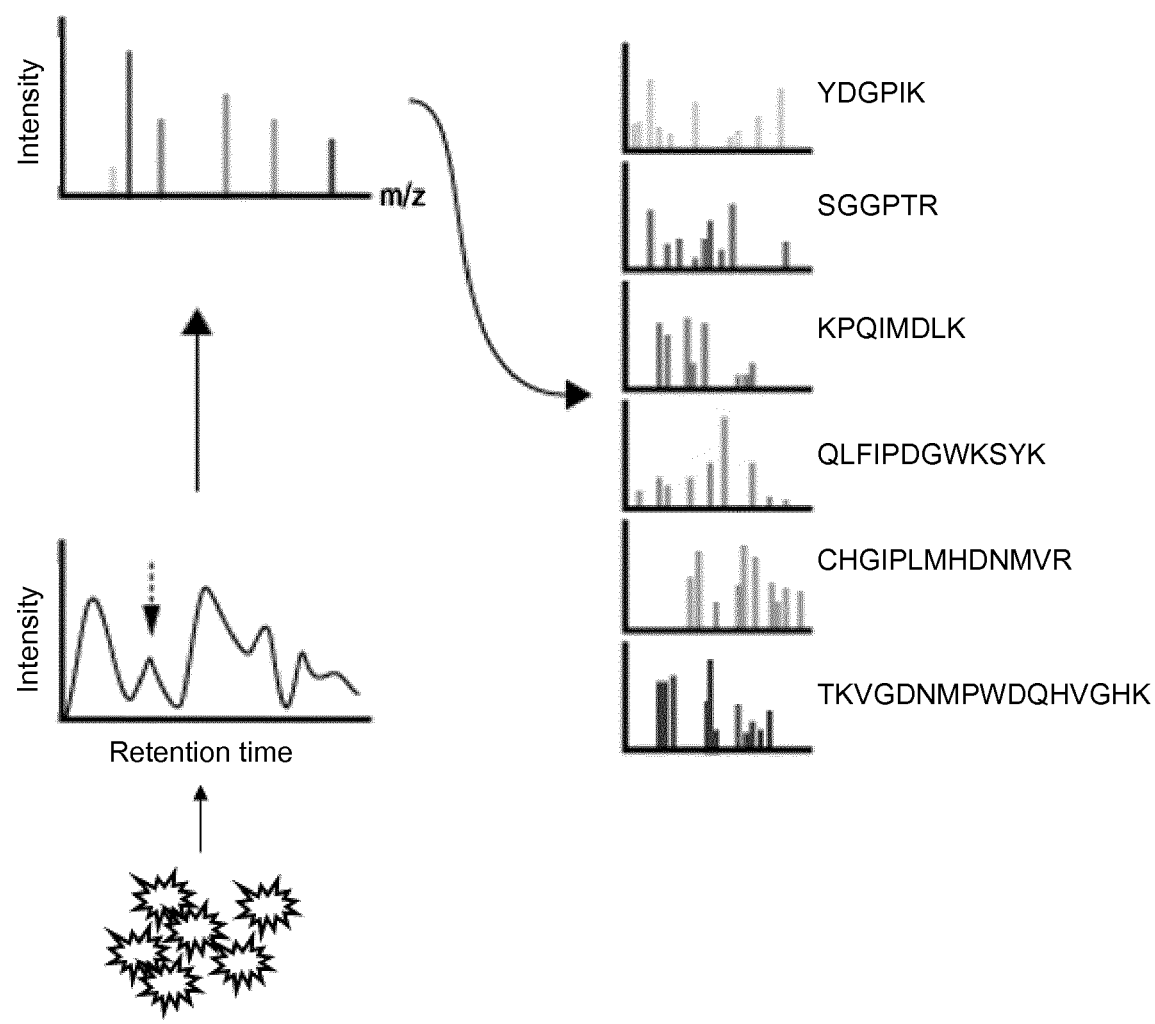
Figure 6:
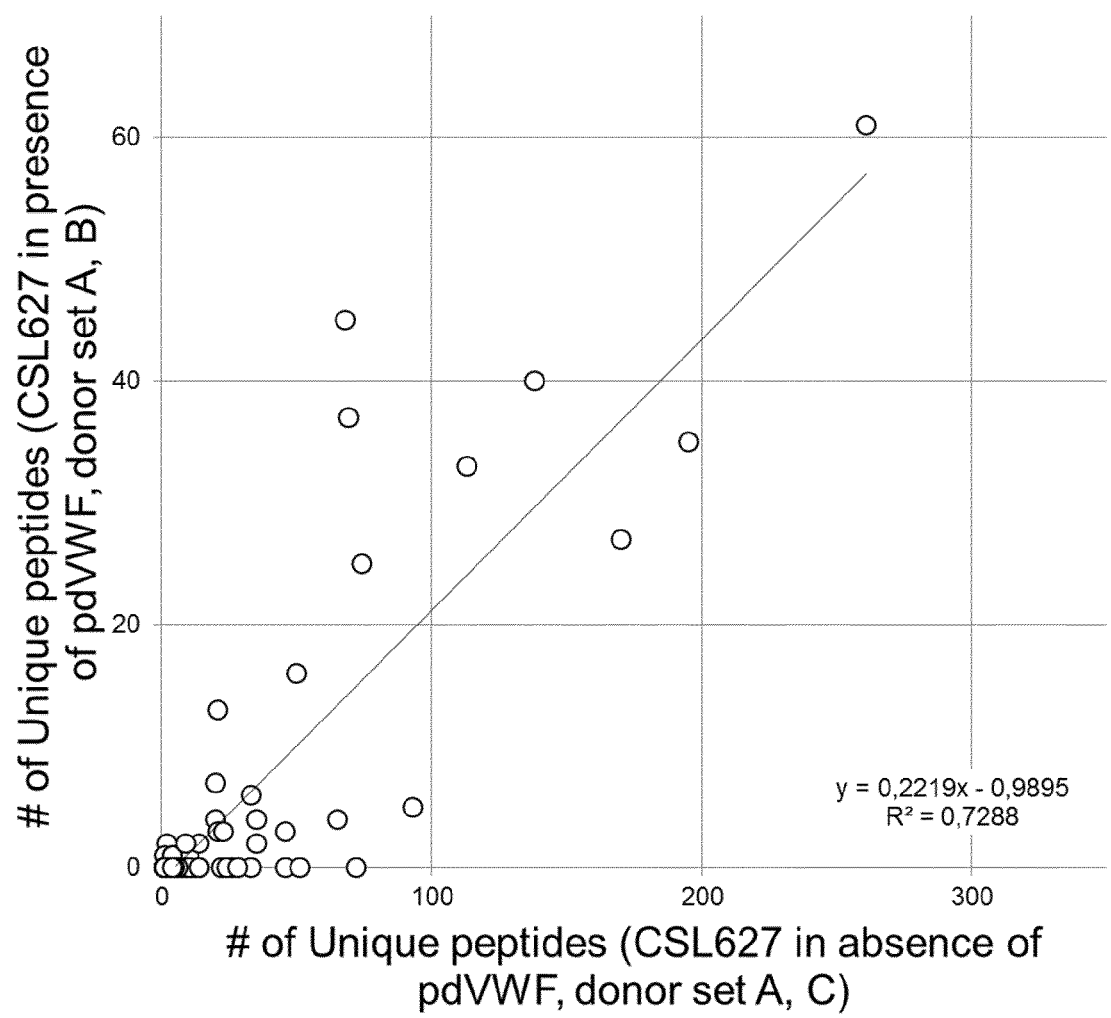
FIG. 6 shows a comparison of ProImmune ProPresent® Antigen presentation of CSL627 in presence and absence of pdVWF: each data point represents a HLA-DR restricted peptide cluster; the number of CSL627-derived, unique HLA-DR bound peptides of HLA-DR restricted peptide clusters was plotted in absence (X-Axis) and presence (Y-Axis) of pdVWF. X-Y-Plot, linear regression (MS Excel)

Briefly, PBMCs from 12 to 24 HLA-typed healthy unrelated donors (table 3-5) were purified from whole blood by gradient density centrifugation. Immature monocyte-derived DCs (MODCs) were generated in vitro and matured in the presence of 146.4 nM CSL627 only or in the presence of 146.4 nM CSL627 pre-complexed with 1.9667 μM pdVWF, CSL626 or EYA-FP (molar concentrations were calculated based on monomer content). Maturation of MODCs is monitored by flow cytometry through upregulated CD209, CD86 and HLA-DR. MODCs were harvested and washed prior to lysis in a detergent-containing buffer solution. HLA molecules were recovered in a specific immunoaffinity step. Peptides were then eluted from the purified HLA complexes and processed for further analysis. Peptide samples were subsequently analysed by high-resolution sequencing mass spectrometry (LC-MS/MS), see FIG. 5. The resulting data were then compiled and analysed using sequence analysis software referencing the Uniprot Swiss-Prot Complete Human Proteome Database with the incorporated test antigen sequences as well as peptides derived from six endogenous control proteins, Lysosome-Associated Membrane Protein 1 (LAMP-1), Lysosome-Associated Membrane Protein 3 (LAMP-3), Transferrin receptor (TFRC), Low affinity IgE receptor and Fc gamma binding receptors (FcER2/FcGR2), Apolipoprotein B (ApoB) and Integrin α-M (ITGAM). MHC class II associated invariant chain peptide (CLIP) is downregulated and may not be detected in fully matured MODCs. Identification of peptide sequences by LC-MS/MS was based on scoring algorithms and statistical significance determination. The likelihood of peptides to be real identities is described by their expected values. (Xue L, Clin Exp Immunol. (2016); 183(1):102-13, Leone D A J Immunol (2017), 199 (2) 531-546, Lamberth et al., Sci. Transl. Med. 9, eaag1286 (2017)). FIG. 5 shows ProImmune's workflow of the ProPresent® MHC class II antigen presentations assay: (A) Isolated Monocytes of HLA-typed PBMCs, (B) Culturing of Monocytes and generation of immature dendritic cells, (C) Antigen Loading (CSL627, pdVWF), intracellular processing, maturation of dendritic cells and antigen presentation (D) Lysis of dendritic cells, (E) Isolation of peptide/MHC class II complexes by immunoaffinity step and elution of peptides, (F) Sequencing of peptides by LC-MS$^2$ (adapted from ProImmune ProPresent® homepage).

2.4 Data Analysis

All identified peptides are grouped and aligned for each donor. A group of overlapping peptides imbedded in one alignment defines a peptide cluster at a certain amino acid position of tested proteins. Core peptides of identified peptide clusters are predicted using NetMHCII 3.1. The core peptide with the highest predicted binding affinity is used to indicate the location of that specific peptide cluster. The number of all peptide clusters in a set of donors is used to quantify antigen presentation efficiency and as score for potential immunogenicity, respectively, for a corresponding test protein. The total count of unique peptides in all peptide clusters for each donor is also taken into account to quantify antigen presentation strengths (see example below).

Example for Data Analysis:

1  $X_{01}-X_{02}-X_{03}-X_{04}-X_{05}-X_{06}-X_{07}-X_{08}-X_{09}-X_{10}-X_{11}-X_{12}-X_{13}-X_{14}-X_{15}-X_{16}-X_{17}-X_{18}-X_{19}-X_{20}$

2  $X_{02}-X_{03}-X_{04}-X_{05}-X_{06}-X_{07}-X_{08}-X_{09}-X_{10}-X_{11}-X_{12}-X_{13}-X_{14}-X_{15}-X_{16}$

3  $X_{03}-X_{04}-X_{05}-X_{06}-X_{07}-X_{08}-X_{09}-X_{10}-X_{11}-X_{12}-X_{13}-X_{14}-X_{15}-X_{16}$

4  $X_{04}-X_{05}-X_{06}-X_{07}-X_{08}-X_{09}-X_{10}-X_{11}-X_{12}-X_{13}-X_{14}-X_{15}-X_{16}-X_{17}-X_{18}$

5  $X_{05}-X_{06}-X_{07}-X_{08}-X_{09}-X_{10}-X_{11}-X_{12}-X_{13}-X_{14}-X_{15}-X_{16}-X_{17}-X_{18}-X_{19}-X_{20}$

6  $X_{06}-X_{07}-X_{08}-X_{09}-X_{10}-X_{11}-X_{12}-X_{13}-X_{14}-X_{15}-X_{16}-X_{17}-X_{18}-X_{19}-X_{20}$

7  $X_{07}-X_{08}-X_{09}-X_{10}-X_{11}-X_{12}-X_{13}-X_{14}-X_{15}-X_{16}-X_{17}-X_{18}-X_{19}-X_{20}$

8  $X_{01}-X_{02}-X_{03}-X_{04}-X_{05}-X_{06}-X_{07}-X_{08}-X_{09}-X_{10}-X_{11}-X_{12}-X_{13}-X_{14}-X_{15}-X_{16}$

9  $X_{04}-X_{05}-X_{06}-X_{07}-X_{08}-X_{09}-X_{10}-X_{11}-X_{12}-X_{13}-X_{14}-X_{15}-X_{16}$

10 $X_{04}-X_{05}-X_{06}-X_{07}-X_{08}-X_{09}-X_{10}-X_{11}-X_{12}-X_{13}-X_{14}-X_{15}-X_{16}-X_{17}-X_{18}$

11 $X_{05}-X_{06}-X_{07}-X_{08}-X_{09}-X_{10}-X_{11}-X_{12}-X_{13}-X_{14}-X_{15}-X_{16}-X_{17}-X_{18}-X_{19}$

12 $X_{06}-X_{07}-X_{08}-X_{09}-X_{10}-X_{11}-X_{12}-X_{13}-X_{14}-X_{15}-X_{16}-X_{17}-X_{18}-X_{19}$

13 $X_{07}-X_{08}-X_{09}-X_{10}-X_{11}-X_{12}-X_{13}-X_{14}-X_{15}-X_{16}-X_{17}-X_{18}-X_{19}-X_{20}$

14 $X_{07}-X_{08}-X_{09}-X_{10}-X_{11}-X_{12}-X_{13}-X_{14}-X_{15}$

1 = Alignment of overlapping peptides (2-13, n = 12 unique peptides) against amino acid sequence of CSL627, pdVWF, CSL626 or EYA-FP; amino acid indices indicate exemplified positions in naive amino acid sequence.
2-7 = Example of a peptide cluster presented by MODCs of donor X: 6 overlapping unique peptides are assigned to the same region within the amino acid sequence of CSL627, pdVWF, CSL626 or EYA-FP.
8-13 = Example of a peptide cluster presented by MODCs of donor Y: 5 overlapping unique peptides are assigned to the same region within the amino acid sequence of CSL627, pdVWF, CSL626 or EYA-FP.
14 = Core peptide sequence (9-mer) based on sequence 1 (Alignment of detected peptides) predicted by NetMHCII 3.1

The number of unique HLA-DR bound peptides of a respective HLA-DR restricted peptide cluster is further analyzed to compare antigen presentation of CSL627 in presence and absence of pdVWF, CSL626 or EYA-FP. Numbers of unique HLA-DR bound peptides per HLA-DR restricted peptide cluster are illustrated in a X-Y-Plot. On the X-axis all identified HLA-DR restricted peptide clusters with their respective number of unique HLA-DR bound peptides as result of CSL627 Antigen presentation in absence of pdVWF, CSL626 and EYA-FP are plotted against all identified HLA-DR restricted peptide clusters with their respective number of unique HLA-DR bound peptides as result of CSL627 Antigen presentation in presence of pdVWF, CSL626 and EYA-FP on the Y-Axis. Simple linear regression was conducted (Microsoft Excel) to compare CSL627 antigen presentation efficiency by HLA-DR of MODCs.

2.5 Donor Selection

A panel of peripheral blood mononuclear cell (PBMC) samples from healthy human donors was selected from the ProImmune cell bank. Each PBMC sample was HLA (Human Leukocyte Antigen) typed and cryopreserved in liquid nitrogen (vapor-phase) prior to use. The panel was selected such that, HLA class II alleles known to be highly expressed in the global population were well represented. Donors set panels and their HLA-DRB1 or HLA-DRB1/DQB1/DPB1 typing information are listed in Tables below.

TABLE 3

Donor Set A HLA-DRB1, -DQB1, -DPB1 Typing Information

| Donor | DRB1_1 | DRB1_2 | DQB1_1 | DQB1_2 | DPB1_1 | DPB1_2 |
|---|---|---|---|---|---|---|
| #1 | *03:01 | *15:01 | *02:01 | *06:02 | *04:01 | *09:01 |
| #2 | *03:01 | *09:01 | *02:01 | *03:03 | *02:01 | *04:02 |
| #3 | *11:01 | *15:01 | *03:01 | *06:02 | *03:01 | *04:01 |
| #4 | *04:01 | *13:02 | *03:02 | *06:04 | *03:01 | *04:01 |
| #5 | *03:01 | *15:01 | *02:01 | *06:02 | *01:01 | *04:02 |
| #6 | *15:01 | *15:01 | *06:02 | *06:02 | *04:01 | *04:01 |
| #7 | *01:01 | *04:01 | *03:02 | *05:01 | *03:01 | *04:01 |
| #8 | *03:01 | *08:01 | *02:01 | *04:02 | *02:01 | *03:01 |
| #9 | *11:01 | *11:13 | *03:01 | *05:03 | *03:01 | *04:01 |
| #10 | *03:01 | *13:01 | *02:01 | *06:03 | *03:01 | *04:01 |
| #11 | *04:04 | *15:01 | *03:02 | *06:02 | *01:01 | *02:01 |
| #12 | *04:01 | *07:01 | *02:02 | *03:02 | *04:01 | *11:01 |

TABLE 4

Donor Set B HLA-DRB1 Typing Information

| Donor | DRB1_1 | DRB1_2 |
|---|---|---|
| #13 | *04:05 | *04:05 |
| #14 | *04:01 | *07:01 |
| #15 | *04:04 | *11:04 |
| #16 | *03:01 | *04:01 |
| #17 | *04:01 | *13:03 |
| #18 | *03:01 | *04:01 |
| #19 | *03:01 | *14:01 |
| #20 | *15:01 | *15:01 |
| #21 | *04:01 | *07:01 |
| #22 | *04:01 | *15:01 |
| #23 | *04:04 | *07:01 |
| #24 | *07:01 | *13:01 |

TABLE 5

Donor Set C HLA-DRB1 Typing Information

| Donor | DRB1_1 | DRB1_2 |
|---|---|---|
| #25 | *15:01 | *16:01 |
| #26 | *03:01 | *15:01 |
| #27 | *07:01 | *15:01 |
| #28 | *07:01 | *15:01 |
| #29 | *04:01 | *07:01 |
| #30 | *07:01 | *12:01 |
| #31 | *03:01 | *13:02 |
| #32 | *04:01 | *04:04 |
| #33 | *13:01 | *15:01 |
| #34 | *07:01 | *14:01 |
| #35 | *09:01 | *13:01 |
| #36 | *07:01 | *15:01 |

2.6.1 Results

MHC Class II Antigen Presentation of CSL627 by MODCs in Presence and Absence of pdVWF Endogenous proteins detection by sequencing mass spectrometry (LAMP-1, LAMP-2, TFRC, FcER2/FcGR2, ApoB, ITGAM, CLIP) and flow cytometry monitoring of DC surface marker (CD209, CD86, HLA-DR) was deemed acceptable to generate robust sample data.

TABLE 6

| | Number of Peptide Clusters | | | |
|---|---|---|---|---|
| | CSL627-derived | | | VWF-derived |
| Haplotype | DRB1 | DQB1 | DPB1 | DRB1 |
| CSL627 | 38.0 ± 7.1 [A,B] | 20 [A] | 14 [A] | — |
| CSL627 + VWF | 14.5 ± 0.7 [A,C] | 2 [A] | 4 [A] | 13.0 ± 5.7 [A,C] |
| VWF | — | — | — | 17 [C] |

[A] donor set A;
[B] donor set B;
[C] donor set C as source for PBMCs

Table 6 summarizes the data generated by ProImmune ProPresent® Antigen presentation assays with three independent panels A, B and C of in total 36 healthy, unrelated, HLA-DRB1- and HLA-DRB1/DQB1/DPB1-typed donors as source of PBMCs. Immature DCs were loaded either with 146.4 nM CSL627 only or with 146.4 nM CSL627 pre-complexed with 1.9667 µM pdVWF based on monomer content. CSL627 antigen presentation in the absence of pdVWF and subsequent sequencing mass spectrometry identified 38.0±7.1 HLA-DRB1 Peptide Clusters in two independent panel of donors. CSL627 antigen presentation in the presence of pdVWF and subsequent sequencing mass spectrometry identified 14.5±0.7 HLA-DRB1 Peptide Clusters in two independent panel of donors. pdVWF was able to reduce CSL627 HLA-DRB1 restricted antigen presentation based on the number of identified peptide clusters 2.2- to 3.0 fold. CSL627 Antigen presentation in presence of pdVWF was reduced 10-fold based on identified HLA-DQB1 restricted peptide clusters and 3.5-fold based on identified HLA-DQB1 restricted peptide clusters using one panel of HLA-DRB1/DQB1/DPB1-typed donors. Approximately 50-70% of CSL627 peptide clusters were HLA-DRB1 restricted and approximately 30-50% of CSL627 peptide clusters were presented by HLA-DQB1 and HLA-DPB1. While the number of CSL627-derived and HLA- DRB1-, HLA-DQB1- and HLA-DPB1-restricted peptide clusters decreased or some even disappeared in the presence of pdVWF, no additional or new CSL627-derived and HLA-DRB1-, HLA-DQB1- and HLA-DPB1-restricted peptide cluster was detected and no CSL627-derived and HLA-DRB1-, HLA-DQB1- and HLA-DPB1-restricted peptide cluster was increased compared to the peptide cluster sequences derived from CSL627 antigen presentation without pdVWF.

Antigen presentation of pdVWF in presence or absence of CSL627 was investigated in a panel of HLA-DRB1/DQB1/DPB1-typed donors and a second independent panel of HLA-DRB1-typed donors. Antigen presentation of pdVWF in absence of CSL627 was investigated in a panel of HLA-DRB1-typed donors. Antigen presentation of pdVWF in presence of CSL627 was investigated in both panels, HLA-DRB1/DQB1/DPB1-typed and HLA-DRB1-typed donors. pdVWF antigen presentation in the presence of CSL627 and subsequent sequencing mass spectrometry identified 13.0±5.7 HLA-DRB1 Peptide Clusters in two independent panels of donors where pdVWF antigen presentation in the absence of CSL627 identified 17 HLA-DRB1 Peptide Clusters in one panel of donors.

Multi-fold reduction of antigen presentation of CSL627 based on the number of peptide clusters in presence of molar excess of pdVWF may be biased through abundant pdVWF protein load. However, pdVWF antigen presentation was not influenced through the presence or absence of CSL627. Considering the molar excess load of pdVWF compared with CSL627 protein load, antigen presentation of pdVWF was less effective than for CSL627. An inhibition of CSL627 antigen presentation through excess competing pdVWF-derived peptides cannot be excluded, but had also lead to increased antigen presentation of pdVWF when DCs were loaded with pdVWF only.

TABLE 7

| | Number of Unique Peptides | | | |
|---|---|---|---|---|
| | CSL627-derived | | | VWF-derived |
| Haplotype | DRB1 | DQB1 | DPB1 | DRB1 |
| CSL627 | 1035 ± 99 [A,B] | 65 [A] | 170 [A] | — |
| CSL627 + VWF | 192 ± 9.9 [A,C] | 3 [A] | 12 [A] | 39.0 ± 28.3 [A,C] |
| VWF | — | — | — | 60 [C] |

[A] donor set A;
[B] donor set B;
[C] donor set C as source for PBMCs

Table 7 summarizes the data generated by ProImmune ProPresent® Antigen presentation assays with three independent panels A, B and C of in total 36 healthy, unrelated, HLA-DRB1- and HLA-DRB1/DQB1/DPB1-typed donors as source of PBMCs. Immature DCs were loaded either with 146.4 nM CSL627 only or with 146.4 nM CSL627 pre-complexed with 1.9667 μM pdVWF based on monomer content. CSL627 antigen presentation in the absence of pdVWF and subsequent sequencing mass spectrometry identified 1035±99 unique HLA-DRB1 bound peptides in two independent panel of donors. CSL627 antigen presentation in the presence of pdVWF and subsequent sequencing mass spectrometry identified 192±9.9 unique HLA-DRB1 bound peptides in two independent panels of donors. pdVWF was able to reduce CSL627 HLA-DRB1 restricted antigen presentation based on the number of unique HLA-DRB1 bound peptides 4.8- to 6.0 fold. CSL627 Antigen presentation in presence of pdVWF was reduced 21.7-fold based on identified unique HLA-DQB1 bound peptides and 14.2-fold based on identified unique HLA-DPB1 bound peptides using one panel of HLA-DRB1/DQB1/DPB1-typed donors. Approxim 2.6.2 Results MHC Class II Antigen Presentation of CSL627 by MODCs in Presence and Absence of CSL626

Endogenous proteins detection by sequencing mass spectrometry (LAMP-1, LAMP-2, TFRC, FcER2/FcGR2, ApoB, ITGAM, CLIP) and flow cytometry monitoring of DC surface marker (CD209, CD86, HLA-DR) was deemed acceptable to generate robust sample data.

TABLE 8

Number of Peptide Clusters

| Haplotype | CSL627-derived DRB1 | CSL626-derived DRB1 |
|---|---|---|
| CSL627 | 38.0 ± 7.1 [A,B] | — |
| CSL627 + CSL626 | 20 [B] | 3 [B] |
| CSL626 | — | 2 [B] |

[A] donor set A;
[B] donor set B as source for PBMCs

Table 8 summarizes the data generated by ProImmune ProPresent® Antigen presentation assays with two independent panels A and B of 24 healthy, unrelated, HLA-DRB1-typed donors as source of PBMCs. Immature DCs were loaded either with 146.4 nM CSL627 only or with 146.4 nM CSL627 pre-complexed with 1.9667 µM CSL626 based on monomer content. CSL627 antigen presentation in the absence of CSL626 and subsequent sequencing mass spectrometry identified 38.0±7.1 HLA-DRB1 Peptide Clusters in two independent panels of donors. CSL627 antigen presentation in the presence of CSL626 and subsequent sequencing mass spectrometry identified 20 HLA-DRB1 Peptide Clusters in two independent panel of donors. CSL626 was able to reduce CSL627 HLA-DRB1 restricted antigen presentation based on the number of identified peptide clusters 1.55- to 2.55-fold.

While the number of CSL627-derived and HLA-DRB1-restricted peptide clusters decreased or some even disappeared in the presence of CSL626, no additional or new CSL627-derived and HLA-DRB1-restricted peptide cluster was detected and no CSL627-derived and HLA-DRB1-restricted peptide cluster was increased compared to the peptide cluster sequences derived from CSL627 antigen presentation without CSL626.

Antigen presentation of CSL626 in presence and absence of CSL627 was investigated in a panel of 12 HLA-DRB1-typed donors. CSL626 antigen presentation in the presence of CSL627 and subsequent sequencing mass spectrometry identified 3 HLA-DRB1 Peptide Clusters in 12 healthy, unrelated donors where CSL626 antigen presentation in the absence of CSL627 identified 2 HLA-DRB1 Peptide Clusters in the same set of donors.

Reduction of antigen presentation of CSL627 based on the number of peptide clusters in presence of molar excess of CSL626 may be biased through abundant CSL626 protein load. However, CSL626 antigen presentation was not influenced significantly through the presence or absence of CSL627. Considering the molar excess load of CSL626 compared with CSL627 protein load, antigen presentation of CSL626 was less effective than for CSL627. An inhibition of CSL627 antigen presentation through excess competing CSL626-derived peptides cannot be excluded, but had also lead to increased antigen presentation of CSL626 when DCs were loaded with CSL626 only.

TABLE 9

Number of Unique Peptides

| Haplotype | CSL627-derived DRB1 | CSL626-derived DRB1 |
|---|---|---|
| CSL627 | 1035 ± 99 [A,B] | — |
| CSL627 + CSL626 | 212 [B] | 24 [B] |
| CSL626 | — | 28 [B] |

[A] donor set A;
[B] donor set B as source for PBMCs

Table 9 summarizes the data generated by ProImmune ProPresent® Antigen presentation assays with two independent panels A and B of 24 healthy, unrelated, HLA-DRB1-typed donors as source of PBMCs. Immature DCs were loaded either with 146.4 nM CSL627 only or with 146.4 nM CSL627 pre-complexed with 1.9667 µM CSL626 based on monomer content. CSL627 antigen presentation in the absence of CSL626 and subsequent sequencing mass spectrometry identified 1035±99 unique HLA-DRB1 bound peptides in two independent panels of donors. CSL627 antigen presentation in the presence of CSL626 and subsequent sequencing mass spectrometry identified 212 unique HLA-DRB1 bound peptides in a set of 12 donors. CSL626 was able to reduce CSL627 HLA-DRB1 restricted antigen presentation based on the number of unique HLA-DRB1 bound peptides 4.4- to 5.4-fold.

Antigen presentation of CSL626 in presence and absence of CSL627 was investigated in a panel of HLA-DRB1-typed donors. CSL626 antigen presentation in the presence of CSL627 and subsequent sequencing mass spectrometry identified 24 unique HLA-DRB1 bound peptides in 12 healthy, unrelated donors where CSL626 antigen presentation in the absence of CSL627 identified 28 unique HLA-DRB1 bound peptides in the same set of donors.

Multi-fold reduction of antigen presentation of CSL627 based on the number of unique peptides in presence of molar excess of CSL626 may be biased through abundant CSL626 protein load. However, CSL626 antigen presentation was not influenced through the presence or absence of CSL627. Considering the molar excess load of CSL626 compared with CSL627 protein load, antigen presentation of CSL626 was less effective than for CSL627. Only approximately 10% of unique peptides identified were CSL626-derived when loaded with CSL627 to DCs. An inhibition of CSL627 antigen presentation through excess competing CSL626-derived peptides cannot be excluded, but had also lead to significantly increased antigen presentation of CSL626 when DCs were loaded with CSL626 only.

Figure 7:
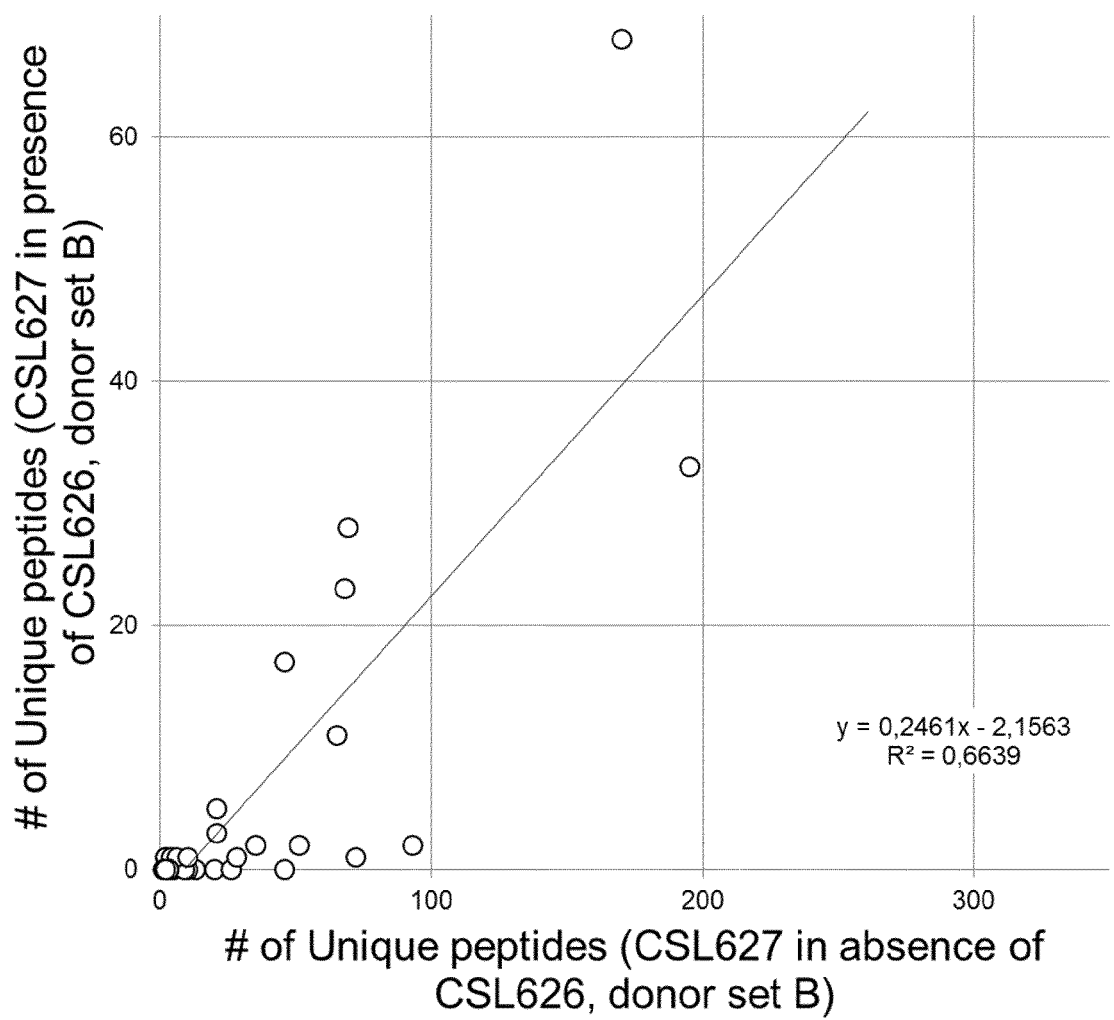
FIG. 7 shows a comparison of ProImmune ProPresent® Antigen presentation of CSL627 in presence and absence of CSL626: each data point represents a HLA-DR restricted peptide cluster; the number of CSL627-derived, unique HLA-DR bound peptides of HLA-DR restricted peptide clusters was plotted in absence (X-Axis) and presence (Y-Axis) of CSL626. X-Y-Plot, linear regression (MS Excel)

FIG. 7 shows a comparison of ProImmune ProPresent® Antigen presentation of CSL627 in presence and absence of CSL626. Each data point represents a HLA-DR restricted peptide cluster. The number of CSL627-derived, unique HLA-DR bound peptides of HLA-DR restricted peptide clusters was plotted in absence (X-Axis) and presence (Y-Axis) of CSL626. X—Y-Plot, linear regression (MS Excel).

FIG. 7 illustrates ProImmune ProPresent® Antigen presentation assays with two independent panels A and B of 24 healthy, unrelated, HLA-DRB1-typed donors as source of PBMCs. Immature DCs were loaded either with 146.4 nM CSL627 only or with 146.4 nM CSL627 pre-complexed with 1.9667 µM CSL626 based on monomer content.

Vis-à-vis the overall number of unique HLA-DRB1 bound, CSL627-derived peptides of each peptide cluster was reduced in presence of CSL626. A number of peptide clusters was identified when DCs were loaded with CSL627 without CSL626 but some CSL627-derived peptide clusters disappeared in the presence of CSL626 (Table 6 and 7). No peptide cluster was more efficient presented based on the number of unique HLA-DRB1 bound peptides when CSL627 was tested in the presence of CSL626 compared to CSL627 without CSL626.

Linear regression correlates the data with a slope of $0.25*X$ ($R^2=0.66$). In the presence of CSL626, CSL627 antigen presentation is approximately one fourth (approx. 25%) of the antigen presentation efficiency of CSL627 in absence of CSL626.

2.6.3 Results

MHC Class II Antigen Presentation of CSL627 by MODCs in Presence and Absence of EYA-FP Endogenous proteins detection by sequencing mass spectrometry (LAMP-1, LAMP-2, TFRC, FcER2/FcGR2, ApoB, ITGAM, CLIP) and flow cytometry monitoring of DC surface marker (CD209, CD86, HLA-DR) was deemed acceptable to generate robust sample data.

TABLE 10

| | Number of Peptide Clusters | |
| --- | --- | --- |
| Haplotype | CSL627-derived DRB1 | EYA-FP-derived DRB1 |
| CSL627 | 38.0 ± 7.1 [A,B] | — |
| CSL627 + EYA-FP | 15 [B] | 2 [B] |
| EYA-FP | — | 2 [B] |

[A] donor set A;
[B] donor set B as source for PBMCs

Table 10 summarizes the data generated by ProImmune ProPresent® Antigen presentation assays with two independent panels A and B of 24 healthy, unrelated, HLA-DRB1-typed donors as source of PBMCs. Immature DCs were loaded either with 146.4 nM CSL627 only or with 146.4 nM CSL627 pre-complexed with 1.9667 µM EYA-FP based on monomer content. CSL627 antigen presentation in the absence of EYA-FP and subsequent sequencing mass spectrometry identified 38.0±7.1 HLA-DRB1 Peptide Clusters in two independent panels of donors. CSL627 antigen presentation in the presence of EYA-FP and subsequent sequencing mass spectrometry identified 15 HLA-DRB1 Peptide Clusters in two independent panel of donors. EYA-FP was able to reduce CSL627 HLA-DRB1 restricted antigen presentation based on the number of identified peptide clusters 2.1- to 3.0-fold.

While the number of CSL627-derived and HLA-DRB1-restricted peptide clusters decreased or some even disappeared in the presence of EYA-FP, no additional or new CSL627-derived and HLA-DRB1-restricted peptide cluster was detected and no CSL627-derived and HLA-DRB1-restricted peptide cluster was increased compared to the peptide cluster sequences derived from CSL627 antigen presentation without EYA-FP.

Antigen presentation of EYA-FP in presence and absence of CSL627 was investigated in a panel of 12 HLA-DRB1-typed donors. EYA-FP antigen presentation in the presence of CSL627 and subsequent sequencing mass spectrometry identified 2 HLA-DRB1 Peptide Clusters in 12 healthy, unrelated donors where EYA-FP antigen presentation in the absence of CSL627 identified the same 2 HLA-DRB1 Peptide Clusters in the same set of donors.

Reduction of antigen presentation of CSL627 based on the number of peptide clusters in presence of molar excess of EYA-FP may be biased through abundant EYA-FP protein load. However, EYA-FP antigen presentation was not influenced significantly through the presence or absence of CSL627. Considering the molar excess load of EYA-FP compared with CSL627 protein load, antigen presentation of EYA-FP was less effective than for CSL627. An inhibition of CSL627 antigen presentation through excess competing EYA-FP-derived peptides cannot be excluded, but had also lead to increased antigen presentation of EYA-FP when DCs were loaded with EYA-FP only.

TABLE 11

| | Number of Unique Peptides | |
| --- | --- | --- |
| Haplotype | CSL627-derived DRB1 | EYA-FP-derived DRB1 |
| CSL627 | 1035 ± 99 [A,B] | — |
| CSL627 + EYA-FP | 241 [B] | 21 [B] |
| EYA-FP | — | 20 [B] |

[A] donor set A;
[B] donor set B as source for PBMCs

Table 11 summarizes the data generated by ProImmune ProPresent® Antigen presentation assays with two independent panels A and B of 24 healthy, unrelated, HLA-DRB1-typed donors as source of PBMCs. Immature DCs were loaded either with 146.4 nM CSL627 only or with 146.4 nM CSL627 pre-complexed with 1.9667 µM EYA-FP based on monomer content. CSL627 antigen presentation in the absence of EYA-FP and subsequent sequencing mass spectrometry identified 1035±99 unique HLA-DRB1 bound peptides in two independent panels of donors. CSL627 antigen presentation in the presence of EYA-FP and subsequent sequencing mass spectrometry identified 241 unique HLA-DRB1 bound peptides in a set of 12 donors. EYA-FP was able to reduce CSL627 HLA-DRB1 restricted antigen presentation based on the number of unique HLA-DRB1 bound peptides 3.9- to 4.7-fold.

Antigen presentation of EYA-FP in presence and absence of CSL627 was investigated in a panel of HLA-DRB1-typed donors. EYA-FP antigen presentation in the presence of CSL627 and subsequent sequencing mass spectrometry identified 21 unique HLA-DRB1 bound peptides in 12 healthy, unrelated donors where EYA-FP antigen presentation in the absence of CSL627 identified 20 unique HLA-DRB1 bound peptides in the same set of donors.

Multi-fold reduction of antigen presentation of CSL627 based on the number of unique peptides in presence of molar excess of EYA-FP may be biased through abundant EYA-FP protein load. However, EYA-FP antigen presentation was not influenced through the presence or absence of CSL627. Considering the molar excess load of EYA-FP compared with CSL627 protein load, antigen presentation of EYA-FP was less effective than for CSL627. Only approximately 8% of unique peptides identified were EYA-FP-derived when loaded with CSL627 to DCs. An inhibition of CSL627 antigen presentation through excess competing EYA-FP-derived peptides cannot be excluded, but had also lead to significantly increased antigen presentation of EYA-FP when DCs were loaded with EYA-FP only.

Figure 8:
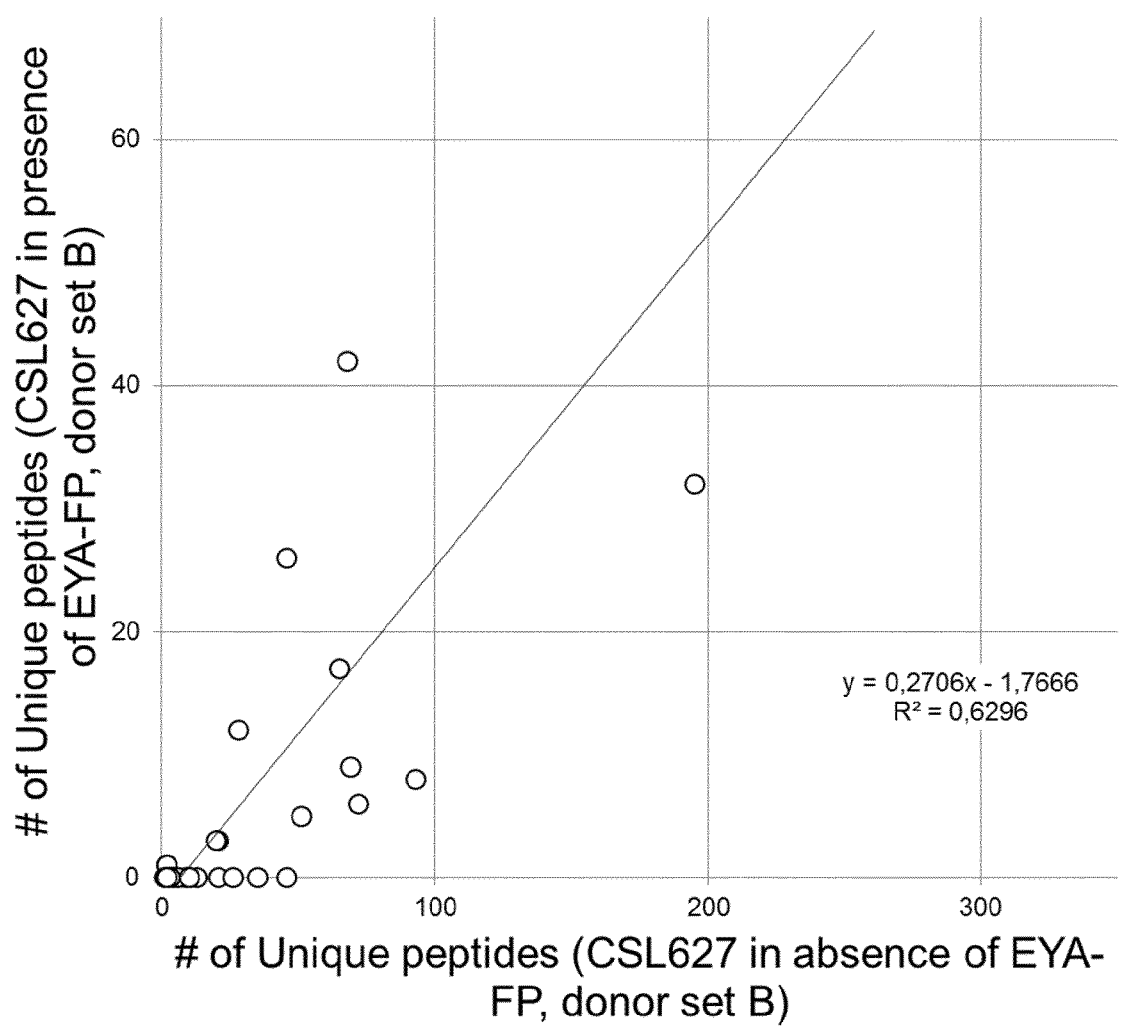
FIG. 8 shows a comparison of ProImmune ProPresent® Antigen presentation of CSL627 in presence and absence of EYA-FP: each data point represents a HLA-DR restricted peptide cluster; the number of CSL627-derived, unique HLA-DR bound peptides of HLA-DR restricted peptide clusters was plotted in absence (X-Axis) and presence (Y-Axis) of EYA-FP. X-Y-Plot, linear regression (MS Excel).

FIG. 8 shows a comparison of ProImmune ProPresent® Antigen presentation of CSL627 in presence and absence of EYA-FP. Each data point represents a HLA-DR restricted peptide cluster. The number of CSL627-derived, unique HLA-DR bound peptides of HLA-DR restricted peptide clusters was plotted in absence (X-Axis) and presence (Y-Axis) of EYA-FP. X—Y-Plot, linear regression (MS Excel).

FIG. 8 illustrates ProImmune ProPresent® Antigen presentation assays with two independent panels A and B of 24 healthy, unrelated, HLA-DRB1-typed donors as source of PBMCs. Immature DCs were loaded either with 146.4 nM CSL627 only or with 146.4 nM CSL627 pre-complexed with 1.9667 µM EYA-FP based on monomer content.

Vis-à-vis the overall number of unique HLA-DRB1 bound, CSL627-derived peptides of each peptide cluster was reduced in presence of EYA-FP. A number of peptide clusters was identified when DCs were loaded with CSL627 without EYA-FP but some CSL627-derived peptide clusters disappeared in the presence of EYA-FP (Table 8 and 9). No peptide cluster was more efficient presented based on the number of unique HLA-DRB1 bound peptides when CSL627 was tested in the presence of EYA-FP compared to CSL627 without EYA-FP.

Linear regression correlates the data with a slope of $0.27*X$ ($R^2=0.63$). In the presence of EYA-FP, CSL627 antigen presentation is approximately one fourth of the antigen presentation efficiency of CSL627 in absence of EYA-FP.

The invention claimed is:

1. A method for treating a subject suffering from a blood coagulation disorder, comprising co-administering to the subject:
(a) a recombinant polypeptide comprising a truncated von Willebrand Factor (VWF) capable of binding to blood coagulation Factor VIII (FVIII); and
(b) an FVIII protein,
wherein the recombinant polypeptide comprises at least one amino acid substitution chosen from S764P/S766W/V1083A, S764G/S766Y/V1083A, S764E/S766Y/V1083A, N1011S/V1083A/K1181E, S766Y/V1083A, V1083A, S1042T, V805A/Q1158L, and K912E/T1088S, compared to SEQ ID NO:4, and
wherein the recombinant polypeptide reduces the immunogenicity of FVIII.

2. The method of claim 1, wherein the reduced immunogenicity of FVIII comprises a subject's reduced humoral immune response against FVIII and/or a reduced cell-mediated immune response against FVIII.

3. The method of claim 1, wherein the reduction of immunogenicity of FVIII is achieved or accompanied by a reduced uptake of FVIII into subject's antigen presenting cells (APCs) in the presence of the co-administered recombinant polypeptide compared to a reference treatment, wherein said reference treatment is identical to said treatment, except said FVIII is administered without co-administration of the recombinant polypeptide.

4. The method of claim 3, wherein following co-administration of the recombinant polypeptide and FVIII, the portion of the subject's APCs having internalized FVIII are reduced by at least a factor of 1.1, by at least a factor of 1.2, by at least a factor of 1.3, by at least a factor of 1.4, by at least a factor of 1.5, by at least a factor of 2, by at least a factor of 3, by at least a factor of 4, by at least a factor of 5, or by at least a factor of 10, when compared to a reference treatment, wherein said reference treatment is identical to said treatment, except said FVIII is administered without co-administration of the recombinant polypeptide.

5. The method of claim 3, wherein the $IC_{50}$ value for the co-administered recombinant polypeptide exceeds the $IC_{50}$ value of full length VWF by not more than a factor of 3, by not more than a factor of 2.5, by not more than a factor of 2.4, by not more than a factor of 2.3, by not more than a factor of 2.2, by not more than a factor of 2.1, by not more than a factor of 2.0, by not more than a factor of 1.8, by not more than a factor of 1.5, by not more than a factor of 1.3, by not more than a factor of 1.2, or by not more than a factor of 1.1.

6. The method of claim 3, wherein the $IC_{50}$ value for the co-administered recombinant polypeptide is either identical or reduced by a factor of at least 1.2, of at least 1.5, of at least 2, of at least 2.5 or of at least 3 when compared to a respective $IC_{50}$ value for a full length VWF.

7. The method of claim 1, wherein the reduction of immunogenicity of FVIII following administration of the recombinant polypeptide is achieved or accompanied by a reduced MHC class II type antigen presentation of FVIII peptides by the subject's antigen presenting cells (APCs) in the presence of the recombinant polypeptide when compared to a reference treatment, wherein said reference treatment is identical to said treatment, except said FVIII is administered without administration of the recombinant polypeptide, and wherein the MHC class II type antigen presentation of FVIII peptides by the subject's antigen presenting cells (APCs) is reduced by a factor of at least 1.5, at least 2.0, at least 2.5, at least 3.0, at least 3.5, or at least 4.0.

8. The method of claim 1, wherein the subject is previously untreated with FVIII.

9. The method of claim 1, wherein the subject has a risk and/or is expected of developing an immune reaction against FVIII.

10. The method of claim 1, wherein the titer of inhibitory antibodies directed against FVIII is reduced by at least 2%, by at least 5%, by at least 10%, by at least 15%, by at least 20%, by at least 30%, by at least 40%, by at least 50%, or by at least 80%, when compared to the titer of FVIII antibodies in a subject following a reference treatment, wherein said reference treatment is identical to said treatment, except said FVIII is administered without co-administration of said recombinant polypeptide.

11. The method of claim 1, wherein the frequency of inhibitory antibodies directed against FVIII in a subject population is reduced by at least 5%, by at least 10%, by at least 15%, by at least 20%, by at least 30%, by at least 40%, by at least 50%, or by at least 80%, when compared to the frequency of FVIII antibodies in a subject population following a reference treatment, wherein said reference treatment is identical to said treatment, except said FVIII is administered without co-administration of said recombinant polypeptide.

12. The method of claim 1, wherein the recombinant polypeptide is administered as a dimer.

13. The method of claim 1, wherein the molar ratio of the recombinant polypeptide to the FVIII is at least 2:1, at least 3:1, at least 4:1, at least 5:1, at least 6:1, at least 8:1, at least 10:1, at least 15:1, at least 20:1, at least 25:1, at least 50:1, at least 70:1, at least 80:1, at least 100:1, or at least 150:1.

14. The method of claim 1, wherein the subject is a human subject and the blood coagulation disorder is hemophilia A.

15. The method of claim 1, wherein said polypeptide is administered intravenously, subcutaneously, intradermally, orally, transdermally, intranasally, intraperitoneally, topically, locally, sublingually, or intramuscularly.

16. The method of claim 1, wherein said polypeptide comprises a functional VWF D' domain and/or a functional VWF D3 domain.

17. The method of claim 1, wherein the truncated VWF comprises an amino acid sequence having a sequence identity of at least 90% to amino acids 776 to 805 of SEQ ID NO:4.

18. The method according to claim 1, wherein said recombinant polypeptide comprises a half-life extending moiety (HLEM).

19. The method of claim 18, wherein the HLEM is a heterologous amino acid sequence fused to the truncated VWF, wherein said heterologous amino acid sequence comprises a polypeptide chosen from:

immunoglobulin constant regions and portions thereof, albumin and fragments thereof, transferrin and fragments thereof, C-terminal peptide of human chorionic gonadotropin, an XTEN sequence, homo-amino acid repeats (HAP), proline-alanine-serine repeats (PAS), afamin, alpha-fetoprotein, Vitamin D binding protein, polypeptides capable of binding under physiological conditions to albumin or immunoglobulin constant regions, polypeptides capable of binding to the neonatal Fc receptor (FcRn), and combinations thereof.

20. The method of claim 1, wherein the truncated VWF comprises an amino acid sequence having a sequence identity of at least 90% to amino acids 764 to 1242 of SEQ ID NO:4.

* * * * *